United States Patent
zur Hausen et al.

(10) Patent No.: US 9,624,511 B2
(45) Date of Patent: Apr. 18, 2017

(54) SPECIFIC TT VIRUS SEQUENCES AND CHIMERIC TT VIRUS HOST CELL DNA MOLECULES FOR USE IN DIAGNOSIS, PREVENTION AND TREATMENT OF CANCER AND AUTOIMMUNITY

(71) Applicant: Deutsches Krebsforschungszentrum, Heidelberg (DE)

(72) Inventors: Harald zur Hausen, Waldmichelbach (DE); Ethel-Michele de Villiers, Waldmichelbach (DE)

(73) Assignee: Deutsches Krebsforschungszentrum, Heidelberg (DE)

( * ) Notice: Subject to any disclaimer, the term of this patent is extended or adjusted under 35 U.S.C. 154(b) by 0 days.

(21) Appl. No.: 14/479,803

(22) Filed: Sep. 8, 2014

(65) Prior Publication Data

US 2015/0247165 A1    Sep. 3, 2015

Related U.S. Application Data

(63) Continuation of application No. 12/821,634, filed on Jun. 23, 2010, now abandoned.

(51) Int. Cl.
| | | |
|---|---|---|
| *C12N 15/86* | (2006.01) | |
| *C12N 7/00* | (2006.01) | |
| *C12Q 1/70* | (2006.01) | |
| *C07K 14/005* | (2006.01) | |

(52) U.S. Cl.
CPC ............ *C12N 15/86* (2013.01); *C07K 14/005* (2013.01); *C12N 7/00* (2013.01); *C12Q 1/701* (2013.01); *C12N 2750/00021* (2013.01); *C12N 2750/00022* (2013.01); *C12N 2750/00034* (2013.01); *C12N 2750/00043* (2013.01)

(58) Field of Classification Search
None
See application file for complete search history.

(56) References Cited

U.S. PATENT DOCUMENTS

| 6,395,472 B1 * | 5/2002 | Leary ...................... C12Q 1/701 435/5 |
| 2011/0318363 A1 | 12/2011 | Zur Hausen et al. |
| 2013/0259869 A1 | 10/2013 | De Villiers et al. |
| 2015/0247165 A1 * | 9/2015 | zur Hausen ............... C12N 7/00 435/320.1 |

FOREIGN PATENT DOCUMENTS

| WO | WO 00/28039 A2 | | 5/2000 |
| WO | WO 00/46407 | * | 8/2000 |
| WO | WO 00/46407 A2 | | 8/2000 |
| WO | WO 01/42299 A2 | | 6/2001 |
| WO | WO 03/023027 A2 | | 3/2003 |
| WO | WO 2007/130519 A2 | | 11/2007 |
| WO | WO 2008/138619 A2 | | 11/2008 |

OTHER PUBLICATIONS

Sequence alignment of instant SEQ ID No. 27 with Geneseq database accession No. AZR50238 of zur Hausen et al EP2399928—SEQ ID No. 27.*
Sequence alignment of instant SEQ ID No. 1 with Geneseq database accession No. AAA53640 on WO200046407 by Leary et al.*
Kakalacheva et al. (Biochemical et Biophysica Acta. 2011: 1812: 132-140).*
De Villiers et al. (Journal of Virology. 2011; 85 (14): 7284-7295).*
De Villiers, E-M., et al. "Intragenomic rearrangement in TT viruses: a possible role in the pathogenesis of disease." TT Viruses. Springer Berlin Heidelberg, 2009. 91-107.*
Okamoto, H. ("History of Discoveries and Pathogenicities of TT viruses." TT Viruses. Springer Berlin Heidelberg, 2009: 1-20).*
Jarrett, R. ("The Role of Viruses in the Genesis of Hodgkin Lymphoma". Hodgkin Lymphoma. Springer-Verlag Berlin Heidelberg, 2011: 21-32).*
Beland (Journal of Infectious Disease. 2014; 209: 247-254).*
Spandole et al. (Archives of Virology. 2015; 160: 893-908).*
Sequence alignment of instant SEQ ID No. 27 with Geneseq database accession No. AZR50238 of zur Hausen et al. EP2399928—SEQ ID No. 27. Dec. 2011.*
Sequence alignment of instant SEQ ID No. 1 with Geneseq database accession No. AAA53640 of Leary et al in WO200046407 on Aug. 2000.*
Nishizawa et al., A Novel DNA Virus (TTV) Associated with Elevated Transaminase Levels in Posttransfusion Hepatitis of Unknown Etiology, Biochemical and Biophysical Research Communications, 1997, pp. 92-97, vol. 241.
Okamoto, H., TT Viruses in Animals, Division of Virology, Department of Infections and Immunity, 2009, pp. 35-52, vol. 331.
Biagini et al., Anellovirus. Virus Taxonomy, 8th Report of the International Committee for the Taxonomy of Viruses, 2005, pp. 335-341, Elsevier/Academic Press, London.
Gerner et al., Mother-to-infant transmission of TT virus, The pediatric infectious disease journal, 2000, pp. 1074-1078, vol. 19.
Goto et al., Detection Rates of TT Virus DNA in Serum of Umbilical Cord Blood, Breast Milk and Saliva, Exp. Med., 2000, pp. 203-207, vol. 191.
Leppik et al., In Vivo and In Vitro Intragenomic Rearrangement of TT Viruses, Journal of Virology, 2007, pp. 9346-9356, vol. 81.
Jelcic et al., Isolation of Multiple TT Virus Genotypes from Spleen Biopsy Tissue from a Hodgkin's Disease Patient: Genome Reorganization and Diversity in the Hypervariable Region, Journal of Virology, 2004, pp. 7698-7507, vol. 78.
De Villiers et al., Heterogeneity of TT virus related sequences isolated from human tumour biopsy specimens, J. Mol. Med., 2002, pp. 44-50, vol. 80.
De Villiers et al., TTV infection in colorectal cancer tissues and normal mucosa, Int. J. Cancer, 2007, pp. 2109-2112, vol. 121.
De Villiers et al., Intragenomic Rearrangement in TT Viruses: A Possible Role in the Pathogenesis of Disease, , Curr. Topics Microbiol. Immunol, 2009, pp. 91-107, vol. 331.

(Continued)

*Primary Examiner* — Shanon A Foley

(74) *Attorney, Agent, or Firm* — Crowell & Moring LLP

(57) ABSTRACT

Described are single-stranded new sequences of TT viruses, rearranged TTV sequences and hybrid molecules of a specific TT virus sequence and host cell DNA that are capable of replicating autonomously for use in diagnosis, prevention and treatment of diseases like cancer and autoimmunity. In addition, it relates to the use of such molecules as gene vectors and artificial chromosomes.

20 Claims, 43 Drawing Sheets

(56) References Cited

OTHER PUBLICATIONS

Figure 1:
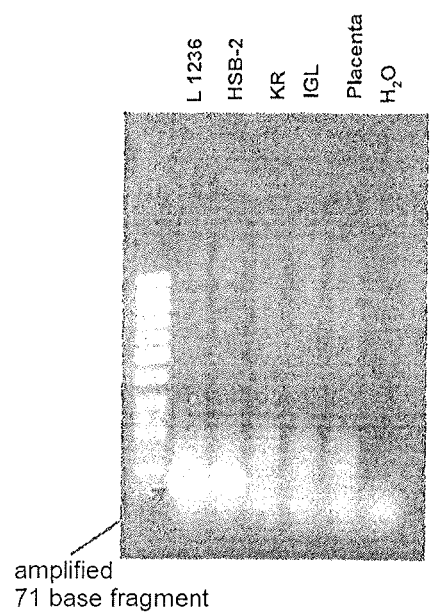

Matsukura et al., Phosphorothioate analogs of oligodeoxynucleotides: Inhibitors of replication and cytopathic effects of human immunodeficiency virus, 1987, pp. 7706-7710, vol. 84.

Miller et al., Nonionic Nucleic Acid Analogues. Synthesis and Characterization of Dideoxyribonucleoside Methylphophonates, Biochemisty, 1979, pp. 5134-5143, vol. 18.

Nielsen et al., Sequence-Selective Recognition of DNA by Strand Displacement with a Thymine-Substituted Polyamide, Science, 1991, pp. 1497-1500, vol. 254.

Nielsen et al., Sequence specific inhibition of DNA restriction enzyme cleavage of PNA, Nucleic Acids Research, 1993, pp. 197-200, vol. 21.

Asseline et al., Nucleic acid-binding molecules with high affinity and base sequence specificity: Intercalcating agents covalently linkde to oligodeoxynucleotides, Proc. Natl. Acad. Science. USA, 1984, pp. 3297-3301, vol. 81.

Kwok et al., Effects of primer-template mismatches on the polymerase chain reaction: Human immunodeficiency virus type 1 model studies, Nucleic Acids Research, 1990, pp. 999-1005, vol. 18.

Landegren et al., A Ligase-Mediated Gene Detection Technique, Science, 1988, pp. 1077-1080, vol. 241.

Wu et al., The Ligation Amplication Reaction (LAR)—Amplification of Specific DNA Sequences Using Sequential Rounds of Template-Dependent Ligation, Genomics, 1989, pp. 560-569, vol. 4.

Walker et al., Strand displacement amplification—an isothermal, in vitro DNA amplification technique, Nucleic Acids Research, 1992, pp. 1691-1696, vol. 20.

Guatelli et al., Isothermal, in vitro amplification of nucleic acids by a multienzyme reaction modeled after retroviral replication, Proc. Natl. Acad. Sci. USA, 1990, pp. 1874-1878, vol. 87.

Compton, J., Nucleic acid sequence-based amplification, Nature Publishing Group, 1991, pp. 91-92, vol. 350.

Kwoh et al., Transcription-based amplification system and detection of amplified human immunodeficiency virus type 1 with a bead-based sandwich hybridization format, Proc. Natl. Acad. Sci. USA, 1989, pp. 1173-1177, vol. 86.

Duck, P., Probe Amplifier System Based on Chimeric Cycling Oligonucleotides, BioTechniques, 1990, pp. 142-147, vol. 9.

Lizardi et al., Exponential amplification of nucleic acids: new diagnostics using DNA polymerases and RNA replicas, Trends Biotechnol.1991, pp. 53-58, vol. 9.

Lomeli et al., Quantitive Assays Based on the Use of Replicatable Hybridization Probes, Clin. Chem. 1989, pp. 1826-1831, vol. 35.

Köhler et al., Continuous cultures of fused cells secreting antibody of predefined specificity, Nature Publishing Group, 1975, p. 495, vol. 256.

Wahl et al., Improved Radioimaging and Tumor Localization with Monoclonal F (ab')2, Journal of Nuclear Medicine, 1983, pp. 316-325, vol. 24.

Jacobs et al., The thermal stability of oligonucleotide duplexes is sequence independent in tetraalkylammonium salt solutions:application to identifying recombinant DNA clones, Nucleic Acids Research, 1988, pp. 4637-4650, vol. 16.

Zimmerman et al., Independent Regulatory Elements in the Nestin Gene Direct Transgene Expression to Neural Stem Cells or Muscle Precursors, Neuron, 1994, pp. 11-24, vol. 12.

Vidal et al., Tissue-specific control elements of the Thy-1 gene, EMBO Journal, 1990, pp. 833-840, vol. 9.

Mayford et al., CaMKII Regulates the Frequency-Response Function of Hippocampal Synapses for the Production of Both LTD and NTP, Cell, 1995, pp. 891-904, vol. 81.

Pinkert et al., An albumin enhanced located 10 kb upstream functions along with its promoter todirect efficient, liver-specific expression in transgenic mice, Genes & Development, 1987, pp. 268-276, vol. 1.

Nielsen et al., Sequence-Selective Recognition of DNA by Strand Displacement with a Thymine-Substituted Polyamide, Science, 1991 pp. 1497-1500, vol. 254.

Fingl et al., The Pharmocological Basis of Therapeutics, 1975, pp. 1-46, Macmillian Publishing Co., New York.

L. Kakkola et al., Construction and biological activity of a full-length molecular clone of human Torque teno virus (TTV) genotype 6, Febs Journal, vol. 274, No. 18, Sep. 1, 2007, pp. 4719-4730.

Y. H. Peng et al., Analysis of the entire genomes of thirteen TT virus variants classifiable into the fourth and fifth generic groups, isolated from viremic infants, Archives of Virology, vol. 147, No. 1, Jan. 1, 2002, pp. 21-41.

E-M De Villiers et al, Intragenomic rearrangements in TT viruses: a possible role in the pathogenesis of disease, Current Topics in Microbiology and Immunology, vol. 331, 2009, pp. 91-107.

M. Sospedra et al., Recognition of conserved amino acid motifs of common viruses and its role in autoimmunity, PLOS Pathogens, vol. 1, No. 4, Dec. 2005, pp. 335-348.

Torque teno virus, isolate tth25, complete genome, Accession No. XP002610817, Feb. 3, 2009.

Torque teno virus 3 strain HEL32, complete genome, Accession No. XP002662777, Aug. 27, 2004.

International Search Report dated Nov. 25, 2011, 3 pages.

De Villers et al. (Journal of Virology, 2011; 85 (14): 7284-7295).

SEQ ID No. 1 alignment with geneseq acc No. AAA53640 from WO 2000/046407, Aug. 20, 2000.

Koidl et al. Detection of transfusion transmitted virus DNA by real-time PCR. Journal of Clinical Virology 29 (2004) 277-281.

GenBank: AJ620222.1, Torque teno virus, isolate tth25, complete genome. Feb. 3, 2009. http:www.ncbi.nlm.nih.gov/nuccore/aj620222.

Kamada, et al., Transcriptional regulation of TT virus: promoter and enhancer regions in the 1.2-kd noncoding region. Virology. Apr. 10, 2004;321(2):341-8.

Yu et al. TT Virus: preferential distribution in CD19(+) peripheral blood mononuclear cells and lack of viral integration. J Med Virol. Feb. 2002; 66(2):276-84.

* cited by examiner amplified
71 base fragment

FIG. 6

```
zyb2   CGGGTGCCGA AGGTGAGTTT ACACACCGCA GTCAAGGGGC AATTCGGGCT CGGGACTGGC CGGGCCATGG G
zyb9   CGGGTGCCGA AGGTGAGTTT ACACACCGCA GTCAAGGGGC AATTCGGGCT CGGGACTGGC CGGGCTATGG G
zkb5   CGGGTGCCGT AGGTGAGTTT ACACACCGCA GTCAAGGGGC AATTCGGGCT CGGGACTGGC CGGGCTATGG G
zkb69  CGGGTGCCGG AGGTGAGTTT ACACACCGCA GTCAAGGGGC AATTCGGGCT CGGGACTGGC CGGGCTATGG G
```

FIG. 8A

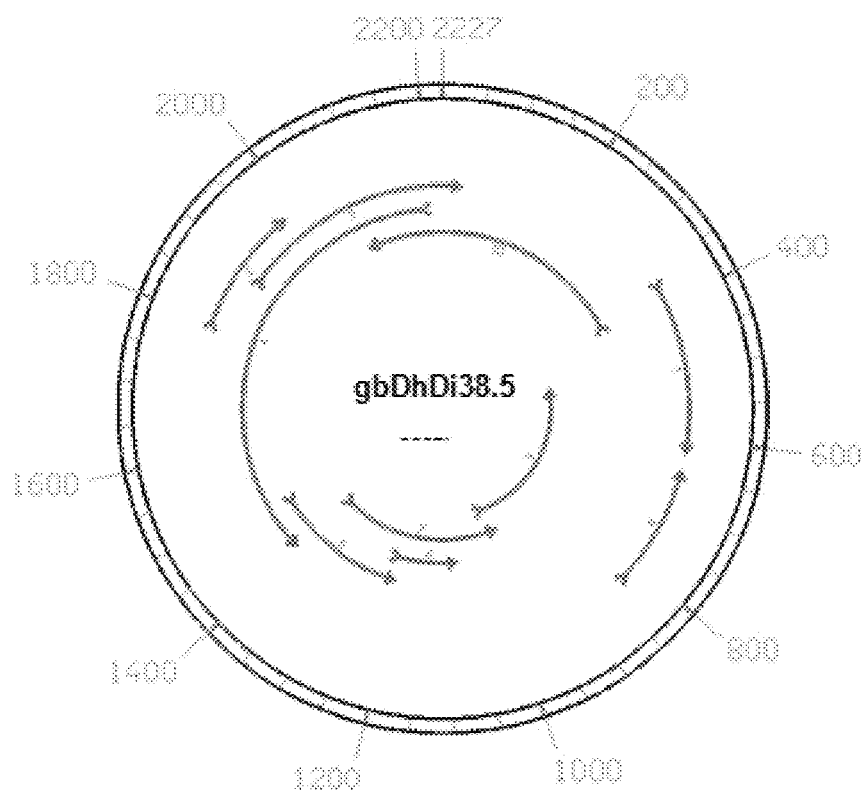

gb38.5
gbDhDi38.5.seq (zelluläre sequenz aus gb38 plus andere ms-hirn)
Length: 2227
long-pcr nach Templiphi
primer:t3pb1+2    ann.:65°C
vector:TA-cloning  pCR2.1  invitrogen

```
  1  CAATTCGTGC ACGGGACTAC AAGGAAAGGG GTTGACCCCC ACCCTCCCC
 51  GCCATGCCCA GGAGGGTGCA GACACAACTG GGAAGGTGCT AGAGACCCCG
101  GGGGGAGGCT GGGCCAGCAC CAGGCATTGG GGGGCAGGTT CCCGTCTCTA
151  CACCCCAGCC CCAGGCGGAC AGCGCGTGCC CCTCCCGCTG CCCCACCTGT
201  CACCCACCTG CTGGCCCCGG GCTGTCTCTG CTCCTGGCTC CCCTCCCAGC
251  TGCGTCCCCA GCTGCCTCTC CAGGGAGGAG TGACAGCTGG CCTGTGCCAC
301  ACCCTCGAGC CCCCCTGGAC TACCCCCTCC CTGGGGCAGG ACCCTGCCT
351  GTGGCACAAC CAAGGGGCCT GCTGATGGGG GCTCATGTGA GCAGTGCCCC
```

FIG. 8A Cont'

```
 401  AGCTGTGGGT GTGGGTGCTG CCAGCTGCCA CCGCCTTTGC CCTGGTTTCC
 451  CAGATAGACC CCGACCCACA CTCCGAAGCT GTATCATGAA CGCTGTGGTG
 501  GGCGGCTGGT GGGGAGCGGG GTTGCCGTCC CACTACCCTC TGGAAGCCTC
 551  AGCCATGAAG GGCCCCTGTG GGCACCTTTT CCCGGCACAC GGTGCTGTGT
 601  TTCTCCACTC TTGGGCTCTG CAGTGACTTG AGGGGTCAAG TCTATGATCC
 651  CACGGGAGGC TGGGCTAATG AGGGACCAG AGACCTCAGT GCTGTGCAGG
 701  GAGTCCTGAA CCACCCTGGT GGAAGGCCCA GCCCAACTCC CCAGTCCTCC
 751  CGCCAGCTCC CTGTGGTGTC CAGGAGACCT GTGGTCAGGC CTGGAGGAGA
 801  AGCTCCTCCT CCCCTCGACA TCCTCCCTGC AGCCCTTGCT CTTCACCAGA
 851  GCCTCCTGAC TCCCCAGGAC CCCAGAGAGG ACTGACCCTC TCCAGCCGAC
 901  CTCTGGGCTC AGGACAGCTG GGCGGGGCAG CCACAGGAGC TGCCTGTAGG
 951  GAGCAGAGTC AGGACGGGGA CCGAGCCGGA CACCCATTCT GGAAGTGTCT
1001  GCACTTCCAG GCAGGGGAAG GACGGCAGTG GGTAGCTGGG AGTGCTGGGC
1051  CGAAGATGGG CATTGTCAGG CCCTCAGTGG GGACTGGGAG GTAGAGGTGG
1101  GGAGGTCTGT GGAGGAAGGA GAAGAAGGGC CAGTGTCCCG AGTTGGGGGT
1151  GGTTGGCAGT GGACGAGGCC GACAGGAACA GACCTGAGCT TGGGGAGCTC
1201  CACTCAGAAC GAGGCATCCT TCAGGGTTCT GTGCATACTG GTGTCCCTGG
1251  CTGGGGCCG GGCCCCGAAG TGGAGCCTGG GACTGTGAGG GTGGGGGGG
1301  TGTGCTGGGG TGGGAGGTGG ATGGAGCCCC CCCTCTACCG CCTGGCCGCT
1351  TGGGCTGAAC CTTGGACTTC GGAGCCGGAA CAGACATAGG AAATGGCCTA
1401  ACTGCATTTG CGCAGGAACA CCAAATCCCT CGCAGCTGCA CGGGGCTGAG
1451  CCAGGGCCAC GGGCGGGGTC GGCCATCCCA GAGTCCTGAC AGCTCCGTGG
1501  TGTATGCCAA GGGGCTGGG CCGCTGACCG AGGGGCGCCT TTCCCAGGCC
1551  AGAGGCCCCC ACCCCACCCC AGGAGAGCTG CCCCCCTTTC AGTTCCAGA
1601  ACGGAGCTTG GCTGTGGAAT AGTGATGCGC TGAGGTCATG GGGAGGGGGC
1651  CCGGCATGACT CATATCCTGG GGTAGGGAA AGGGAGGAGA CGGAGAAGGG
1701  GCCCGAGAGGC CTCCACGTCC TCAGCTCTGC TGGGTCAGAG GCCAGGGGCT
1751  GGCGGGGCTT CTCCCCAGCA CTGGGTTTTA GGGGAGACAC CAGGAGATGC
1801  TTACTCTGCA TCCCCACTCT GTCCCCCAGG CCCCTAGCCA GGGAAAGCTC
1851  AGTCAGAGTG ATCCTCCAGG GGCCCAGCTC TGCATGGATG ATGTTCCCAG
1901  AGTACACACC TGGGCCTCGT GCCAGGGCCG GCACCGCCGT TGTCAGGGCT
1951  ATGGCAAGGC AAACAGTCAA TGTTTGCCTC ACTAAAGTGA GGCTGCAGCA
2001  CCCTGAAGGG ATCCCTGGAG GGGGACGTGG TCCCCTTGTT CCCAAGCTTG
2051  TCTGCACATG CACGTGGATG TCAAGGGTTC CCGTGTGTGA GCACATGCAT
2101  ATTTGTATGT GCATGGGGTG CGGGCATGTG TGCCTGTGTG GCCGGAGCGT
2151  GGGCTCGTGG AGAATGTGTG TGAGTTGGGT GTGCACCTGC ATGTGCCCA
2201  GGCCTAGAGA GTCAGGTGCC CGAATTG
```

FIG. 8B

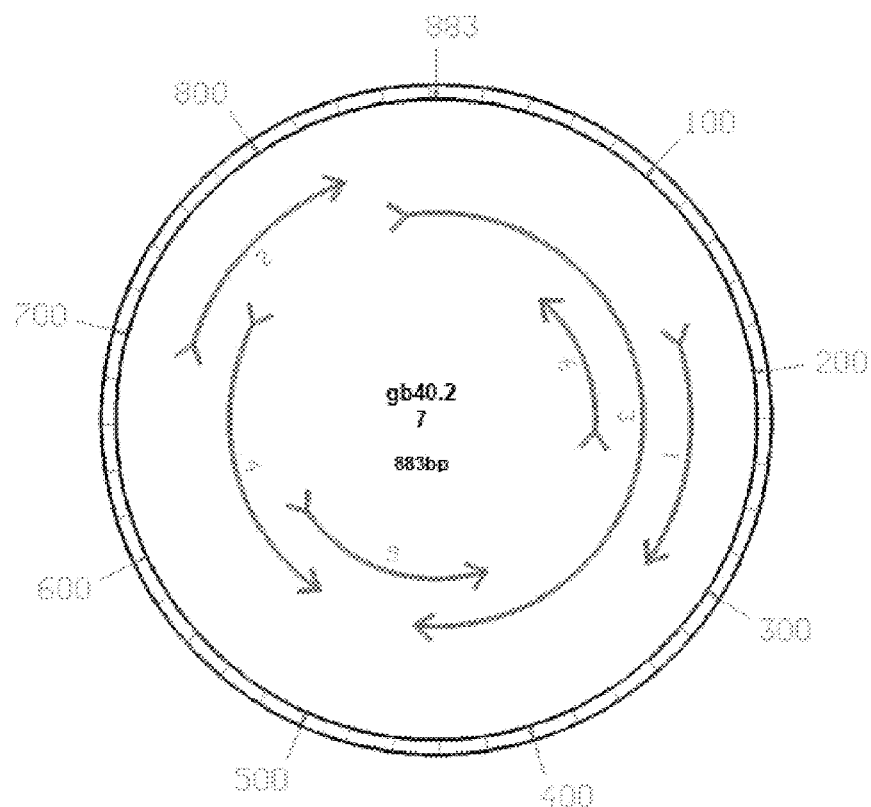

```
gb40.27
gbDfDg40.27.seq (zelluläre sequenz aus gb40 plus andere ms-hirn)
 Length: 883
long-pcr nach Templiphi
   primer: hel 1 + hel 2  ann 68 C (nested)
   vector: pcr2.1 invitrogen

1   CGGGACTGGC CGGGCTATGC CCCAGACACA CTCACGTAGG GGTGTCCGGC

51   CTGGCAGCCC AGGACCATGG TCTGCAGGGT TTCCTCTCGG CCATTCAGGA

101   CAATCCTAGT CTCCAGGGAA TAGCGCTGGT GTCGCCTATC AGCCGTGAAG

151   GTCTCCTGCA GGAGGAGGCT CTGCGGGATG GGCAGGTGCA ATGGGTGCCT

201   GGTGTGCAGA GGGAAAAACA GGCCAAAGCC ATTAAAGCAG CTGGCAGTGC

251   CAGGGGACAA TTGTGCCCCA CGGTCTCAGC CTGGGCCTGT CACGAGCTTG
```

FIG. 8B CONT'

```
301  CAGAGTTAAG ACTCTGCCAC AGAGAAGAGA ACATCAGGAC ACCTGGCAGC
351  CCTATGCTTT ACAATGTGGC ATCCAGAACC CTTCACCACC TCACTGTGCC
401  AGAGAAGTGG GCATGGCTGG GGTCCCCGTC GCCATTTGAC AGCAAAGACC
451  CAGAGGATA GATGACACAC AGCATCTGGT GTCACACAGA CTGGGATTAG
501  AATCCAGGCA CGGTCTTTCA CTAGCTGTGT GACCTTGGGA AAAGGACTTG
551  ACTGTTCTGT GCCTCAGTTT CCCCATCTGT AAAACGGAGG CTAAAATAAT
601  ACTGATCGGA CACAGTGGTC AGGGTTAGAG ATAACATACA TGAAACGACC
651  ACAAGCTCCC CAAGGGCAAA GGTTTCTGAC ATTCCGGTTC TCTGCCATTT
701  TCCATGTGCC CAGAAGAGCA CTTGGTCCAT AGTATGTGCT CAATGAATGT
751  AAATGGGATA AAAACACGAA CGAACACTCT GCCAACGATG CTGCTGTTCC
801  TTTGTCATCA CTGCTTCTGT TTAGGCTGTA GCTGACTTAT CTAAGGCCAT
851  ACAGCTGCTC AATGCATAGC CCGGCCAGTC CCG
```

FIG. 8C

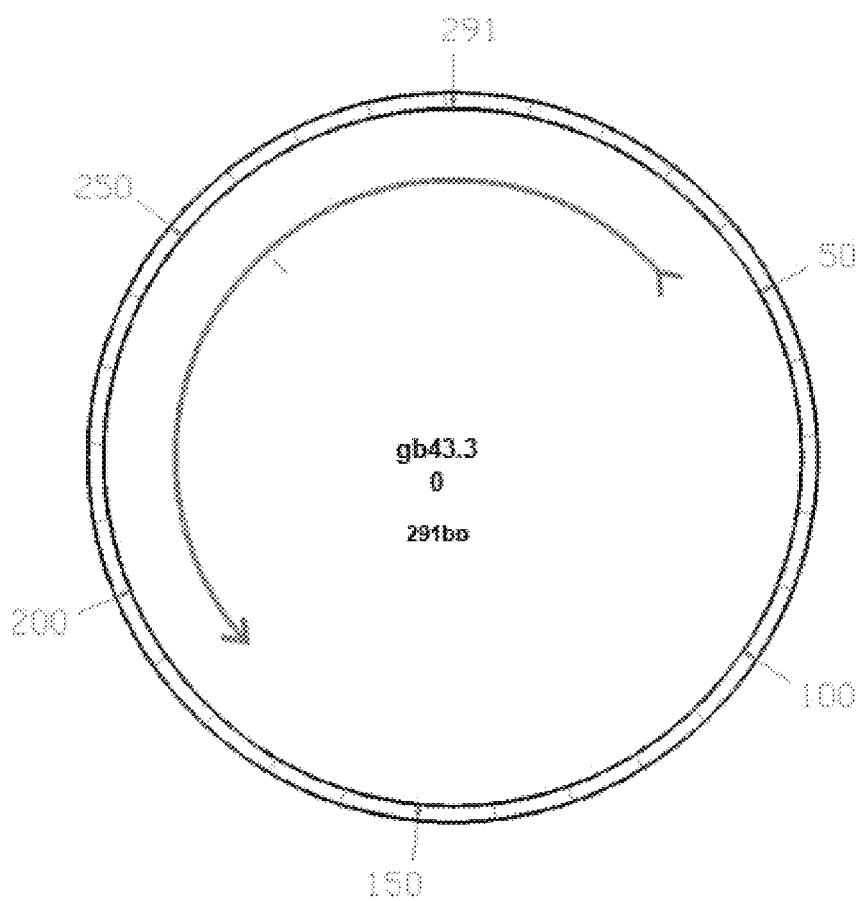

```
gb43.30
gbDhDi43.30.seq (zelluläre sequenz aus gb43 + andere ms-hirn)
Length: 291
long-pcr nach Temp.
primer: t3pb 1+2 ann.65%
Vektor: pCR2.1, Invitrogen 1  CCCCTTGACT TCGGTGTGTA AACTTGTGGT ATAGAACATG ATGTTTTAAG
   51  ATACATGTAC ATTGTGGAAT GGCTTGATCA TGCTAATTAA CATATGAATT
  101  ACCTCACTTA GCTATCTTTT TTATGGTGAA AGCACTTAAA ATCTACCCTC
  151  AGCAGTTTTC AAGTACACAA TACATTTCTA TTAACTATAG TCACCATGTT
  201  GTACAATAAA TCTCTTGAAT TTATTCCTCC TGCCTAACTG ACATTTTGTA
  251  TCCTTTGACT GATCTCTCTC CCCAGTCCCG TCCCGAATT G
```

FIG. 8C CONT'

Bold - primer sequence
Italic - continuation of cellular sequence

BLASTN2 of: /home/vir088/ttbrain/gbDhDi43_30.seq   from: 1 to: 291   June 9,
2010 12:21
compared to database: nrnuc >>>>nrnuc:GI_225543527 Gi|225543527|ref|NG_011635.1| Homo sapiens myosin
            IIIA (MYO3A), RefSeqGene on chromosome 10. 0/0
            Length = 285464

Score =  525 bits (265), Expect = e-146
 Identities = 268/269 (99%)
 Strand = Plus / Plus CCCTTGACTTCG
Query: 14       gtgtgtaaacttgtggtatagaacatgatgttttaagatacatgtacattgtggaatggc
73
                |||| |||||||||||||||||||||||||||||||||||||||||||||||||||||||
Sbjct: 276074   gtgtataaacttgtggtatagaacatgatgttttaagatacatgtacattgtggaatggc
276133
   TAATTGACAAAAC
Query: 74       ttgatcatgctaattaacatatgaattacctcacttagctatcttttttatggtgaaagc
133
                ||||||||||||||||||||||||||||||||||||||||||||||||||||||||||||
Sbjct: 276134   ttgatcatgctaattaacatatgaattacctcacttagctatcttttttatggtgaaagc
276193

Query: 134      acttaaaatctaccctcagcagttttcaagtacacaatacatttctattaactatagtca
193
                ||||||||||||||||||||||||||||||||||||||||||||||||||||||||||||
Sbjct: 276194   acttaaaatctaccctcagcagttttcaagtacacaatacatttctattaactatagtca
276253

Query: 194      ccatgttgtacaataaatctcttgaatttattcctcctgcctaactgacattttgtatcc
253
                ||||||||||||||||||||||||||||||||||||||||||||||||||||||||||||
Sbjct: 276254   ccatgttgtacaataaatctcttgaatttattcctcctgcctaactgacattttgtatcc
276313

Query: 254      tttgactgatctctctcccagtccgtg 282         CCCGAATTG
                |||||||||||||||||||||||||||
Sbjct: 276314   tttgactgatctctctcccagtccgtg 276342      ACCAGTGCCCT >>>>nrnuc:GI_14018255 Gi|14018255|emb|AL162503.12| Human DNA sequence
            from clone RP11-420F12 on chromosome 10 Contains the GAD2
            gene for glutamate decarboxylase 2 (pancreatic islets and
            brain 65kDa), the 3' end of the MYO3A gene for myosin IIIA
            and two CpG islands, ... 0/0
            Length = 176594

Score =  525 bits (265), Expect = e-146
 Identities = 268/269 (99%)
 Strand = Plus / Plus

FIG. 8C CONT'

```
Query: 14    gtgtgtaaacttgtggtatagaacatgatgttttaagatacatgtacattgtggaatggc
73
             ||||  |||||||||||||||||||||||||||||||||||||||||||||||||||||
Sbjct: 35112 gtgtataaacttgtggtatagaacatgatgttttaagatacatgtacattgtggaatggc
35171

Query: 74    ttgatcatgctaattaacatatgaattacctcacttagctatctttttatggtgaaagc
133
             ||||||||||||||||||||||||||||||||||||||||||||||||||||||||||||
Sbjct: 35172 ttgatcatgctaattaacatatgaattacctcacttagctatctttttatggtgaaagc
35231

Query: 134   acttaaatctaccctcagcagttttcaagtacaccatacatttctattaactatagtca
193
             ||||||||||||||||||||||||||||||||||||||||||||||||||||||||||||
Sbjct: 35232 acttaaatctaccctcagcagttttcaagtacaccatacatttctattaactatagtca
35291

Query: 194   ccatgttgtacaataaatctcttgaatttattcctcctgcctaactgacattttgtatcc
253
             ||||||||||||||||||||||||||||||||||||||||||||||||||||||||||||
Sbjct: 35292 ccatgttgtacaataaatctcttgaatttattcctcctgcctaactgacattttgtatcc
35351

Query: 254   tttgactgatctctctcccagtcccgtg 282
             ||||||||||||||||||||||||||||
Sbjct: 35352 tttgactgatctctctcccagtcccgtg 35380

Open reading frame: 49aa (Peptide) FASTA of: gbDhDi43.30rev.49.pep  from: 1 to: 49  June 9, 2010

REFORMAT of: gbDhDi43.30rev.49.pep  check: 3689  from: 1 to: 49  June 9,

TO: SwissProtPlus:*  Sequences: 11,223,768  Symbols: 3,635,054,084  Word
Size: 2

SPTREMBL:Q9WB12 9VIRU       Begin: 19  End: 68
! Q9wb12 SubName: Full=ORF2; Flags: F...    84   109   108   181.5    8.3
SPTREMBL:Q9WB09 9VIRU       Begin: 19  End: 54
! Q9wb09 SubName: Full=ORF2; Flags: F...    91    91   104   176.0    0.61
SPTREMBL:Q9WB02 9VIRU       Begin: 19  End: 59
! Q9wb02 SubName: Full=ORF2; Flags: F...    82    82   100   168.8    1.5
SPTREMBL:Q9WS94 9VIRU       Begin: 32  End: 73
! Q9wsw4 SubName: Full=ORF2; Flags: F...    82    82    97   162.5    3.4
SPTREMBL:Q9WAY4 9VIRU       Begin: 19  End: 54
! Q9way4 SubName: Full=ORF2; Flags: F...    84    84    94   160.8    4.2
SPTREMBL:Q9WB10 9VIRU       Begin: 19  End: 54
! Q9wb10 SubName: Full=ORF2; Flags: F...    84    84    94   160.1    4.6
SPTREMBL:Q9WAZ2 9VIRU       Begin: 19  End: 54
! Q9waz2 SubName: Full=ORF2; Flags: F...    84    84    94   160.1    4.6
SPTREMBL:O78807 9VIRU       Begin: 23  End: 58
! O78807 SubName: Full=Putative uncha...    84    84    94   158.2    5.3
```

FIG. 8C CONT'

```
\\End of List gbDhDi43.30rev.49.pep
SPTREMBL:Q9WB12_9VIRU

ID   Q9WB12_9VIRU            Unreviewed;       150 AA.
AC   Q9WB12;
DT   01-NOV-1999, integrated into UniProtKB/TrEMBL.
DT   01-NOV-1999, sequence version 1.
DT   09-FEB-2010, entry version 20.
DE   SubName: Full=ORF2; . . .

SCORES   Init1: 84   Initn: 109   Opt: 108   z-score: 181.5 E(): 0.3
>>SPTREMBL:Q9WB12_9VIRU                                   (150 aa)
 initn: 109 init1: 84 opt: 108 Z-score: 181.5 expect(): 0.3
Smith-Waterman score: 108;   53.5% identity in 43 aa overlap
 (6-46:19-60)

10         20         30         40
gbDhDi43.30r              MFYTTSLHTEVKGQFGHGTGERDQSKEIKCQ--LGRRNKFKRFIVQH
                               :::: ::::::: ::: :  ::: :  : ::: : :: : :
Q9WB12_9VIRU AQTQRRVIPASRGKVPEVSLHTKVKGQFGLGTG-RAMGKAIKKDMFLGKLYKKKRALSLH
                     10         20         30          40         50 gbDhDi43.30r GDYS
             |
Q9WB12_9VIRU GLRTPEAKPEAMSWRPPVHNPNRIEDNLWEASFRIHASSCGCGHLVGHLTVLARRYGAPP
             60         70         80         90        100        110

ID   Q9WB12_9VIRU            Unreviewed;       150 AA.
AC   Q9WB12;
DT   01-NOV-1999, integrated into UniProtKB/TrEMBL.
DT   01-NOV-1999, sequence version 1.
DT   09-FEB-2010, entry version 20.
DE   SubName: Full=ORF2;
DE   Flags: Fragment;
OS   Torque teno virus.
OC   Viruses; ssDNA viruses; Anelloviridae; unclassified Anelloviridae.
OX   NCBI_TaxID=68887;
RN   [1]
RP   NUCLEOTIDE SEQUENCE.
RC   TISSUE=Serum;
RX   MEDLINE=99336662; PubMed=10406852; DOI=10.1006/viro.1999.9797;
RA   Hijikata M., Takahashi K., Mishiro S.;
RT   "Complete circular DNA genome of a TT virus variant (isolate name
RT   SANBAN) and 44 partial ORF2 sequences implicating a great degree of
RT   diversity beyond genotypes.";
RL   Virology 260:17-22(1999).
CC   -----------------------------------------------------------------------
CC   Copyrighted by the UniProt Consortium, see
CC   http://www.uniprot.org/terms
CC   Distributed under the Creative Commons Attribution-NoDerivs License
CC   -----------------------------------------------------------------------
DR   EMBL; AB024879; BAA77446.1; -; Genomic_DNA.
DR   InterPro; IPR004119; Gyrovir_VP2/TT_ORF2.
DR   Pfam; PF02957; TT_ORF2; 1.
PE   4: Predicted;
FT   NON_TER       1       1
FT   NON_TER     150     150
```

FIG. 8C CONT'

```
SQ   SEQUENCE   150 AA;  16415 MW;  A4A7DF15855FC40D CRC64;
     AQTQRRVIPA SRGRVPEVSL HTKVKSQEGL GTGRAMSKAL KKDMFLGKLY KKKRALSLHG
     LRTPEAKPPA MSWRPPVHNP NRIERNLWEA FFRIHASSCG CGHLVGHLTV LARRYGAPPR
     PPAPGAPRPA LKRQLALPAP PADPQQANPT
```

FIG. 9A hodl1 hodL.VvWw.1.seq  Length: 639
Hodgkin L1236+TPA
PCR Primer: hlf1+Lr1 GCI 59°C
Vektor pGEM T-Easy

```
  1  CCCCTTGACT GCGGTGTGTA AAGCGCCCCA GCCTGTGCCT GCACAGTGCC

51  TGTGTGGTGT GAACCCATGA CCAGGCCTCT GGAGGGAAGG AAGGTTAGGC

101  TTAGTGGACA CCAGCTTTCC TAAGGTGGGT CTTAGACCAA CTCATTAAAA

151  TGGCAGGATG GGCTTTTGTG CTGTATTTCT TGGGATTTTC AAGATGCCCC

201  ACACAGCAGA AGGGATGTGC ATTTTTTTCT CTGCCCTGAG TTGTTTGATA

251  AAAATCAGTG ACCTCGTTCT CCACTTAGAA CTCCCCTGAA CTGCACTCGG

301  TGTCTAGGAC TGTTGGGGAA GGAAGTGAAG AGCCAGCATG TAGTCTCCTC

351  TGGACTCTTA CAGGATCTGT CCACCTCTGG GCTCTTTATG TAGGGGAAGG

401  TGTGAGCTCC TGGAGTACT CCTGATAGAG GACTGTTTCC CTGAAAACCT

451  CAGCAGTGTT TGAGGCCCTA GCAGGGGGAA CCCAGACCCC GCCTGCCAAA

501  GCCCCTAATC CCTCAGGGCT ATTATCAGCA GCCTAAGCGC CTTAGGGTGG

551  CCAGAGTCCA GCCCAGCAAG CAGCAAAGTC AGCAGCCTCC TCGCCCTATC

601  CTCTCCATGC CCCGGGGCAC TCCAGTCCCG ACCGAATTG
```

Primers in bold
Continuation of cellular sequence in italics

```
BLASTN2 of: /home/vir088/ttmixture/hodL.VvWw.1.seq   from: 1 to: 639
compared to database: nrnuc    ..
Database: nrnuc
>>>nrnuc:GI_18121492  Gi|18121492|emb|AL513485.10| Human DNA sequ...    690    0.0
>>>nrnuc:GI_149944898 Gi|149944898|gb|AC198797.3| MACACA MULATTA...     509    e-141
>>>nrnuc:GI_55416061  Gi|55416061|gb|AC121551.11| Mus musculus ch...     84    1e-12
>>>nrnuc:GI_241752248 Gi|241752248|ref|XM_002400984.1| Ixodes sc...      46    0.26
>>>nrnuc:GI_291191454 Gi|291191454|gb|GU722348.1| Torque teno vi...      44    1.0
>>>nrnuc:GI_291191453 Gi|291191453|gb|GU722347.1| Torque teno vi...      44    1.0
>>>nrnuc:GI_291191452 Gi|291191452|gb|GU722346.1| Torque teno vi...      44    1.0
>>>nrnuc:GI_217416834 Gi|217416834|gb|FJ426280.1| Torque teno vi...      44    1.0

>>>nrnuc:GI_18121492 Gi|18121492|emb|AL513485.10| Human DNA sequence
          from clone RP11-48O20 on chromosome 1 Contains the TAGLN2
          gene for transgelin 2, the IGSF9 gene for immunoglobulin
          superfamily member 9, the SLAMF9 gene for SLAM family
          member 9, a novel gene and . . . 0/0
       Length = 80398
```

FIG. 9A Cont'

```
Score =  690 bits (348), Expect = 0.0
Identities = 348/348 (100%)
Strand = Plus / Plus Query: 282   tcccctgaactgcactcggtgtctaggactgttggggaaggaagtgaagagccagcatgt 341
             ||||||||||||||||||||||||||||||||||||||||||||||||||||||||||||
Sbjct: 26212 tcccctgaactgcactcggtgtctaggactgttggggaaggaagtgaagagccagcatgt 26271

Query: 342   agtctcctctggactcttacaggatctgtccacctctgggctctttatgtaggggaaggt 401
             ||||||||||||||||||||||||||||||||||||||||||||||||||||||||||||
Sbjct: 26272 agtctcctctggactcttacaggatctgtccacctctgggctctttatgtaggggaaggt 26331

Query: 402   gtgagctcctgggagtactcctgatagaggactgtttccctgaaaacctcagcagtgttt 461
             ||||||||||||||||||||||||||||||||||||||||||||||||||||||||||||
Sbjct: 26332 gtgagctcctgggagtactcctgatagaggactgtttccctgaaaacctcagcagtgttt 26391

Query: 462   gaggccctagcagggggaacccagaccccgcctgccaaagcccctaatccctcagggcta 521
             ||||||||||||||||||||||||||||||||||||||||||||||||||||||||||||
Sbjct: 26392 gaggccctagcagggggaacccagaccccgcctgccaaagcccctaatccctcagggcta 26451

Query: 522   ttatcagcagcctaagcgccttagggtggccagagtccagcccagcaagcagcaaagtca 581
             ||||||||||||||||||||||||||||||||||||||||||||||||||||||||||||
Sbjct: 26452 ttatcagcagcctaagcgccttagggtggccagagtccagcccagcaagcagcaaagtca 26511

Query: 582   gcagcctcctcgccctatcctctccatgccccggggcactccagtccc 629    GACCGAATTG
             ||||||||||||||||||||||||||||||||||||||||||||||||
Sbjct: 26512 gcagcctcctcgccctatcctctccatgccccggggcactccagtccc 26559  AGCTGGCTGATC Score =  505 bits (255), Expect = e-140
Identities = 272/280 (97%)
Strand = Plus / Minus CCCCTTGA
Query: 9     ctgcggtgtgtaaagcgccccagcctgtgcctgcacagtgcctgtgtggtgtgaacccat 68
             |||| |||||||||||||||||||||||||||||||||||||||||||||||||||||||
Sbjct: 29128 ctgctgtgtgtaaagcgccccagcctgtgcctgcacagtgcctgtgtggtgtgaacccat 29069
        TTCAGTTAG Query: 69    gaccaggcctctggagggaaggaaggttaggcttagtggacaccagctttcctaaggtgg 128
             ||||||||||||||||||||||||||||||||||||||||||||||||||||||||||||
Sbjct: 29068 gaccaggcctctggagggaaggaaggttaggcttagtggacaccagctttcctaaggtgg 29009

Query: 129   gtcttagaccaactcattaaaatggcaggatgggcttttgtgctgtatttcttgggattt 188
             ||||||||||||||||||||||||||||||||||||||||||||||||||||||||||||
Sbjct: 29008 gtcttagaccaactcattaaaatggcaggatgggcttttgtgctgtatttcttgggattt 28949

Query: 189   tcaagatgcccacacagcagaagggatgtgcannnnnnnnctctgccctgagttgtttga 248
             |||||||||||||||||||||||||||||||||        ||||||||||||||||||
Sbjct: 28948 tcaagatgcccacacagcagaagggatgtgcatttttttctctgccctgagttgtttga 28889

Query: 249   taaaaatcagtgacctcgttctccacttagaactcccctg 288
             ||||||||||||||||||||||||||||||||||||||||
Sbjct: 28888 taaaaatcagtgacctcgttctccacttagaactcccctg 28849
```

FIG. 9B hoht33
hoHT.vAf.33a.seq Length: 3387
Lymphom HSB+TPA, Templiphi-RCA
PCR-Primer HLF1+Hr4 60°C
Vector pCR2.1

```
   1 AATTCGGTCG GGACTGGCAG AGTGACGCTC AGGTCAGCCT GACAGCAGGG
  51 TGATTGAAGG GGCCAGATAC CCCAGCAGGG CCTGAGGCCA GAACACAGCA
 101 TAGGCTGGCT CTGATGGGTG GAGGAGGTGG CCAGGCATCA TCTGGAGCTT
 151 GGAGTTGAGA ACATCTGTGA CTCCTCCTTC AGGAGGGTGC TCTAGGAGTT
 201 GAGAGCATCC TAGGTAGGAC CATACATCTA CCCCCATCCT AGTTCCCTCC
 251 AGCCTCTCTT TTCAGCTCCA GGTCTACCTT AAGGGACCTA GGACACCTGG
 301 GCTGGGGCAT AACAGGACTT GGTTTTATGT AAAGGAGCTG GGAAGAGACT
 351 GAGATAACAG AGGGCTGCAA GGAGAGAGAC AGAGAGAGAA GAACCTGCCA
 401 GAAGAAGCTC CTCAGCAATC CACTAAGCCC TGATCTTTGC CTCACTGCCT
 451 GTCCCTTCCC ATCCGCTCTT CTGCTCTCTC AATCTCTGCC TTCAAGAAAT
 501 TTGGTGCATA TTGGAATAGG GAGGAATAGA AGCACCCTGG GTGGAGCTCT
 551 GGGCTTGGCT GTGCACGAGC TTTCAGTGGG TGGTTTGCTG GTCTCCAAAG
 601 ATGACCCTCC ATTAGTCATG CTTCTCGGTG TTTGTCCTCA GGTAGTCTCA
 651 TCCCATCTTG AGTCTGGGCT TGCCCTGTGA CTCACTTTAA CCACAAGAAT
 701 GTGGCAGAAA GGATGTTGTG CCAGTTCTAG AACTAAGCCT TCAGAAAGCC
 751 TAGCACCTTC TGCTTTTAGG AGCACTGAGC CCCCATGTTA GAAGTCCACT
 801 TTTATACTCT GCTCTGGAGA CTAGCAGAAT TAGAAATGCA CTGCTGAATG
 851 CTGCTCGAGA GACTAATGGA GAGGCCATGT GAATAAGGAG GCCTGAAACT
 901 ACATGGAGAT AGAGGGCCAG CCACCCCAGC ACCACGGCTC AGCTGTGCCT
 951 CCCAGCCATC TCTGCCAGTC CTCCAGGGCT ATGAGTGAAC CATCTTGGAT
1001 GTTCTAGCTC GGTGGAGCCC CCAGGTGATT GCAGCCTCAG CCACCATCTG
1051 ACTGTAGCTG CATGAGAGGC CCCCAGTGGG ACCAGCAGGA CTGCCAAGCT
1101 GAGCCCTGCC CACCCACAGA ACTGTGAGAA ATAAAAAAAT GGTTGTTTCC
1151 TTAAGCCATT AAGTTTTGGA ATGATTTGTT ACTCACAATT GATAACTGAT
1201 ACAGTCTGTC TTTAGGGAAA ACAAGGGATA ACTCTGGGCT CCAGGTCTCT
1251 TCTATAGGAT GAATGGGACT TGGTTGCTGA CAAGCTGACA AGTTTGAGCA
1301 TGAAACTCTT TTTTTTTTTT GGAGAAGGAA TTTTGCTCTT GTTATCCAGG
1351 CTGGAATACA GTGGTGCGAT CTCGGCCCAA GGCAACCTCT GCCTCCTGGG
1401 TTCAAGCAAT TCTCCTGCCT CAGCCTCCTG AGTAGCTGGG ATTACAGGCA
1451 CCCACCACTA CACCTGGCTC TTTTTTTTTT TTGTATTTTT AGTAGAGACA
1501 GGTTTTCATT ATGTTGGCCT GGTCAGGTTT TGAACTCCTG ACCTCAGGTG
1551 ATCCACCTGC CTTGGCCTCC TAAAATGCTG GGATTACAGG TGTGAGCCAC
```

FIG. 9B Cont'

```
1601  CGTGCCTGGC CTGAGCATGA AACTTTTATG CTCAAACATT AAAGTGTAAA
1651  CACTCACCAG CTCAGCTGAA TAAGAACTTC TGGGGGCAAG GCCCAGGAAT
1701  CTACAGTTTA GTAAGTGCCC CCACCACTGG ACCCTGGGAA AGTGGACTGC
1751  ATTTTGAAAA ACTCTAGATC AGTTGATACC CAGGAGTCCT CATAACACTA
1801  AGTTGTAATA CCTCAGTGTG AATTAGTCTG ATGCAGCTCT TCTTAGAGGT
1851  CATTGACAGA GGGCAAGACA TTTCCAAAAG GAAGGAATAG CCAATATGGA
1901  ATGACAGGTG GATTGGATGA CCCTCTATTA TTTAGTTTCA ACCTGCCCTT
1951  CCTGCCTTCC CTCCCACAAA TTCCCTTTCA GATCCTCCGT CCTAATCCTC
2001  TTCGATAGTT CATTGTTCTT CTGCAGACAG AGCAGCGAAG TGTTATCTGT
2051  TGTACCCACT ATGACTAGTT GATGGTGCAT GGCTTCCATG GAGCAGTGCT
2101  GTGATCCATT AGTCATGGAG CAGTGCTGTG ATCCATTGTC ATGTCTGCCA
2151  TGAACACTGG AAGGGGCAGT GGTAATGACA GCCTCTTACA TTTGCCAACT
2201  CTGCCCAACA TTCTTCCCAG TGTTGGGAAA GCCTTTGCTT ATTCCATTCC
2251  TTCTTGGAAA GCTTTGTTCC TCCATTTCAC ATTTTTAATT TTTCTCATTT
2301  TTATGGTGCA CCATGGATAC CACCTGTCCA TATAGCTGGC TTCTGATTTT
2351  TCCAGATGAA AGTAATCCTT CCTCTCCTAA CCTCCCATGA CACCTAACCT
2401  GGCACTCATT TACGGTGTTC AGCTCCTTCT CCTGTACGTT CTCATTGTTC
2451  TCCTCTCATC TTCTCCCCAG GAATGGATTC CCCGCCAAGG GAGGTACCAG
2501  GTCAGTTTCT TCTTTGTGCA ACAGGGTGTC CCTGATGAGC ACAAACCTGG
2551  AACAAGTGTT TGTAGGGCTG GTGGGCATCT GGTTCCTCTG GGTGTTGTGT
2601  AGCCTGAGCC GGGGGGCAAA TGGGTGTTTG TTTTTCTGAA GAAGGCAGGC
2651  GTTCTGTGGC AGATGTGGGT GGAGGGGGTT GGGGAGTAGT ATCATGGAGA
2701  GGCTGGGATC CTATCTATCT CCTTCCCCTG CTTGAAGGGC AACTTGGGAG
2751  AAGCTCAAGA GGGAGGAGTT GACTGCAGAA GCTGGGATAC CTGCATAACT
2801  CTCAGGTTCA AGCATCACTG CTTTAGGGCC CTGGGGCCT ATGTGTGAGT
2851  CAAGAAAGGG AGATAGAGAG AGAAGAGAGA GAGAGGAGAG AGAGAGAGAG
2901  AGAGAGAAGA CAGAGGAGAG AGAGAGAGAA GAAAGAGGAG AGAGAGAGAA
2951  GAGAGAGCAG AGAGAGAGAG CATGCTGTCA GTGAGGTGGC CCTAAGCCCT
3001  CTTGGAAATA ACTTGGAGGC ACTGTGGGGT GGCTCTGAGG TGCTGAGGTA
3051  TACCTGTAGT GGGGCTAGGA CCTTTCCAAC CTGGGTCTGA AGGTTGAGGC
3101  AACCTTGGGT GTACCTGCTG GTGAGCTGAG AGCCCTGGGG ACCTTTGGCA
3151  GACATTCCCA CCCCTGCAGC CTGGAGGGTT TGCATGCAGT GAGGCTGTCC
3201  TGCTCATCAC TACGTCCTCT GGGACAGCAC ATTGCCTGTG CTGAACAGGC
3251  ATTCAGTTGC GATTTGTGGA ATCAGTGTTG GTGAGGAGGG CAAGTGGCAA
3301  CAGAAATGGG GGTGTGCTCC CCCCAGTTCC TCAGCTACAA TCTCCATGAC
3351  CTTCTACACT GCCCTGGGCC CAGTCCCGAC CGAATTG
```

FIG. 9C

```
hoht22
hoHT.vAf.22a.seq Length: 1790
Lymphom HSB+TPA, Templiphi-RCA
PCR-Primer HLF1+Hr4 60°C
Vector pCR2.1

1  CAATTCGGTC GGGACTGGGG AGCTGTGAGA AAGAGAAGAG AAGGTCAGAT
  51  CAGGAACATT ACACAGAAGT CGGCAAAACT GGAACGAGGA GGGAAAGAAA
 101  TGAGCGAGTC TGACACTCAG TCCATCCTAG TTCCTATCAC ACAGGGAGGG
 151  ACATTGCCAT GCACATCCCC ACAGAGATGC ACCGTGTAAG GGGTCGAGGC
 201  AGATCCTGTC CACTATTGCC AGCTCTGAGG TGATCAAATT GTGTCTGCCC
 251  AGGGTAACCC GGTTGACCTA AACCAACCCA CTCCCTTGCA CATCTTAGGT
 301  GTTCCTGAGT CAGCAAGGCT GAGGAAGCCA CTCCAGCCAA AATCCCTTGT
 351  GCGATCTTCA AGCCCCAATC ACAGGCAATG ACAAGGCCAT GTCTGGCTGG
 401  CCTCATGGGG ACTGCCCTCC CCTCACCAGA CCTAGAACAC AGGCAATGCT
 451  CAGCAGCGTT CTGAGAAGAG CTGAGGTCAA GAACTCCAAC CCCACGCAAC
 501  CCAGACCTGA TACAAACAGA CACCCATTTG CACTCCTAAC CCTTGAGCCT
 551  CTATTTCCAG ACCTCCTCAC TGGGTCTCAG CTGAGAACCC ACTTTTAGCC
 601  AAGCATCTTT AGTTCAGAGT TCCTCGCAGT GAGGGGATCC CTCCCCTGCC
 651  TTGCTGTCTG TGCTGCATCC ATTATACCCT CACACCGTGC TACTCAGCAG
 701  GGGAGAAATG GAGCCCTGGG GAGCCGGCAC TTTTCTCTTC TGCCTCTTCC
 751  TTGCCTTGCC TCAGGAAGGG GAAAAACTCT GGGTTGTTTT AGTTTGATCC
 801  CCTGTCCTAA GTGACCACAG GAACACTAGG CAGTGAGTAC ATATGGATTC
 851  TTAGCAGAGA GCTGACAAGT CTTCAGAAAC ATAGAAAACA TAGAAGCTTT
 901  GAGTGAGGAG ATCAGAATGT AATTAGGAGT TTCTTTTGGA GCAAACCCCA
 951  CCCCAAGAGA GTGAGCCCAA GTTCTTGAAG GCCCACCTGA GCAGATGACA
1001  CCAGCGTCTT CACTATGGCC ACAGTTGTGG GTGAGCCAGC CATTGTGGGG
1051  GCAGCTCCAC AGGTAGGACT CGTGTCCTGA GCAGCGCACA TCATCCAGGA
1101  CAATGGGTCC TGAGCCCTGG CCAAACTGGG CATTTCCTGG GGCTGACATG
1151  GCCCAGCCAC AGCCCGGCTG CCTGCAGACC ACATTGGCAT CATTGGTGTC
1201  CCAGTAGTCA TCACACACGG TGCCCCAGGA GCCTCGGTAT AGGACCTCCA
1251  CTCGGCCTCG ACACCTGTCG CCTCCATTCA CCAGCCTCAG GGCCAAACTG
1301  GATTCAGATC CTACAGGGGA ACACAAGAAC CTTTCATCCA TCCCTATCAT
1351  GAGGTCAAGA ATCTAAGGTA AGTTCCACAC TCAGGGTACT TCCTAATGAA
1401  CTAAGTCACC TAGGCAGGCA GTCACCTTTG CATATGACTA CAGACTAGGC
1451  TTCATCACCG TGAAAGTAGC ACTGATAACC TACTCTGCCC AGGTCTATGG
1501  GTGCTCAACT TTTGGGGAAG CACCTGTGAC CCCAGTGGAT GTGATGGGAA
1551  TGGATGCCCC ACTCCCCAGT TGGGTACACA GAGGATGGAG CTGCTCAGCT
1601  CCAGATGGCA GGCCCAGACC CCTCCCTTAT TCAGGAGCAT GGTCCTATCT
1651  GGGATCTGAC TGGCAGAGTA CCAGAGATGG CAGGGATGAG GTCCCCATAG
1701  GATTAGGGAG ACCCCCAGGG CTTGTTCTGA GCCCATAGAT AAGGATCTTT
1751  TCTGACCACT TGGAACAGGA TCCCAGTCCC GACCGAATTG
```

FIG. 10

```
DhDi:
t3pb-1.prime   Length: 18   long-pcr primer forward
     1  caattcgggc acgggact t3pb-2.prime   Length: 24   long-pcr primer reverse
     1  ccccttgact tcggtgtgta aact cd:
tth4prime1.seq  Length: 28 long pcr primer forward back-to-back with prime2
     1  CAGCGAGAAC GCCACGGAGG GAGATCCT tth4prime2.seq  Length: 28 long pcr primer reverse back to back with prime1
     1  CGGACGGGCG TGGAAAACTC AGCCATTC DfDg:
hel32-1.prime   Length: 18   long-pcr primer forward
     1  cgggactggc cgggctat hel32-2.prime   Length: 19   long-pcr primer reverse
     1  agcccgaatt gccccttga
```

FIG. 11A

```
ttgb33.35
gbDhDi33.35.seq (complete genome from ms-biopsy)
long-pcr, Templiphi
 primer: T3PB 1 + T3PB 2    ann.:65 C
 vector:TA-cloning  pCR2.1  invitrogen Length: 3725
       1  ATTTTGTGCA GCCCGCCAAT TTCTGTTCAA ACAGACCAAT CAGGACCTTC
      51  TACGTGCACT TCCTGGGGCG TGTCTACGAG GTCTATATAA GCAACAGCGG
     101  TGACGAATGG TAGAGTTTTT CTTCGCCCGT CCGCGGCGAG AGCGCGAGCG
     151  AAGCGAGCGA TCGAGCGTCC CGTGGGCGGG TGCCGTAGGT GAGTTTACAC
     201  ACCGAAGTCA AGGGGCAATT CGGGCACGGG ACTGGCCGGG CTATGGGCAA
     251  GGCTCTTAAA AAATTCCCCC GCTCTGCTCT CCGGCAGGAC ACAAAGTCAT
     301  GCCGTGGAGA CCGCCGGTCC ATAACGTGCC AGGTAGAGAG AATCAATGGT
     351  TTGCAGCGTT CTTTCACGGT CATGCTGCTT TCTGCGGGTG TGGTGACCCT
     401  GTTGGGCATC TTAACGGCAT TGCTCCTCGC TTTCCTAACG CCGGTCCACC
     451  GAGACCACCT CCAGGGCTAG ACCAGCTTAA TCCCGAGGGC CCGGCAGGTC
     501  CCGGAGGGCC CCCCGCCATC TTGCCAGCTC TGCCGGCCCC GGCAGACCCT
     551  GAACCGGCAC CACGGCGTGG TGGTGGGGCA GATGGAGGCG CCGCCGCTGG
     601  GGCCGCCGCC GACGCAGACC ATACCGGGTA CGAAGAAGGA GACCTAGAAG
     651  ATCTTTTCGC CGCCGCGGCC GAGGACGATA TGTGAGTAGG CGGAGGCGCC
     701  GCCGCTACTA CAGGCGCAGA CTGAGACGGG GCAGACGCAG AGGGCGACGA
     751  AAGAGACACA GACAGACTCT AGTAGTGAGG CAGTGGCAAC CTGACGTTGT
     801  TAAAAAGTGT AAAATAACAG GATGGATGCC TCTTATAATC TGTGGCTCTG
     851  GAAGCACACA GATGAACTTT ATAACTCACA TGGACGATAC TCCCCCTATG
     901  GGATACACCT ACGGGGGCAA CTTTGTAAAT GTAACTTTCA GTCTAGAGGC
     951  CATCTATGAA CAATTCCTGT ACCACAGAAA CAGGTGGTCC AGGTCTAACC
    1001  ATGACTTAGA CCTGGCCAGA TACCAAGGAA CCACTCTAAA ACTTTACAGA
    1051  CACCAAACCG TGGACTATAT AGTTAGCTAC AACAGAACAG GCCCCTTTAC
    1101  TATAAGTGAA ATGACTTACA TGAGCACACA CCCGGCTCTC ATGCTACTAC
    1151  AAAAACATAG AATAGTTGTA CCCAGCTTCA GAACCAAGCC AAAAGGCAAA
    1201  AGAGCCATAA AAATTAGAAT AAGGGCCCCA AAACTAATGC TCACCAAGTG
    1251  GTACTTTACA AAAGACATTT GCTCCATGGG CCTCTTTCAA CTAATGGCAA
    1301  CAGCTGCAGA ACTTACAAAC CCATGGCTCA GAGACACCAC AAAAAGCCCA
    1351  GTAATTGGCT TCAGAGTCTT AAAAAACAGC TTATACACAT GCCTTTCCAA
    1401  CTTAAAAGAC CAAGCAATAC AAGGTGAAAG AAAGACTGTA CAAAATAGAT
```

FIG. 11A Cont'

```
1451  TACACCCAGA AAACCTACAT GGCACAGGAC CTAATGCTAA AGGCTGGGAA
1501  TACACATACA CAAAACTAAT GGCATCTACA TACTACTCAG CCAACAGAAA
1551  CAGCACCTAC AACTGGCAAA ACTATCAAAC TAACTATGCA AACACATATA
1601  CAAAATTTAA AGAAAAAGA ACAGCAAACT TAAACTTAAT TAAAGCAGAA
1651  TACCTATATC ATTACCCTAA CAATGTCACA CAATCTGACT TTATATTAGA
1701  CTACACACTA ACACCCGACT GGGGCATATA CAGCCCCTAC TACCTAACAC
1751  CCACCAGAAT TAGCCTAGAC TGGGACACAC CATGGACATA TGTAAGATAC
1801  AACCCACTAT CAGACAAAGG CATAGGTAAC AGAATATATG CACAGTGGTG
1851  CTCAGAAAAA TCTAGTAAAT TAGACACCAC AAAGAGCAAG TGCATACTAA
1901  GAGACTTCCC ACTGTGGGCC ATGGCCTATG GCTACTGTGA CTGGGTGGTG
1951  AAGTGCACAG GAGTGTCCAG TGCTTGGACA GACATGAGAA TAGCCATTAT
2001  ATGTCCCTAC ACAGAACCAG CACTTATAGG GTCAACAGAA GACGTAGGCT
2051  TCATTCCAGT AAGTGACACC TTTTGCAACG GAGACATGCC GTTTCTTGCA
2101  CCATACATAC CTATTACATG GTGGATTAAG TGGTACCCCA TGATTACACA
2151  CCAAAAGGAA GTTCTTGAGG CAATAGTTAA CTGTGGACCG TTTGTACCCC
2201  GAGACCAAAC TTCCCCAGCT TGGGAATAAC CATGGGTTAC AAAATGGATT
2251  GGAAATGGGG CGGCTCTCCC CTGCCTTCAC AGGCAATCGA CGACCCCTGC
2301  CAGAAGTCCA CCCACGAACT TCCCGACCCC GATAGACACC CTCGCATGTT
2351  ACAAGTCTCT GACCCGACAA AGCTCGGACC GAAGACAGTT TTTCACAAAT
2401  GGGACTGGAG ACGTGGGATG CTTAGCAAAA GAAGTATTAA AAGAGTCCAA
2451  GAAGACTCAA CAGACGATGA ATATGTTGCA GGACCCTTAC CAAGAAAAAG
2501  AAACAAGTTC GATACTCGAG TCCAAGGCCC TCCAACCCCA GAAAAAGAAA
2551  GTTACACTTT ACTCCAAGCC CTCCAAGAGT CGGGGCAAGA GAGCAGCTCA
2601  GAGGACCAAG AACAAGCACC CCAAGAAAAA GAGGACCAGA AGGAAGCGCT
2651  CATGGAGCAG CTCCAGCTCC AGAAACACCA CCAGCGAGTC CTCAAGCGAG
2701  GCCTCAAACT CCTCCTCGGA GACGTGCTCC GACTCCGGAG AGGAGTCCAC
2751  TGGGACCCCC TCCTGTCCTA ATTCAAGGTC CCAGTATCCC AGACCTGCTT
2801  TTCCCTAACA CACAAAAAAA AAAACGATTT TCCAACTACG ACTGGGTGTG
2851  CGAGTACGAG CTGGCCAAAT GGATGGATCG GCCCTTGCGG CACTACCCAT
2901  CAGACCCCCC TCACTACCCC TGGCTACCAA AAAAGCCTCC TACCCCTCCT
2951  ACATGTAGAG TAAGTTTCAA ATTAAAGCTC AATGACTAAA ATTCAAGGCC
3001  GTGGGTGTTT CACTTCATCG GTGTCTACCT CTAAAAGTCA CTAAGCACTC
3051  CGAGCGTAAG CGAGGAGTGC GACCCCCCTG CCCGGTAGCA ACTTCCTCGG
3101  GGTCCGGCGC TACGCCTTCG GCTGCGCCGG GCGCCTCGGA CCCCCCCTCG
3151  ACCCGAATCG CTCGCGCGAT TCGGACCTGC GGCCTCGGGG GGGTCGGGGG
3201  CTTTACTAAA CAGACTCTGA GGTGCCGTTG GACACTGAGG GGGTGAACAG
3251  CAACGAAAGT GAGTGGGGCC AAACTTCGCC ATAAGGCCTT TAACTTTGGG
3301  TCGCTTGTCA GCAGCTTCCG GGTCCGCCTG GAGGCCGCCA TTTTACATTC
3351  GGCCGCCATT TTAGGCCCTC GCGGGCCTCC ATAGTCGCAC ATCAGTGACG
```

FIG. 11A Cont'

```
3401  TCACGGCAGC CATCTTGGCT GTGACGTCAA CGTCACGTGG GGAGGACGGC
3451  GTGTAACCCG GAAGTCATCC TCATCACGCG ACCTGACGTC ACGGCCGCCA
3501  TTTTGTGCTG TCCGCCATCT TGTGACTTCC TTCCGCTTTT TGTAAAAAAA
3551  AGAGGAAGTG TGACGTAGCG GCGGGGGGGn nnnnnnnnn nnnnnnnCGC
3601  CACCAGGGGG CGCTACGCGC CCCCCCCGC GCATGTGCGG GTCCCCCCCC
3651  TCGGGGGGGG CTCCGCCCCC CCGGCCCCCC CCCGGGCTAA ATACACCGCG
3701  CATGCGCGGC CACGCCCCCG CCGCC
```

FIG. 11B zpr4.20
zpr4.20.seq (subviral molecule, ttgb33.35)
 293TT +4 (gbDhDi33.35) PCR
Tr9.7 A/9nested B5 in pCR2.1, Nova Blue zpr4.B5.20.seq   Length: 719

```
  1  CAATTCGGGC ACGGGACTGG CCGGGCTATG GGCAAGGCTC TTAAAAAATT
 51  CCCCCGCTCT GCTCTCCGGC AGGACACAAA GTCATGCCGT GGAGACCGCC
101  GGTCCATAAC GTGCCAGGTA GAGAGAATCA ATGGTTTGCA GCGTTCTTTC
151  ACGGTCATGC TGCTTTCTGC GGGTGTGGTG ACCCTGTTGG GCATCTTAAC
201  GGCATTGCTC CTCGCTTTCC TAACGCCGGT CCACCGAGAC CACCTCCAGG
251  GCTAGACCAG CTTAATCCCG AGGGCCCGGC AGGTCCCGGA GGGCCCCCCG
301  CCATCTTGCC AGCTCTGCCG GCCCCGGCAG ACCCTGAACC GGCACCACGG
351  CGTGGTGGTG GGGCAGATGG AGGCGCCGCC GCTGGGGCCG CCGCCGACGC
401  AGACCATACC GGGTACGAAG AAGGAGACCT CGGGGGGGGC TCCGCCCCCC
451  CGGCCCCCCC CCGGGCTAAA TACACCGCGC ATGCGCGGCC ACGCCCCCGC
501  CGCCATTTTG TGCAGCCCGC CAATTTCTGT TCAAACAGAC CAATCAGGAC
551  CTTCTACGTG CACTTCCTGG GGCGTGTCTA CGAGGTCTAT ATAAGCAACA
601  GCGGTGACGA ATGGTAGAGT TTTTCTTCGC CCGTCCGCGG CGAGAGCGCG
651  AGCGAAGCGA GCGATCGAGC GTCCCGTGGG CGGGTGCCGT AGGTGAGTTT
701  ACACACCGAA GTCAAGGGG
```

FIG. 12A

```
tth25 (complete genome)
length 3758

1  AAGTACGTCA CTAACCACGT GACTCCCGCA GGCCAACCAG AGTCTACGTC
   51  GTGCACTTCC TGGGCATGGT CTACATCATA ATATAAGAAC GTGCACTTCC
  101  GAATGGCTGA GTTTTCCACG CCCGTCCGCA GCGAGAACGC CACGGAGGGA
  151  GATCCTCGCG TCCCGAGGGC GGGTGCCGGA GGTGAGTTTA CACACCGCAG
  201  TCAAGGGCA  ATTCGGGCTC GGGACTGGCC GGGCCCGGG  CAAGGCTCTT
  251  AAAAAATGCG TTTTCGCAGG GTTGCCCAGA AAAGGAAAGT GCTTTTGCAA
  301  ACTGTGCCAG CTGCAAAGAA GGCTAGGCGG CTTCTAGGTA TGTGGCAGCC
  351  CCCCACGCAC AATGTCCCGG GCATCGAGAG AAACTGGTAC GAGAGCTGTT
  401  TTAGATCCCA CGCTGCTGTT TGTGGCTGTG GCGATTTTGT TGGCCATCTT
  451  AATCATCTGG CAACTACTCT GGGTCGTCCT CCGCGTCCTG GGCCCCCAGG
  501  CGGACCCCGC ACGCCGCAAA TAAGAAACCT GCCAGCGCTC CCGGCGCCCC
  551  AGGGCGAGCC CGGTGACAGA GCGCCATGGC ATGGGCTTC  TGGGGCCGAC
  601  GCCGCCGGTG GAGACGATGG AGAGCGCGGC GCAGACGGTG GAGACCCCGC
  651  AGACGTAGGA GACGACGCCC TACTCGCCGC TTTCGAGCTC GTCGAAGAGT
  701  AAGGAGGCGC GGGGGGAGGT GGCGCAGACG CTACAGAAAA TGGCGACGGG
  751  GCAGACGCAG ACGGACTCAT AGAAAAAAGA TAGTCATAAA ACAGTGGCAA
  801  CCAAACTTTA TAAGACGCTG CTACGTCATA GGGTACTTAC CACTTATATT
  851  CTGCGGCGAA AATACAACCG CCCAGAACTT TGCCACTCAC TCGGACGACA
  901  TGATAAGCAA AGGACCGTAC GGGGGGGGCA TGACTACCAC CAAATTCACT
  951  CTGAGAATAC TGTACGACGA GTTTACCAGG TTTATGAACT TTTGGACTGT
 1001  CAGTAACGAA GACCTAGACC TGTGTAGATA CGTGGGCTGC AAACTAATAT
 1051  TTTTTAAACA CCCCACGGTG GACTTTATAG TACAGATAAA CACTCAGCCT
 1101  CCTTTCTTAG ACACGCACCT CACCGCGGCC AGCATACACC CGGGCATCAT
 1151  GATGCTCAGC AAGAGACACA TACTAATACC CTCTCTAAAG ACCCGGCCCA
 1201  GCAGAAAACA CAGGGTGGTC GTCAGGGTGG GCGCCCCAAG ACTTTTTCAG
 1251  GACAAGTGGT ACCCCCAGTC AGACCTGTGT GACACAGTTC TGCTTTCCAT
 1301  ATTTGCAACC GCCTGCGACT TGCAATATCC GTTCGGCTCA CCACTAACTG
 1351  ACAACCCTTG CGTCAACTTC CAGATCCTGG GGCCCCAGTA CAAAAAACAC
 1401  CTTAGTATTA GCTCCACTAT GGATCAAACT AACGAAAACC ATTATAAAGA
 1451  AAACTTATTT AACAAAACTG AACTATACAA CACCTTTCAA ACCATAGCTC
 1501  AGCTTAAAGA GACAGGACAC ATTTCAGGCA TTAGTCCTAC TTGGAATGAA
 1551  GTCCAGAATT CAACAACACT TACTAAAGGA GGTGACAATG CCACTCAGAG
 1601  TAGAGACACT TGGTATAAAG GAAATACATA CAACGAGAAG ATATGCGAGT
```

FIG. 12A Cont'

```
1651  TAGCACAAAT AACCAGAAAC AGATTTAAAA ATGCAACCAA AGGAGCACTA
1701  CCAAACTACC CCACAATAAT GTCCACAGAC CTATATGAAT ACCACTCAGG
1751  CATACACTCC AGCATATATC TATCAGCTGG CAGGAGCTAC TTTGAAACCA
1801  CCGGGGCCTA CTCTGACATT ATATACAACC CTTTCACAGA CAAAGGCACA
1851  GGCAACATAA TCTGGATAGA CTACCTCACA AAAGAAGACA CCATTTTTGT
1901  GAAAAACAAA AGCAAATGCG AGATAATGGA CATGCCCCTG TGGGCGGCCT
1951  GCACAGGATA CACAGAGTTT TGTGCAAAGT ATACAGGCGA CTCTGCCATT
2001  ATCTACAATG CAAGAATACT CATAAGATGC CCATACACTG AGCCCATGTT
2051  AATAGACCAC TCAGACCCAA ACAAAAGCTT CGTTCCCTAC TCATTTAACT
2101  TTGGCAACGG AAAGATGCCC GGAGGCAGCT CCAACGTGCC CATAAGAATG
2151  AGAGCCAAGT GGTACGTGAA CATATTCCAC CAAAAGAAG TATTAGAGAG
2201  CATAGTACAG TCCGGACCGT TTGGGTACAA GGGCGACATA AGATCAGCTG
2251  TACTAGCCAT GAAATACAGA TTTCACTGGA AGTGGGCGG AAACCCTATA
2301  TCCAAACAGG TCGTCAGGAA TCCCTGCTCC AACTCCAGCT CCTCCGCGGC
2351  CCATAGAGGA CCTCGCAGCG TACAAGCGGT TGACCCGAAA TACAATACCC
2401  CAGAGGTCAC GTGGCACTCG TGGGACATTA GACGAGGACT CTTTGGCAAA
2451  GCAGGTATTA AAAGAATGCA ACAGGAATCA GATGCTCTTT ACATTCCTCC
2501  AGGACCAATC AAGAGACCTC GCAGGGACAC CAACGCCCAA GACCCAGAAG
2551  AGCAAAACGA AAGCTCAGGT TTCAGAGTCC AGCAGCGACT CCCGTGGGTC
2601  CACTCCAGCC AAGAGACGCA AAGCTCCCAA GAAGAGACGG AGGCGCAGGG
2651  GTCGGTACAA GACCAACTAC TCCTCCAGCT CCGAGAGCAG CGAGTTCTCC
2701  GACTCCAGCT CCAGCAACTC GCAACCCAAG TCCTCAAAGT CCAAGCAGGG
2751  CACAGCCTAC ACCCCCTATT ATCTTCCCAA GCATAAACAA AGCCTTTATG
2801  TTTGAGCCCC AGGGTCCTAA ACCCATACAG GGGTACAACG ACTGGCTAGA
2851  AGAGTACACT GCTTGCAAAT TCTGGGACAG ACCCCCCAGA AAGCTACACA
2901  CAGACATACC CTTCTACCCC TGGGCACCAA AACCCCAACA GCAAGTCAGG
2951  GTGTCCTTTA AACTCAACTT TCAATAAAAA TTCTAGGCCG TGGGAGTTTC
3001  ACTTGTCGGT GTCTGCTTCT TAAGGTCGCC AAGCACTCCG AGCGCCAGCG
3051  AGGAGTGCGA CCCCCCCTCC GGTAGCAACG CCTTCGGAGC CGCGCGCTAC
3101  GCCTTCGGCT GCGCGCGGCA CCTCAGACCC CCCCTCCACC CGAAACGCTT
3151  GCGCGTTTCG GACCTTCGGC GTCGGGGGGG TCGGGAGCTT TATTAAACAG
3201  ACTCCGAGTT GCCATTGGAC ACTGGAGCTG TGAATCAGTA ACGAAAGTGA
3251  GTGGGGCCAG ACTTCGCCAT AGGGCCTTTA TCTTCTCGCC ATTGGATAGT
3301  GTCCGGGGTC GCCGTAGGCT TCGGCCTCGT TTTTAGGCCT TCCGGACTAC
3351  AAAAATGGCG GTTTTAGTGA CGTCACGGCC GCCATTTTAA GTAAGGCGGA
3401  AGCAGCTCCA CTTTCTCACA AAATGGCGGC GGAGCACTTC CGGCTTGCCC
3451  AAAATGGCGG GCAAGCTCTT CCGGGTAAAG GGTCAGCAGC TACGTCACAA
3501  GTCACCTGAC TGGGGAGGGG TCACAACCCG GAAGCCCTCC TCAGTCACGT
3551  GGCTGTTCAC GTGGTTGCTA CGTCATCGGC GCCATCTTGT GTCGCAAAAT
```

FIG. 12A Cont'

```
3601  GGCGGACAAC TTCCGCTTTT TTAAAAAAAG GCGCGAAAAA ACGGCGGCGG
3651  CGGCGCGCGC GCTGTGCGCG CGCGCCGGGG GGGCGCCAGC GCCCCCCCCC
3701  CCGCGCATGC GCGGGTCCCC CCCCCCGCGG GGGGCTCCGC CCCCCGGCCC
3751  CCCCCCCG
```

FIG. 12B

```
zpr9.6
zpr9.B1.6.seq (subviral molecule, tth25)
 293TT+9(tth25smfr3)PCR
Tr11.8 C/6
In pCR2.1,ONEShot Topo10F' zpr9.B1.6.seq   Length: 621
        1  CCGCAGCGAG AACGCCACGG AGGGAGATCC TCGCGTCCCG AGGGCGGGTG
       51  CCGGAGGTGA GTTTACACAC CGCAGTCAAG GGGCAATTCG GGCTCGGGAC
      101  TGGCCGGGCC CCGGGCAAGG CTCTTAAAAA ATGCGTTTTC GCAGGGTTGC
      151  CCAGAAAAGG AAAGTGCTTT TGCAAACTGT GCCAGCTGCA AAGAAGGCTA
      201  GGCGGCTTCT AGGTATGTGG CAGCCCCCCA CGCACAATGT CCCGGGCATC
      251  GAGAGAAACT GGTACGAGAG CTGTTTTAGA TCCCACGCTG CTGTTTGTGG
      301  CTGTGGCGAT TTTGTTGGCC ATCTTAATCA TCTGGCAACT ACTCTGGGTC
      351  GTCCTCCGCG TCCTGGGCCC CAGGCGGAC  CCCGCACGCC GCAAATAAGA
      401  AACCTGCCAG CGCTCCCGGC GCCCAGGGC  GAGCCCGGTG ACAGAGCGCC
      451  ATGGCATGGG GCTTCTGGGG CCGACGCCGC CGGTGGAGAC GATGGAGAGC
      501  GCGGCGCAGA CGGTGGAGAC CCCGCAGGCC AACCAGAGTC TACGTCGTGC
      551  ACTTCCTGGG CATGGTCTAC ATCATAATAT AAGAACGTGC ACTTCCGAAT
      601  GGCTGAGTTT TCCACGCCCG T
```

FIG. 13A ttrh215
rheu.cd.215.seq
Genomiphi tth4-primer
ann.78°+ additional taq polymerase(progr.tth4*78)
vector:TA-cloning pcr2.1 invitrogen rheu.cd.215rp.seq   Length: 3758

```
   1 AAAGTACGTC ACTAACCACG TGACTCCCAC AGGCCAACCA CAGTCTACGT
  51 CGTGCATTTC CTGGGCATGG TCTACATCAT AATATAAGAA GGCGCACTTC
 101 CGAATGGCTG AGTTTTCCAC GCCCGTCCGC AGCGAGAACG CCACGGAGGG
 151 AGATCCTCGC GTCCCGAGGG CGGGTGCCGG AGGTGAGTTT ACACACCGCA
 201 GTCAAGGGGC AATTCGGGCT CGGGACTGGC CGGGCCCTGG GCAAGGCTCT
 251 TAAAAAATGC GCTTTCGCAG GGTTGCGGAG AAAAGGAAAG TGCTTCTGCA
 301 AACTCTGCGA GCTGCAAAGC AGGCTAGGCG GCTTCTAGGT ATGTGGCAGC
 351 CCCCCGCGCA CAATGTCCCC GGCATCGAGA GAAACTGGTA CGAGAGCTGC
 401 TTCAGGTCTC ACGCTGCTGT TTGTGGCTGT GGCGACTTTG TTGGCCATAT
 451 TAATCATTTG GCAACTACTC TGGGTCGTCC TCCGCGTCCT GGGCCCCCAG
 501 GCGGACCCCG CACGCCGCAA ATAAGAAACC TGCCAGCGCT CCCGGCGCCC
 551 CAGGGCGAGC CCGGTGACAG AGCGCCATGG CGTGGGGTTT CTGGGGCCGA
 601 CGCCGCCGGT GGAGACGGTG GAGAGCGCGG CGCAGACGGT GGAGACCCCG
 651 GAGACGTAGG AGACGACGCC CTGCTCGCCG CTTTCGAGCT CGTCGAAGAG
 701 TAAGGAGACG CGGGGGGAGG TGGCGCAGAC GCTACAGAAA ATGGCGACGG
 751 GGCAGACGCA GACGGACTCA CAGAAAAAAG ATAATTATAA AACAGTGGCA
 801 ACCAAACTTT ATTAGACGCT GCTACATAAT AGGATGCCTA CCTCTCGTTT
 851 TCTGTGGCGA AAATACAACC GCCCAGAACT ATGCCACTCA CTCAGACGAT
 901 ATGATAAGCA AAGGACCGTA CGGGGGGGGC ATGACTACCA CGAAATTCAC
 951 TCTGAGAATA CTGTACGACG AGTTTACCAG GTTTATGAAC TTTTGGACTG
1001 TCAGTAACGA AGACCTAGAC CTGTGTAGAT ACGTGGGCTG CAAACTGATA
1051 TTTTTTAAAC ACCCCACGGT GGACTTTATG GTACAGATAA ACACTCAGCC
1101 TCCTTTCTTA GACACAAGCC TCACCGCGGC CAGCATACAC CCGGGCATCA
1151 TGATGCTCAG CAAGAGACGC ATATTAATAC CCTCTCTAAA GACCCGGCCG
1201 AGCAGAAAAC ACAGGGTGGT CGTCAGGGTG GGCGCCCCAA GACTTTTTCA
1251 GGACAAGTGG TACCCCCAGT CAGACCTATG TGACACAGTT CTGCTTTCCA
1301 TATTTGCAAC CGCCCGCGAC TTGCAATATC CGTTCGGCTC ACCACTAACT
1351 GACAACCCTT GCGTCAACTT CCAGATCCTG GGGCCCCAGT ACAAAAAACA
1401 CCTTAGTATT AGCTCCACTA TGGATGATAC TAACAAACAG CACTATAACA
1451 GCAACTTATT TAATAAAACT GCACTATACA ACACCTTTCA AACCATAGCC
```

FIG. 13A Cont'

```
1501  CGGCTTAAAG AGACAGGACA AACTGCAAAC ATTAGTCCAA GTTGGAGTGA
1551  AGTACAAAAC ACAAAACTAC TAGATCACAC AGGTGCTAAT GCAACTGCCA
1601  GCAGAGACAC TTGGTACAAG GGAAACACAT ACAATGACTA CATACAACAG
1651  TTAGCAGAGA AAACAAGAGA AAGGTTTAAA AAAGCAACAA TGTCAGCACT
1701  ACCAAACTAC CCCACAATAA TGTCCACAGA CTTATACGAA TACCACTCAG
1751  GCATATACTC CAGCATATTT CTATCAGCTG GCAGGAGCTA CTTTGAAACC
1801  ACTGGGGCCT ACTCTGACAT TATATACAAC CCTTTGACAG ACAAAGGCAC
1851  AGGCAACATA ATCTGGATAG ACTACCTTAC AAAAGACGAC ACAATCTTTG
1901  TAAAAAACAA AAGCAAATGT GAGATAATGG ACATGCCCCT GTGGGCGGCC
1951  GGCACAGGAT ACACAGAGTT TTGTGCAAAG TACACAGGAG ACTCTGCCAT
2001  TATTTACAAT GCCAGAATAC TCATAAGATG CCCATACACT GAACCCATGC
2051  TAATAGACCA CTCAGACCCA AACAAAGGCT TTGTACCGTA CTCATTTAAC
2101  TTTGGCAACG GAAAGATGCC GGGAGGCAGC TCCAACGTGC CCATAAGAAT
2151  GAGAGCCAAG TGGTACGTAA ACATATTCCA CCAAAAAGAA GTATTGGAGA
2201  GCATAGTACA GTCCGGACCG TTCGGGTACA GGGCGACAT AAAATCAGCT
2251  GTACTGTCCA TGAAATACAG ATTTCACTGG AAATGGGCG GAAACCCTAT
2301  ATCCAAACAG GTCGTCAGGA ATCCCTGCTC CAACTCCAGC ACCTCCGCGG
2351  CCCATAGAGG ACCTCGCAGC GTACAAGCGG TTGACCCGAA ATACAATACC
2401  CCAGAAGTCA CTTGGCACTC GTGGGACATC AGACGAGGAC TCTTTGGCAA
2451  AGCAGGTATT AAAAGAATGC AACAAGAATC AGATGCTCTT TACGTTCCTG
2501  CAGGACCACT CAAGAGGCCT CGCAGAGACA CCAACGCCCA AGACCCGGAA
2551  AAGCAAAACG AAAGCTCACG TTTCGGAGTC CAGCAGCGAC TCCCGTGGGT
2601  CCACTCCAGC CAAGAGACGC AAAGCTCCGA AGAAGAGACG CAGGCGCAGG
2651  GGTCGGTACA AGACCAACTA CTCCTCCAGC TCCGAGAGCA GCGAGTACTC
2701  CGACTCCAGC TCCAACAACT CGCACCCCAA GTCCTCAAAG TTCAAGCAGG
2751  ACACAGCCTA CACCCCTAT TATCCTCCCA AGCATAAACA AAGCCTATAT
2801  GTTTGAACCC CAGGGTCCTA AACCCATACA GGGGTACAAC GATTGGCTAG
2851  AGGAGTACAC TAGTTGCAAG TTCCGGGACA GACCCCCGAG AATGCTACAC
2901  ACAGACTTAC CCTTTTACCC CTGGGCACCA AAACCCCAAG ACCAAGTCAG
2951  GGTAACCTTT AAACTCAACT TTCAATAAAA ATTCTAGGCC GTGGGACTTT
3001  CACTTGTCGG TGTCTGCTTC TTAAGGTCGC CAAGCACTCC GAGCGTCAGC
3051  GAGGAGTGCG ACCCCCCCCC TCGGTAGCAA CGCCTTCGGA GCCGCGCGCT
3101  ACGCCTTCGG CTGCGCGCGG CACCTCAGAC CCCCCCTCCA CCCGAAACGC
3151  TTGCGCGTTT CGGACCTTCG GCGTCGGGGG GGTCGGGAGC TTTATTAAAC
3201  AGACTCCGAG TTGCCATTGG ACACTGGAGC TGTGAATCAG TAACGAAAGT
3251  GAGTGGGCC AGACTTCGCC ATAGGGCCTT TATCTTCTCG CCATTGGATA
3301  GTGTCCGGGG TTGCCGTAGG CTTCGGCCTC GTTTTAGGC CTTCCGGACT
3351  ACAAAAATGG CGGATTTTGT GACGTCACGG CCGCCATTTT AAGTAAGGCG
3401  GAAGCAGCTC CACCCTCTCA CATAATGGCG GCGGAGCACT CCCGGCTTGC
```

FIG. 13A Cont'

```
3451 CCAAAATGGC GGGCAAGCTC TTCCGGGTCA AAGGTTGGCA GCTACGTCAC
3501 AAGTCACCTG ACTGGGGAGG AGTTACATCC CGGAAGTTCT CCTCGGTCAC
3551 GTGACTGTAC ACGTGACTGC TACGTCATTG ACGCCATCTT GTGTCACAAA
3601 ATGGCGGTGC ACTTCCGCTT TTTTGAAAAA AGGCGCGAAA AAACGGCGGC
3651 GGCGGCGCGC GCGCTGCGCG CGCGCGCCGG GGGGCGCCA GCGCCCCCCC
3701 CCCCGCGCAT GCACGGGTCC CCCCCCCCAC GGGGGGCTCC GCCCCCCGGC
3751 CCCCCCCC
```

FIG. 13B zpr12.24
zpr12.24.seq (subviral molecule, ttrh215)
Length: 642

```
  1 CAGCGAGAAC GCCACGGAGG GAGATCCTCG CGTCCCGAGG GCGGGTGCCG
 51 GAGGTGAGTT TACACACCGC AGTCAAGGGG CAATTCGGGC TCGGGACTGG
101 CCGGGCCCCG GGCAAGGCTC TTAAAAAATG CGCTTTCGCA GGGTTGCTGA
151 GAAAAGGAAA GTGCTTCTGC AAACTGTGCG AGCTACACAG AAGACTAGGC
201 GGCTTCTAAG CCGCCCACAG GGGCATGTCT ACATGCTTCC GCAGCGAGAA
251 CGCCACGGAG GGAGATCCTC GCGTCCCGAG GGCGGGTGCC GGAGGTGAGT
301 TTACACACCG CAGTCAAAGG GCAATTCGGG CTCGGGACTG GCCGGGCCCC
351 GGGCAAGGCT CTTAAAAAAT GCGCTTTCGC GGGGTTGCTG AGAAAAGGAA
401 AGTGCTTCTG CAAACTGTGC GAGCTACACA GAAGACTAGG CGGCTTCTAG
451 GTATGTGGCA GCCCCCCGTG CACAATGTCC CCGGCATCTT ATTAGTACTC
501 TGGCGTTGTA GATAATGGCA GAGTCTCCAG TGTACTTTGC ACAGAACTCT
551 GTGTATCCTG TGCAGGCCGC CCACAGGGGC ATGTCTACAT CATAATATAA
601 TAAGGCGCAC TTCCGAATGG CTGAGTTTTC CACGCCCGTC CG
```

FIG. 14A

*Open reading frames of 71 nt (HCR):*

```
zyb2.1.pep    RVPKVSLHTA VKGQFGLGTG RAM
zyb9.1.pep    RVPKVSLHTA VKGQFGLGTG RAM
zkb69.1.pep   RVPEVSLHTA VKGQFGLGTG RAM zyb2.3.pep    GAEGEFTHRS QGAIRARDWP GHG
zyb9.3.pep    GAEGEFTHRS QGAIRARDWP GYG
zkb5.3.pep    GAVGEFTHRS QGAIRARDWP GYG
zkb69.3.pep   GAGGEFTHRS QGAIRARDWP GYG
```

FIG. 14B

```
zyb2.1.pep
nucleotide 1-71
Length: 23aa

RVPKVSLHTA VKGQFGLGTG RAM

BlastP2 of: zyb2.1.pep
compared to database: uniprot
>>>sptrembl:Q9WSW0_9VIRU  Q9wsw0  SubName: Full=ORF2; Flags: Fragm...    49    1e-04
>>>sptrembl:Q9WB09_9VIRU  Q9wb09  SubName: Full=ORF2; Flags: Fragm...    48    4e-04
>>>sptrembl:Q9WSW2_9VIRU  Q9wsw2  SubName: Full=ORF2; Flags: Fragm...    48    4e-04
>>>sptrembl:Q9WSX0_9VIRU  Q9wsx0  SubName: Full=ORF2; Flags: Fragm...    47    4e-04
>>>sptrembl:Q9WB10_9VIRU  Q9wb10  SubName: Full=ORF2; Flags: Fragm...    47    5e-04
>>>sptrembl:Q9WAZ2_9VIRU  Q9waz2  SubName: Full=ORF2; Flags: Fragm...    47    5e-04
>>>sptrembl:O70807_9VIRU  O70807  SubName: Full=Putative uncharact...   47    6e-04
>>>sptrembl:Q9WAY4_9VIRU  Q9way4  SubName: Full=ORF2; Flags: Fragm...    47    7e-04
>>>sptrembl:Q9WB02_9VIRU  Q9wb02  SubName: Full=ORF2; Flags: Fragm...    47    8e-04
>>>sptrembl:Q9WSW4_9VIRU  Q9wsw4  SubName: Full=ORF2; Flags: Fragm...    46    0.001
>>>sptrembl:Q9WB12_9VIRU  Q9wb12  SubName: Full=ORF2; Flags: Fragm...    46    0.001
>>>sptrembl:Q9WSW6_9VIRU  Q9wsw6  SubName: Full=ORF2; Flags: Fragm...    45    0.002
>>>sptrembl:B3FWR6_9VIRU  B3fwr6  SubName: Full=ORF2; Flags: Fragm...    36    0.94

>>>>sptrembl:Q9WSW0_9VIRU  Q9wsw0  SubName: Full=ORF2; Flags:
         Fragment;. 2/2010
         Length = 204
 Score = 49.3 bits (116),  Expect = 1e-04,   Method: Compositional matrix adjust.
 Identities = 23/23 (100%), Positives = 23/23 (100%)
Query: 1   RVPKVSLHTAVKGQFGLGTGRAM 23
           RVPKVSLHTAVKGQFGLGTGRAM
Sbjct: 27  RVPKVSLHTAVKGQFGLGTGRAM 49

>>>>sptrembl:Q9WB09_9VIRU  Q9wb09  SubName: Full=ORF2; Flags:
         Fragment;. 2/2010
         Length = 138
 Score = 47.8 bits (112),  Expect = 4e-04,   Method: Compositional matrix adjust.
 Identities = 22/23 (95%), Positives = 22/23 (95%)
Query: 1   RVPKVSLHTAVKGQFGLGTGRAM 23
           RVPKVSLHT VKGQFGLGTGRAM
Sbjct: 14  RVPKVSLHTEVKGQFGLGTGRAM 36

ID   Q9WSW0_9VIRU              Unreviewed;       204 AA.
```

```
AC   Q9WSW0;
DT   01-NOV-1999, integrated into UniProtKB/TrEMBL.
DT   01-NOV-1999, sequence version 1.
DT   09-FEB-2010, entry version 23.
DE   SubName: Full=ORF2;
DE   Flags: Fragment;
OS   Torque teno virus.
OC   Viruses; ssDNA viruses; Anelloviridae; unclassified Anelloviridae.
OX   NCBI_TaxID=68887;
RN   [1]
RP   NUCLEOTIDE SEQUENCE.
RC   STRAIN=KC205/1-12G; TISSUE=Serum;
RX   MEDLINE=99335592; PubMed=10405352; DOI=10.1006/viro.1999.9797;
RA   Hijikata M., Takahashi K., Mishiro S.;
RT   "Complete circular DNA genome of a TT virus variant (isolate name
RT   SANBAN) and 44 partial ORF2 sequences implicating a great degree of
RT   diversity beyond genotypes.";
RL   Virology 260:17-22(1999).
CC   -----------------------------------------------------------------------
CC   Copyrighted by the UniProt Consortium, see http://www.uniprot.org/terms
CC   Distributed under the Creative Commons Attribution-NoDerivs License
CC   -----------------------------------------------------------------------
DR   EMBL; AB024383; BAA77450.2; -; Genomic_DNA.
DR   InterPro; IPR004118; Gyrovir_VP2/TT_ORF2.
DR   Pfam; PF02957; TT_ORF2; 1.
PE   4: Predicted;
FT   NON_TER      1      1
SQ   SEQUENCE   204 AA;  21953 MW;  6352C96D2AC0DF21 CRC64;
     CTSEWLSFPR PSAAAXPRRV IPASRWRVPK VSLHTAVKGQ FGLGTGRAMG KALKVFILKM
     HFSRISRSKR KVLLPALPAP PPPRQLLMWQ PPIQNGTQLD RHWFESVWRS HAAYCGCGDC
     VGHLQHLAAN LGRPPHPQPP REQHPPQIRG LPALPAPPSN RNSWPGTGGD AAGEQAGGSR
     GAGDGGDGEL ADDDLXDAAA LVEE ID   Q9WB09_9VIRU            Unreviewed;       138 AA.
AC   Q9WB09;
DT   01-NOV-1999, integrated into UniProtKB/TrEMBL.
DT   01-NOV-1999, sequence version 1.
DT   09-FEB-2010, entry version 22.
DE   SubName: Full=ORF2;
DE   Flags: Fragment;
OS   Torque teno virus.
OC   Viruses; ssDNA viruses; Anelloviridae; unclassified Anelloviridae.
OX   NCBI_TaxID=68887;
RN   [1]
RP   NUCLEOTIDE SEQUENCE.
RC   TISSUE=Serum;
RX   MEDLINE=99335592; PubMed=10405352; DOI=10.1006/viro.1999.9797;
RA   Hijikata M., Takahashi K., Mishiro S.;
RT   "Complete circular DNA genome of a TT virus variant (isolate name
RT   SANBAN) and 44 partial ORF2 sequences implicating a great degree of
RT   diversity beyond genotypes.";
RL   Virology 260:17-22(1999).
CC   -----------------------------------------------------------------------
CC   Copyrighted by the UniProt Consortium, see http://www.uniprot.org/terms
CC   Distributed under the Creative Commons Attribution-NoDerivs License
CC   -----------------------------------------------------------------------
DR   EMBL; AB024376; BAA77443.1; -; Genomic_DNA.
DR   InterPro; IPR004118; Gyrovir_VP2/TT_ORF2.
DR   Pfam; PF02957; TT_ORF2; 1.
PE   4: Predicted;
FT   NON_TER      1      1
FT   NON_TER    138    138
SQ   SEQUENCE   138 AA;  15494 MW;  2DF27B3A4F0CA641 CRC64;
```

FIG. 14B Cont'

FIG. 14B Cont'

AVKPRREISA SRGRVPKVSL HTEVKGQFGL GTGRAMGKAL KKSMFIGRHY RKKRALSLCA
VRTTKKACKL LIVMWTPPRN DQQYLNWQWY SSVLSSHAAM CGCPDAIAHL SHLAFVFRAP
QNPPPPGPQR NLPLRRLP

FIG. 14C zyb2.3.pep
nucleotide 3-71
Length: 23aa

GAEGEFTHRS QGAIRARDWP GHG

```
BlastP2 of: zyb2.3.pep   from: 1 to: 23
compared to database: uniprot    ..
>>>sptrembl:Q98Y39_9VIRU  Q98y39 SubName: Full=ORF2;. 2/2010           50    7e-05
>>>sptrembl:Q9WAY7_9VIRU  Q9way7 SubName: Full=ORF2; Flags: Fragm...   50    7e-05
>>>sptrembl:Q786D4_9VIRU  Q786d4 SubName: Full=ORF2;. 2/2010           50    9e-05
>>>sptrembl:O70738_9VIRU  O70738 SubName: Full=ORF2, ORF1 genes;....   50    9e-05
>>>sptrembl:Q9JG33_9VIRU  Q9jg33 SubName: Full=Putative uncharact...   50    9e-05
>>>sptrembl:O90363_9VIRU  O90363 SubName: Full=ORF2 protein;. 2/2010   50    9e-05
>>>sptrembl:Q9WFY6_9VIRU  Q9wfy6 SubName: Full=ORF2;. 2/2010           50    1e-04
>>>sptrembl:Q9JGT0_9VIRU  Q9jgt0 SubName: Full=PORF2a;. 12/2009        50    1e-04
>>>sptrembl:Q9YKL2_9VIRU  Q9ykl2 SubName: Full=ORF2 protein;. 2/2010   50    1e-04
>>>sptrembl:Q9JGS7_9VIRU  Q9jgs7 SubName: Full=PORF2a;. 12/2009        49    1e-04
>>>sptrembl:Q9DYC0_9VIRU  Q9dyc0 SubName: Full=Putative uncharact...   49    1e-04
>>>sptrembl:Q9W7S4_9VIRU  Q9w7s4 SubName: Full=Putative uncharact...   49    2e-04
>>>sptrembl:Q77S01_9VIRU  Q77s01 SubName: Full=Putative uncharact...   49    2e-04
>>>sptrembl:Q9JGT3_9VIRU  Q9jgt3 SubName: Full=PORF2a;. 12/2009        46    0.001
>>>sptrembl:Q9JGS4_9VIRU  Q9jgs4 SubName: Full=PORF2a;. 12/2009        46    0.001
>>>sptrembl:Q9YR02_9VIRU  Q9yr02 SubName: Full=Putative uncharact...   45    0.003
>>>sptrembl:B2YFW4_9VIRU  B2yfw4 SubName: Full=ORF2; Flags: Fragm...   34    3.7

>>>>sptrembl:Q98Y39_9VIRU  Q98y39 SubName: Full=ORF2;. 2/2010
         Length = 202
 Score = 50.1 bits (118), Expect = 7e-05,  Method: Compositional matrix adjust.
 Identities = 22/23 (95%), Positives = 23/23 (100%)
Query: 1   GAEGEFTHRSQGAIRARDWPGHG 23
           GAEGEFTHRSQGAIRARDWPG+G
Sbjct: 24  GAEGEFTHRSQGAIRARDWPGYG 46

Q98Y39_9VIRU            Unreviewed;       202 AA.
AC   Q98Y39;
DT   01-JUN-2001, integrated into UniProtKB/TrEMBL.
DT   01-JUN-2001, sequence version 1.
DT   09-FEB-2010, entry version 17.
DE   SubName: Full=ORF2;
OS   Torque teno virus.
OC   Viruses; ssDNA viruses; Anelloviridae; unclassified Anelloviridae.
OX   NCBI_TaxID=68887;
RN   [1]
RP   NUCLEOTIDE SEQUENCE.
RC   STRAIN=TWH;
RA   He H.-T., Luo K.-X., Xiao H., Liu D.-X.;
RT   "Complete circular genome of TT virus isolated from feces of a
RT   hepatitis patient.";
RL   Submitted (FEB-2001) to the EMBL/GenBank/DDBJ databases.
CC   -----------------------------------------------------------------------
CC   Copyrighted by the UniProt Consortium, see http://www.uniprot.org/terms
CC   Distributed under the Creative Commons Attribution-NoDerivs License
CC   -----------------------------------------------------------------------
DR   EMBL; AF351132; AAK29446.1; -; Genomic_DNA.
DR   InterPro; IPR004118; Gyrovir_VP2/TT_ORF2.
DR   InterPro; IPR013267; TTV_ORF2a.
```

FIG. 14C Cont'

```
DR   Pfam; PF02957; TT_ORF2; 1.
DR   Pfam; PF08197; TT_ORF2a; 1.
PE   4: Predicted;
SQ   SEQUENCE   202 AA;  21437 MW;  105B9ED104956EDE CRC64;
     MAEFSTPVRS GEATEGDHRV PRAGAEGEFT HRSQGAIRAR DWPGYGQGSE KSMFIGRHYR
     KKRALSLCAV RTTKKACKLL IVMWTPFRND QQYLNWQWYS SVLSSHASMC GCPDAVAHLI
     NLASVLRAPQ NPPPPGPQRN LFLRRLPALP AAPEAPGDRA PWPMAGGAEG ENGGAGGDAD
     HGGAAGGPED ANLLDAVAAA ET
//
```

FIG. 14D

```
zyb9.1.pep
nucleotide 1-71
Length: 23aa

RVPKVSLHTA VKGQFGLGTG RAM

BlastP2 of: zyb9.1.pep   from: 1 to: 23
compared to database: uniprot    ..
>>>sptrembl:Q9WSW0_9VIRU  Q9wsw0 SubName: Full=ORF2; Flags: Fragm...    49    1e-04
>>>sptrembl:Q9WB09_9VIRU  Q9wb09 SubName: Full=ORF2; Flags: Fragm...    48    4e-04
>>>sptrembl:Q9WSW2_9VIRU  Q9wsw2 SubName: Full=ORF2; Flags: Fragm...    48    4e-04
>>>sptrembl:Q9WSX0_9VIRU  Q9wsx0 SubName: Full=ORF2; Flags: Fragm...    47    4e-04
>>>sptrembl:Q9WB10_9VIRU  Q9wb10 SubName: Full=ORF2; Flags: Fragm...    47    5e-04
>>>sptrembl:Q9WAZ2_9VIRU  Q9waz2 SubName: Full=ORF2; Flags: Fragm...    47    5e-04
>>>sptrembl:O70807_9VIRU  O70807 SubName: Full=Putative uncharact...    47    6e-04
>>>sptrembl:Q9WAY4_9VIRU  Q9way4 SubName: Full=ORF2; Flags: Fragm...    47    7e-04
>>>sptrembl:Q9WB02_9VIRU  Q9wb02 SubName: Full=ORF2; Flags: Fragm...    47    8e-04
>>>sptrembl:Q9WSW4_9VIRU  Q9wsw4 SubName: Full=ORF2; Flags: Fragm...    46    0.001
>>>sptrembl:Q9WB12_9VIRU  Q9wb12 SubName: Full=ORF2; Flags: Fragm...    46    0.001
>>>sptrembl:Q9WSW6_9VIRU  Q9wsw6 SubName: Full=ORF2; Flags: Fragm...    45    0.002
>>>sptrembl:B3FWR6_9VIRU  B3fwr6 SubName: Full=ORF2; Flags: Fragm...    36    0.94

>>>>sptrembl:Q9WSW0_9VIRU  Q9wsw0 SubName: Full=ORF2; Flags:
         Fragment;. 2/2010
         Length = 204
 Score =  49.3 bits (116), Expect = 1e-04,   Method: Compositional matrix adjust.
 Identities = 23/23 (100%), Positives = 23/23 (100%)
Query: 1   RVPKVSLHTAVKGQFGLGTGRAM 23
           RVPKVSLHTAVKGQFGLGTGRAM
Sbjct: 27  RVPKVSLHTAVKGQFGLGTGRAM 49

>>>>sptrembl:Q9WB09_9VIRU  Q9wb09 SubName: Full=ORF2; Flags:
         Fragment;. 2/2010
         Length = 138
 Score =  47.8 bits (112), Expect = 4e-04,   Method: Compositional matrix adjust.
 Identities = 22/23 (95%), Positives = 22/23 (95%)
Query: 1   RVPKVSLHTAVKGQFGLGTGRAM 23
           RVPKVSLHT VKGQFGLGTGRAM
Sbjct: 14  RVPKVSLHTEVKGQFGLGTGRAM 36

Q9WSW0_9VIRU            Unreviewed;      204 AA.
AC   Q9WSW0;
DT   01-NOV-1999, integrated into UniProtKB/TrEMBL.
DT   01-NOV-1999, sequence version 1.
DT   09-FEB-2010, entry version 23.
DE   SubName: Full=ORF2;
DE   Flags: Fragment;
```

```
OS   Torque teno virus.
OC   Viruses; ssDNA viruses; Anelloviridae; unclassified Anelloviridae.
OX   NCBI_TaxID=68887;
RN   [1]
RP   NUCLEOTIDE SEQUENCE.
RC   STRAIN=KC205/1-12G; TISSUE=Serum;
RX   MEDLINE=99335592; PubMed=10405352; DOI=10.1006/viro.1999.9797;
RA   Hijikata M., Takahashi K., Mishiro S.;
RT   "Complete circular DNA genome of a TT virus variant (isolate name
RT   SANBAN) and 44 partial ORF2 sequences implicating a great degree of
RT   diversity beyond genotypes.";
RL   Virology 260:17-22(1999).
CC   -----------------------------------------------------------------------
CC   Copyrighted by the UniProt Consortium, see http://www.uniprot.org/terms
CC   Distributed under the Creative Commons Attribution-NoDerivs License
CC   -----------------------------------------------------------------------
DR   EMBL; AB024383; BAA77450.2; -; Genomic_DNA.
DR   InterPro; IPR004118; Gyrovir_VP2/TT_ORF2.
DR   Pfam; PF02957; TT_ORF2; 1.
PE   4: Predicted;
FT   NON_TER       1       1
SQ   SEQUENCE   204 AA;  21953 MW;  6352C96D2AC0DF21 CRC64;
     CTSEWLSFPR PSAAAXPRRV IPASRWRVPK VSLHTAVKGQ FGLGTGRAMG KALKVFILKM
     HFSRISRSKR KVLLPALPAP PPPRQLLMWQ PPIQNGTQLD RHWFESVWRS HAAYCGCGDC
     VGHLQHLAAN LGRPPHPQPP REQHPPQIRG LPALPAPPSN RNSWPGTGGD AAGEQAGGSR
     GAGDGGDGEL ADDDLXDAAA LVEE Q9WB09_9VIRU             Unreviewed;       138 AA.
AC   Q9WB09;
DT   01-NOV-1999, integrated into UniProtKB/TrEMBL.
DT   01-NOV-1999, sequence version 1.
DT   09-FEB-2010, entry version 22.
DE   SubName: Full=ORF2;
DE   Flags: Fragment;
OS   Torque teno virus.
OC   Viruses; ssDNA viruses; Anelloviridae; unclassified Anelloviridae.
OX   NCBI_TaxID=68887;
RN   [1]
RP   NUCLEOTIDE SEQUENCE.
RC   TISSUE=Serum;
RX   MEDLINE=99335592; PubMed=10405352; DOI=10.1006/viro.1999.9797;
RA   Hijikata M., Takahashi K., Mishiro S.;
RT   "Complete circular DNA genome of a TT virus variant (isolate name
RT   SANBAN) and 44 partial ORF2 sequences implicating a great degree of
RT   diversity beyond genotypes.";
RL   Virology 260:17-22(1999).
CC   -----------------------------------------------------------------------
CC   Copyrighted by the UniProt Consortium, see http://www.uniprot.org/terms
CC   Distributed under the Creative Commons Attribution-NoDerivs License
CC   -----------------------------------------------------------------------
DR   EMBL; AB024376; BAA77443.1; -; Genomic_DNA.
DR   InterPro; IPR004118; Gyrovir_VP2/TT_ORF2.
DR   Pfam; PF02957; TT_ORF2; 1.
PE   4: Predicted;
FT   NON_TER       1       1
FT   NON_TER     138     138
SQ   SEQUENCE   138 AA;  15494 MW;  2DF27B3A4F0CA641 CRC64;
     AVKPRREISA SRGRVPKVSL HTEVKGQFGL GTGRAMGKAL KKSMFIGRHY RKKRALSLCA
     VRTTKKACKL LIVMWTPPRN DQQYLNWQWY SSVLSSHAAM CGCPDAIAHL SHLAFVFRAP
     QNPPPPGPQR NLPLRRLP
```

FIG. 14D Cont'

FIG. 14E zyb9.3.pep
nucleotide 3-71
Length: 23aa

GAEGEFTHRS QGAIRARDWP GYG

```
BlastP2 of: zyb9.3.pep   from: 1 to: 23
compared to database: uniprot       ..
>>>sptrembl:Q9WAY7_9VIRU  Q9way7 SubName: Full=ORF2; Flags: Fragm...    52   2e-05
>>>sptrembl:Q98Y39_9VIRU  Q98y39 SubName: Full=ORF2;. 2/2010            52   2e-05
>>>sptrembl:Q9WFY6_9VIRU  Q9wfy6 SubName: Full=ORF2;. 2/2010            52   3e-05
>>>sptrembl:Q9JGT0_9VIRU  Q9jgt0 SubName: Full=PORF2a;. 12/2009         52   3e-05
>>>sptrembl:Q786D4_9VIRU  Q786d4 SubName: Full=ORF2;. 2/2010            52   3e-05
>>>sptrembl:O70738_9VIRU  O70738 SubName: Full=ORF2, ORF1 genes;....    52   3e-05
>>>sptrembl:Q9JG33_9VIRU  Q9jg33 SubName: Full=Putative uncharact...    52   3e-05
>>>sptrembl:O90363_9VIRU  O90363 SubName: Full=ORF2 protein;. 2/2010    52   3e-05
>>>sptrembl:Q9YKL2_9VIRU  Q9ykl2 SubName: Full=ORF2 protein;. 2/2010    51   3e-05
>>>sptrembl:Q9JGS7_9VIRU  Q9jgs7 SubName: Full=PORF2a;. 12/2009         51   3e-05
>>>sptrembl:Q9DYC0_9VIRU  Q9dyc0 SubName: Full=Putative uncharact...    51   4e-05
>>>sptrembl:Q9W7S4_9VIRU  Q9w7s4 SubName: Full=Putative uncharact...    50   5e-05
>>>sptrembl:Q77S01_9VIRU  Q77s01 SubName: Full=Putative uncharact...    50   5e-05
>>>sptrembl:Q9JGS4_9VIRU  Q9jgs4 SubName: Full=PORF2a;. 12/2009         48   3e-04
>>>sptrembl:Q9JGT3_9VIRU  Q9jgt3 SubName: Full=PORF2a;. 12/2009         48   3e-04
>>>sptrembl:Q9YR02_9VIRU  Q9yr02 SubName: Full=Putative uncharact...    47   7e-04
>>>sptrembl:B2YFW4_9VIRU  B2yfw4 SubName: Full=ORF2; Flags: Fragm...    35   3.2

>>>>sptrembl:Q9WAY7_9VIRU  Q9way7 SubName: Full=ORF2; Flags:
         Fragment;. 2/2010
         Length = 138
 Score = 52.0 bits (123), Expect = 2e-05,  Method: Compositional matrix adjust.
 Identities = 23/23 (100%), Positives = 23/23 (100%)
Query: 1   GAEGEFTHRSQGAIRARDWPGYG 23
           GAEGEFTHRSQGAIRARDWPGYG
Sbjct: 15  GAEGEFTHRSQGAIRARDWPGYG 37

Q9WAY7_9VIRU              Unreviewed;       138 AA.
AC   Q9WAY7;
DT   01-NOV-1999, integrated into UniProtKB/TrEMBL.
DT   01-NOV-1999, sequence version 1.
DT   09-FEB-2010, entry version 23.
DE   SubName: Full=ORF2;
DE   Flags: Fragment;
OS   Torque teno virus.
OC   Viruses; ssDNA viruses; Anelloviridae; unclassified Anelloviridae.
OX   NCBI_TaxID=68887;
RN   [1]
RP   NUCLEOTIDE SEQUENCE.
RC   TISSUE=Serum;
RX   MEDLINE=99335592; PubMed=10405352; DOI=10.1006/viro.1999.9797;
RA   Hijikata M., Takahashi K., Mishiro S.;
RT   "Complete circular DNA genome of a TT virus variant (isolate name
RT   SANBAN) and 44 partial ORF2 sequences implicating a great degree of
RT   diversity beyond genotypes.";
RL   Virology 260:17-22(1999).
CC   -----------------------------------------------------------------------
CC   Copyrighted by the UniProt Consortium, see http://www.uniprot.org/terms
CC   Distributed under the Creative Commons Attribution-NoDerivs License
CC   -----------------------------------------------------------------------
```

FIG. 14E Cont'

```
DR   EMBL; AB024348; BAA77415.1; -; Genomic_DNA.
DR   InterPro; IPR004118; Gyrovir_VP2/TT_ORF2.
DR   InterPro; IPR013267; TTV_ORF2a.
DR   Pfam; PF02957; TT_ORF2; 1.
DR   Pfam; PF08197; TT_ORF2a; 1.
PE   4: Predicted;
FT   NON_TER        1       1
FT   NON_TER      138     138
SQ   SEQUENCE    138 AA;   15416 MW;   93F7D9685085141D CRC64;
     SGEATEGDLR VPRAGAEGEF THRSQGAIRA RDWPGYGQGS EKSMFIGRHY RKKRALSLCA
     VRTTKKACKL LIVMWTPPRN DQQYLNWQWY SSVLSSHAAM CGCFDAVAHF NHLAAVLRAP
     QNPPPPGPQR NLPLRRLP
```

FIG. 14F zkb5.3.pep
nucleotide 3-71
Length: 23aa

```
GAVGEFTHRS QGAIRARDWP GYG
```

BlastP2 of: zkb5.3.pep
compared to database: uniprot

```
>>>sptrembl:Q98Y39_9VIRU  Q98y39  SubName: Full=ORF2;. 2/2010                49   1e-04
>>>sptrembl:Q9WAY7_9VIRU  Q9way7  SubName: Full=ORF2; Flags: Fragm...         49   1e-04
>>>sptrembl:Q9JGT0_9VIRU  Q9jgt0  SubName: Full=PORF2a;. 12/2009              49   1e-04
>>>sptrembl:O90363_9VIRU  O90363  SubName: Full=ORF2 protein;. 2/2010         49   1e-04
>>>sptrembl:Q9JG33_9VIRU  Q9jg33  SubName: Full=Putative uncharact...         49   1e-04
>>>sptrembl:Q786D4_9VIRU  Q786d4  SubName: Full=ORF2;. 2/2010                 49   1e-04
>>>sptrembl:O70738_9VIRU  O70738  SubName: Full=ORF2, ORF1 genes;....         49   1e-04
>>>sptrembl:Q9YKL2_9VIRU  Q9ykl2  SubName: Full=ORF2 protein;. 2/2010         49   1e-04
>>>sptrembl:Q9WFY6_9VIRU  Q9wfy6  SubName: Full=ORF2;. 2/2010                 49   1e-04
>>>sptrembl:Q9JGS7_9VIRU  Q9jgs7  SubName: Full=PORF2a;. 12/2009              49   2e-04
>>>sptrembl:Q9DYC0_9VIRU  Q9dyc0  SubName: Full=Putative uncharact...         49   2e-04
>>>sptrembl:Q9W7S4_9VIRU  Q9w7s4  SubName: Full=Putative uncharact...         49   2e-04
>>>sptrembl:Q77S01_9VIRU  Q77s01  SubName: Full=Putative uncharact...         49   2e-04
>>>sptrembl:Q9JGS4_9VIRU  Q9jgs4  SubName: Full=PORF2a;. 12/2009              48   3e-04
>>>sptrembl:Q9JGT3_9VIRU  Q9jgt3  SubName: Full=PORF2a;. 12/2009              48   3e-04
>>>sptrembl:Q9YR02_9VIRU  Q9yr02  SubName: Full=Putative uncharact...         47   7e-04

>>>>sptrembl:Q98Y39_9VIRU  Q98y39  SubName: Full=ORF2;. 2/2010
           Length = 202
 Score = 49.3 bits (116),  Expect = 1e-04,   Method: Compositional matrix adjust.
 Identities = 22/23 (95%), Positives = 22/23 (95%)
Query:  1  GAVGEFTHRSQGAIRARDWPGYG 23
           GA GEFTHRSQGAIRARDWPGYG
Sbjct: 24  GAEGEFTHRSQGAIRARDWPGYG 46
```

Q98Y39_9VIRU              Unreviewed;         202 AA.
```
AC   Q98Y39;
DT   01-JUN-2001, integrated into UniProtKB/TrEMBL.
DT   01-JUN-2001, sequence version 1.
DT   09-FEB-2010, entry version 17.
DE   SubName: Full=ORF2;
OS   Torque teno virus.
OC   Viruses; ssDNA viruses; Anelloviridae; unclassified Anelloviridae.
OX   NCBI_TaxID=68887;
RN   [1]
RP   NUCLEOTIDE SEQUENCE.
RC   STRAIN=TWH;
```

FIG. 14F Cont'

```
RA   He H.-T., Luo K.-X., Xiao H., Liu D.-X.;
RT   "Complete circular genome of TT virus isolated from feces of a
RT   hepatitis patient.";
RL   Submitted (FEB-2001) to the EMBL/GenBank/DDBJ databases.
CC   -----------------------------------------------------------------------
CC   Copyrighted by the UniProt Consortium, see http://www.uniprot.org/terms
CC   Distributed under the Creative Commons Attribution-NoDerivs License
CC   -----------------------------------------------------------------------
DR   EMBL; AF351132; AAK29446.1; -; Genomic_DNA.
DR   InterPro; IPR004118; Gyrovir_VP2/TT_ORF2.
DR   InterPro; IPR013267; TTV_ORF2a.
DR   Pfam; PF02957; TT_ORF2; 1.
DR   Pfam; PF08197; TT_ORF2a; 1.
PE   4: Predicted;
SQ   SEQUENCE   202 AA;  21437 MW;  105B9ED104956EDE CRC64;
     MAEFSTPVRS GEATEGDHRV PRAGAEGEFT HRSQGAIRAR DWPGYGQGSE KSMFIGRHYR
     KKRALSLCAV RTTKKACKLL IVMWTPPRND QQYLNWQWYS SVLSSHASMC GCPDAVAHLI
     NLASVLRAPQ NPPPPGPQRN LPLRRLPALP AAPEAPGDRA PWPMAGGAEG ENGGAGGDAD
     HGGAAGGPED ANLLDAVAAA ET
//
```

FIG. 14G

```
zkb69.1.pep
nucleotide 1-71
Length: 23aa

RVPEVSLHTA VKGQFGLGTG RAM

BlastP2 of:  zkb69.1.pep    from: 1 to: 23
compared to database: uniprot
>>>sptrembl:Q9WAZ2_9VIRU  Q9waz2 SubName: Full=ORF2; Flags: Fragm...   49   1e-04
>>>sptrembl:Q9WB10_9VIRU  Q9wb10 SubName: Full=ORF2; Flags: Fragm...   49   1e-04
>>>sptrembl:O70807_9VIRU  O70807 SubName: Full=Putative uncharact...   49   2e-04
>>>sptrembl:Q9WAY4_9VIRU  Q9way4 SubName: Full=ORF2; Flags: Fragm...   49   2e-04
>>>sptrembl:Q9WSW0_9VIRU  Q9wsw0 SubName: Full=ORF2; Flags: Fragm...   48   3e-04
>>>sptrembl:Q9WB12_9VIRU  Q9wb12 SubName: Full=ORF2; Flags: Fragm...   48   4e-04
>>>sptrembl:Q9WSW2_9VIRU  Q9wsw2 SubName: Full=ORF2; Flags: Fragm...   48   4e-04
>>>sptrembl:Q9WSW4_9VIRU  Q9wsw4 SubName: Full=ORF2; Flags: Fragm...   47   7e-04
>>>sptrembl:Q9WB09_9VIRU  Q9wb09 SubName: Full=ORF2; Flags: Fragm...   47   9e-04
>>>sptrembl:Q9WSX0_9VIRU  Q9wsx0 SubName: Full=ORF2; Flags: Fragm...   46   0.001
>>>sptrembl:Q9WB02_9VIRU  Q9wb02 SubName: Full=ORF2; Flags: Fragm...   45   0.002
>>>sptrembl:Q9WSW6_9VIRU  Q9wsw6 SubName: Full=ORF2; Flags: Fragm...   45   0.002
>>>sptrembl:B3FWR6_9VIRU  B3fwr6 SubName: Full=ORF2; Flags: Fragm...   38   0.34

>>>>sptrembl:Q9WAZ2_9VIRU  Q9waz2 SubName: Full=ORF2; Flags:
         Fragment;. 2/2010
         Length = 152
 Score = 49.3 bits (116),  Expect = 1e-04,   Method: Compositional matrix adjust.
 Identities = 23/23 (100%), Positives = 23/23 (100%)
Query: 1   RVPEVSLHTAVKGQFGLGTGRAM 23
           RVPEVSLHTAVKGQFGLGTGRAM
Sbjct: 14  RVPEVSLHTAVKGQFGLGTGRAM 36

Q9WAZ2_9VIRU              Unreviewed;       152 AA.
AC   Q9WAZ2;
DT   01-NOV-1999, integrated into UniProtKB/TrEMBL.
DT   01-NOV-1999, sequence version 1.
DT   09-FEB-2010, entry version 23.
DE   SubName: Full=ORF2;
```

FIG. 14G Cont'

```
DE   Flags: Fragment;
OS   Torque teno virus.
OC   Viruses; ssDNA viruses; Anelloviridae; unclassified Anelloviridae.
OX   NCBI_TaxID=68887;
RN   [1]
RP   NUCLEOTIDE SEQUENCE.
RC   TISSUE=Serum;
RX   MEDLINE=99335592; PubMed=10405352; DOI=10.1006/viro.1999.9797;
RA   Hijikata M., Takahashi K., Mishiro S.;
RT   "Complete circular DNA genome of a TT virus variant (isolate name
RT   SANBAN) and 44 partial ORF2 sequences implicating a great degree of
RT   diversity beyond genotypes.";
RL   Virology 260:17-22(1999).
CC   -----------------------------------------------------------------------
CC   Copyrighted by the UniProt Consortium, see http://www.uniprot.org/terms
CC   Distributed under the Creative Commons Attribution-NoDerivs License
CC   -----------------------------------------------------------------------
DR   EMBL; AB024353; BAA77420.1; -; Genomic_DNA.
DR   InterPro; IPR004118; Gyrovir_VP2/TT_ORF2.
DR   Pfam; PF02957; TT_ORF2; 1.
PE   4: Predicted;
FT   NON_TER       1      1
FT   NON_TER     152    152
SQ   SEQUENCE   152 AA;  16658 MW;  1DEC53175C043A17 CRC64;
     ARTPRRGVRA SRGRVPEVSL HTAVKGQFGL GTGRAMGKAL KKAMFLGRIY RKKRRLPLSP
     LHSPPKARKL LRGMWRPPTQ NVSGQERSWY DSVFYSHAAF CGCGDCVGHL SYLATHLGRP
     PSAQPPPQLQ PPVIRRLPAL PAPPNPSGDR AA
```

FIG. 14H

```
zkb69.3.pep
nucleotide 3-71
Length: 23

GAGGEFTHRS QGAIRARDWP GYG

BlastP2 of: zkb69.3.pep    from: 1 to: 23
compared to database: uniprot   ..
>>>sptrembl:Q9JGT3_9VIRU  Q9jgt3 SubName: Full=PORF2a;. 12/2009          50    5e-05
>>>sptrembl:Q9JGS4_9VIRU  Q9jgs4 SubName: Full=PORF2a;. 12/2009          50    5e-05
>>>sptrembl:Q98Y39_9VIRU  Q98y39 SubName: Full=ORF2;.   2/2010           49    1e-04
>>>sptrembl:Q9WAY7_9VIRU  Q9way7 SubName: Full=ORF2; Flags: Fragm...     49    1e-04
>>>sptrembl:Q9YR02_9VIRU  Q9yr02 SubName: Full=Putative uncharact...     49    1e-04
>>>sptrembl:Q786D4_9VIRU  Q786d4 SubName: Full=ORF2;.   2/2010           49    1e-04
>>>sptrembl:O70738_9VIRU  O70738 SubName: Full=ORF2, ORF1 genes;....     49    1e-04
>>>sptrembl:Q9JG33_9VIRU  Q9jg33 SubName: Full=Putative uncharact...     49    2e-04
>>>sptrembl:O90363_9VIRU  O90363 SubName: Full=ORF2 protein;. 2/2010     49    2e-04
>>>sptrembl:Q9JGT0_9VIRU  Q9jgt0 SubName: Full=PORF2a;. 12/2009          49    2e-04
>>>sptrembl:Q9YKL2_9VIRU  Q9ykl2 SubName: Full=ORF2 protein;. 2/2010     49    2e-04
>>>sptrembl:Q9WFY6_9VIRU  Q9wfy6 SubName: Full=ORF2;.   2/2010           49    2e-04
>>>sptrembl:Q9JGS7_9VIRU  Q9jgs7 SubName: Full=PORF2a;. 12/2009          48    3e-04
>>>sptrembl:Q9DYC0_9VIRU  Q9dyc0 SubName: Full=Putative uncharact...     48    3e-04
>>>sptrembl:Q9W7S4_9VIRU  Q9w7s4 SubName: Full=Putative uncharact...     48    3e-04
>>>sptrembl:Q77S01_9VIRU  Q77s01 SubName: Full=Putative uncharact...     48    3e-04
>>>sptrembl:B3FWR5_9VIRU  B3fwr5 SubName: Full=ORF2; Flags: Fragm...     34    5.2
>>>sptrembl:B6SFP1_9VIRU  B6sfp1 SubName: Full=ORF2; Flags: Fragm...     34    5.6

>>>>sptrembl:Q9JGT3_9VIRU  Q9jgt3 SubName: Full=PORF2a;. 12/2009
          Length = 49
 Score = 50.4 bits (119), Expect = 5e-05,   Method: Compositional matrix adjust.
 Identities = 23/23 (100%), Positives = 23/23 (100%)
Query: 1   GAGGEFTHRSQGAIRARDWPGYG 23
           GAGGEFTHRSQGAIRARDWPGYG
```

```
Sbjct: 24 GAGGEFTHRSQGAIRARDWPGYG 46

Q9JGT3_9VIRU            Unreviewed;       49 AA.
AC   Q9JGT3;
DT   01-OCT-2000, integrated into UniProtKB/TrEMBL.
DT   01-OCT-2000, sequence version 1.
DT   15-DEC-2009, entry version 17.
DE   SubName: Full=PORF2a;
GN   Name=ORF2a;
OS   Torque teno virus.
OC   Viruses; ssDNA viruses; Anelloviridae; unclassified Anelloviridae.
OX   NCBI_TaxID=68887;
RN   [1]
RP   NUCLEOTIDE SEQUENCE.
RX   MEDLINE=20417334; PubMed=10963344; DOI=10.1007/s007050070097;
RA   Tanaka Y., Orito E., Ohno T., Nakano T., Hayashi K., Kato T.,
RA   Mukaide M., Iida S., Mizokami M.;
RT   "Identification of a novel 23kDa protein encoded by putative open
RT   reading frame 2 of TT virus (TTV) genotype 1 different from the other
RT   genotypes.";
RL   Arch. Virol. 145:1385-1398(2000).
CC   -----------------------------------------------------------------------
CC   Copyrighted by the UniProt Consortium, see http://www.uniprot.org/terms
CC   Distributed under the Creative Commons Attribution-NoDerivs License
CC   -----------------------------------------------------------------------
DR   EMBL; AB030486; BAA90401.1; -; Genomic_DNA.
DR   InterPro; IPR013267; TTV_ORF2a.
DR   Pfam; PF08197; TT_ORF2a; 1.
PE   4: Predicted;
SQ   SEQUENCE   49 AA;  5118 MW;  596E44680A5D863A CRC64;
     MAEFSTPVRS EGATEGIPNV PRAGAGGEFT HRSQGAIRAR DWPGYGQGS
```

FIG. 14H Cont'

SEQUENCE LISTING

```
<160> NUMBER OF SEQ ID NOS: 49

<210> SEQ ID NO 1
<211> LENGTH: 71
<212> TYPE: DNA
<213> ORGANISM: artificial sequence
<220> FEATURE:
<223> OTHER INFORMATION: zyb2
```

```
<400> SEQUENCE: 1
cgggtgccga aggtgagttt acacaccgca gtcaaggggc aattcgggct cgggactggc 60
cgggccatgg g 71

<210> SEQ ID NO 2
<211> LENGTH: 71
<212> TYPE: DNA
<213> ORGANISM: artificial sequence
<220> FEATURE:
<223> OTHER INFORMATION: zyb9

<400> SEQUENCE: 2
cgggtgccga aggtgagttt acacaccgca gtcaaggggc aattcgggct cgggactggc 60
cgggctatgg g 71

<210> SEQ ID NO 3
<211> LENGTH: 71
<212> TYPE: DNA
<213> ORGANISM: artificial sequence
<220> FEATURE:
<223> OTHER INFORMATION: zkb5

<400> SEQUENCE: 3
cgggtgccgt aggtgagttt acacaccgca gtcaaggggc aattcgggct cgggactggc 60
cgggctatgg g 71

<210> SEQ ID NO 4
<211> LENGTH: 71
<212> TYPE: DNA
<213> ORGANISM: artificial sequence
<220> FEATURE:
<223> OTHER INFORMATION: zkb69

<400> SEQUENCE: 4
cgggtgccgg aggtgagttt acacaccgca gtcaaggggc aattcgggct cgggactggc 60
cgggctatgg g 71

<210> SEQ ID NO 5
<211> LENGTH: 2227
<212> TYPE: DNA
<213> ORGANISM: artificial sequence
<220> FEATURE:
<223> OTHER INFORMATION: chimeric TTV, WV13038 clone 6

<400> SEQUENCE: 5
caattcgtgc acgggactac aaggaaaggg gttgaccccc accctccccc gccatgccca 60
ggagggtgca gacacaactg ggaaggtgct agagaccccg gggggaggct gggccagcac 120
```

```
caggcattgg ggggcaggtt cccgtctcta caccccagcc ccaggcggac agcgcgtgcc 180
cctcccgctg ccccacctgt cacccacctg ctggccccgg gctgtctctg ctcctggctc 240
ccctcccagc tgcgtcccca gctgcctctc cagggaggag tgacagctgg cctgtgccac 300
accctcgagc ccccccggac taccccctcc ctggggcagg acccctgcct gtggcacaac 360
caaggggcct gctgatgggg gctcatgtga gcagtgcccc agctgtgggt gtgggtgctg 420
ccagctgcca ccgcctttgc cctggtttcc cagatagacc ccgacccaca ctccgaagct 480
gtatcatgaa cgctgtggtg ggcggctggt ggggagcggg gttgccgtcc cactaccctc 540
tggaagcctc agccatgaag ggcccctgtg ggcacctttt cccggcacac ggtgctgtgt 600
ttctccactc ttgggctctg cagtgacttg aggggtcaag tctatgatcc cacgggaggc 660
```

| | |
|---|---|
| tgggctaatg aggggaccag agacctcagt gctgtgcagg gagtcctgaa ccaccctggt | 720 |
| ggaaggccca gcccaactcc ccagtcctcc cgccagctcc ctgtggtgtc caggagacct | 780 |
| gtggtcaggc ctggaggaga agctcctcct ccccctcgaca tcctccctgc agcccttgct | 840 |
| cttcaccaga gcctcctgac tccccaggac cccagagagg actgaccctc tccagccgac | 900 |
| ctctgggctc aggacagctg gcggggcag ccacaggagc tgcctgtagg gagcagagtc | 960 |
| aggacgggga ccgagccgga cacccattct ggaagtgtct gcacttccag caggggaag | 1020 |
| gacggcagtg ggtagctggg agtgctgggc cgaagatggg cattgtcagg ccctcagtgg | 1080 |
| ggactgggag gtagaggtgg ggaggtctgt ggaggaagga gaagaagggc cagtgtcccg | 1140 |
| agttgggggt ggttggcagt ggacgaggcc gacaggaaca gacctgagct tggggagctc | 1200 |
| cactcagaac gaggcatcct tcaggttct gtgcatactg gtgtccctgg ctggggccg | 1260 |
| ggccccgaag tggagcctgg gactgtgagg gtggggggg tgtgctgggg tgggaggtgg | 1320 |
| atggagcccc ccctccaccg cctggccgct tgggctgaac cttggacttc ggagccggaa | 1380 |
| cagacatagg aaatggccta actgcatttg cgcaggaaca ccaaatccct cgcagctgca | 1440 |
| cggggctgag ccaggccac gggcggggtc ggccatccca gagtcctgac agctccgtgg | 1500 |
| tgtatgccaa gggcctggg ccgctgaccg aggggcgcct ttcccaggcc agaggccccc | 1560 |
| accccacccc aggagagctg ccccccttttc agttcccaga acggagcccg gctgtggaat | 1620 |
| agtgatgcgg tgaggtcatg gggaggggc ccgcatgact catatcctgg ggtaggggaa | 1680 |
| agggaggaga cggagaaggg gcccagaggc ctccacgtcc tcagctctgc tgggtcagag | 1740 |
| gccaggggct ggcggggctt ctccccagca ctgggtttta ggggagacac caggagatgc | 1800 |
| ttactctgca tccccactct gtcccccagg cccctagcca gggagagctc agtcagagtg | 1860 |
| atcctccagg ggcccagctc tgcatggatg atgttcccag agtacacacc tgggcctcgt | 1920 |
| gccagggccg gcaccgccgt tgtcagggct atggcaaggc aaacagtcaa tgtttgcctc | 1980 |
| actaaagtga ggctgcagca ccctgaaggg atccctggag ggggacgtgg tcccttgtt | 2040 |
| cccaagcttg tctgcacatg cacgtggatg tcaagggttc ccgtgtgtga gcacatgcat | 2100 |
| atttgtatgt gcatggggtg cgggcatgtg tgcctgtgtg gccggagcgt gggctcgtgg | 2160 |
| agaatgtgtg tgagttgggt gtgcacctgc atgtgcccca ggcctaggga gtcccgtgcc | 2220 |
| cgaattg | 2227 |

<210> SEQ ID NO 6
<211> LENGTH: 883
<212> TYPE: DNA
<213> ORGANISM: artificial sequence
<220> FEATURE:
<223> OTHER INFORMATION: chimeric TTV, gb40.27

<400> SEQUENCE: 6

| | |
|---|---|
| cgggactggc cgggctatgc cccagacaca ctcacgtagg ggtgtccggc ctggcagccc | 60 |
| aggaccatgg tctgcagggt ttcctctcgg ccattcagga caaccctagt ctccagggaa | 120 |
| tagcgctggt gtcgcctatc agccgtgaag gtctcctgca ggaggaggct ctgcgggatg | 180 |
| ggcaggtgca atgggtgcct ggtgtgcaga gggaaaaaca ggccaaagcc attaaagcag | 240 |
| ctggcagtgc caggggacaa ttgtgcccca cggtctcagc ctgggcctgt cacgagcttg | 300 |
| cagagttaag actctgccac agagaagaga acatcaggac acctggcagc cctatgcttt | 360 |
| acaatgtgga atccagaacc cttcaccacc tcactgtgcc agagaagtgg gcatggctgg | 420 |
| ggtccccgtc gccatttgac agcaaagacc caagaggata gatgacacac agcatctggt | 480 |

```
gtcacacaga ctgggattag aatccaggca cggtctttca ctagctgtgt gaccttggga      540
aaaggacttg actgttctgt gcctcagttt ccccatctgt aaaacggagg ctaaaataat      600
actgatcgga cacagtggtc agggttagag ataacataca tgaaacgacc acaagctccc      660
caagggcaaa ggtttctgac attccggttc tctgccattt tccatgtgcc cagaagagca      720
cttggtccat agtatgtgct caatgaatgt aaatgggata aaaacacgaa cgaacactct      780
gccaacgatg ctgctgttcc tttgtcatca ctgcttctgt ttaggctgta gctgacttat      840
ctaaggccat acagctgctc aatgcatagc ccggccagtc ccg                       883
```

<210> SEQ ID NO 7
<211> LENGTH: 291
<212> TYPE: DNA
<213> ORGANISM: artificial sequence
<220> FEATURE:
<223> OTHER INFORMATION: chimeric TTV, gb43.30

<400> SEQUENCE: 7

```
ccccttgact tcggtgtgta aacttgtggt atagaacatg atgttttaag atacatgtac       60
attgtggaat ggcttgatca tgctaattaa catatgaatt acctcactta gctatctttt      120
ttatggtgaa agcacttaaa atctaccctc agcagttttc aagtacacaa tacatttcta      180
ttaactatag tcaccatgtt gtacaataaa tctcttgaat ttattcctcc tgcctaactg      240
acattttgta tcctttgact gatctctctc cccagtcccg tgcccgaatt g              291
```

<210> SEQ ID NO 8
<211> LENGTH: 293
<212> TYPE: DNA
<213> ORGANISM: Homo sapiens

<400> SEQUENCE: 8

```
taattgacaa aacgtgtata aacttgtggt atagaacatg atgttttaag atacatgtac       60
attgtggaat ggcttgatca tgctaattaa catatgaatt acctcactta gctatctttt      120
ttatggtgaa agcacttaaa atctaccctc agcagttttc aagtacacaa tacatttcta      180
ttaactatag tcaccatgtt gtacaataaa tctcttgaat ttattcctcc tgcctaactg      240
acattttgta tcctttgact gatctctctc cccagtcccg tgaccagtgc cct            293
```

<210> SEQ ID NO 9
<211> LENGTH: 269
<212> TYPE: DNA
<213> ORGANISM: artificial sequence
<220> FEATURE:
<223> OTHER INFORMATION: gbDhDi43.30.sequence

<400> SEQUENCE: 9

```
gtgtgtaaac ttgtggtata gaacatgatg ttttaagata catgtacatt gtggaatggc       60
ttgatcatgc taattaacat atgaattacc tcacttagct atcttttta tggtgaaagc      120 acttaaaatc taccctcagc agttttcaag tacacaatac atttctatta actatagtca      180
ccatgttgta caataaatct cttgaattta ttcctcctgc ctaactgaca ttttgtatcc      240
tttgactgat ctctctcccc agtcccgtg                                       269
```

<210> SEQ ID NO 10
<211> LENGTH: 269
<212> TYPE: DNA
<213> ORGANISM: Homo sapiens -continued

```
<400> SEQUENCE: 10
tttaagtgta taaacttgtg gtatagaaca tgatgtgata catgtacatt gtggaatggc    60
ttgatcatgc taattaacat atgaattacc tcacttagct atcttttta tggtgaaagc    120 acttaaaatc taccctcagc agttttcaag tacacaatac atttctatta actatagtca   180
ccatgttgta caataaatct cttgaattta ttcctcctgc ctaactgaca ttttgtatcc    240
tttgactgat ctctctcccc agtcccgtg                                     269

<210> SEQ ID NO 11
<211> LENGTH: 49
<212> TYPE: PRT
<213> ORGANISM: artificial sequence
<220> FEATURE:
<223> OTHER INFORMATION: FASTA of gbDhDi43.30

<400> SEQUENCE: 11

Met Phe Tyr Thr Thr Ser Leu His Thr Glu Val Lys Gly Gln Phe Gly
1               5                   10                  15

His Gly Thr Gly Glu Arg Asp Gln Ser Lys Asp Thr Lys Cys Gln Leu
            20                  25                  30

Gly Arg Arg Asn Lys Phe Lys Arg Phe Ile Val Gln His Gly Asp Tyr
        35                  40                  45

Ser

<210> SEQ ID NO 12
<211> LENGTH: 119
<212> TYPE: PRT
<213> ORGANISM: artificial sequence
<220> FEATURE:
<223> OTHER INFORMATION: TT virus variant
<220> FEATURE:
<221> NAME/KEY: misc_feature
<222> LOCATION: (23)..(23)
<223> OTHER INFORMATION: Xaa can be any naturally occurring amino acid

<400> SEQUENCE: 12

Ala Gln Thr Gln Arg Arg Val Ile Pro Ala Ser Arg Gly Arg Val Pro
1               5                   10                  15

Glu Val Ser Leu His Thr Xaa Val Lys Gly Gln Phe Gly Leu Gly Thr
            20                  25                  30

Gly Arg Ala Met Gly Lys Ala Leu Lys Lys Asp Met Phe Leu Gly Lys
        35                  40                  45

Leu Tyr Lys Lys Lys Arg Ala Leu Ser Leu His Gly Leu Arg Thr Pro
    50                  55                  60

Glu Ala Lys Pro Pro Ala Met Ser Trp Arg Pro Val His Asn Pro
65                  70                  75                  80

Asn Arg Ile Glu Arg Asn Leu Trp Glu Ala Phe Phe Arg Ile His Ala
                85                  90                  95

Ser Ser Cys Gly Cys Gly His Leu Val Gly His Leu Thr Val Leu Ala
            100                 105                 110

Arg Arg Tyr Gly Ala Pro Pro
        115

<210> SEQ ID NO 13
<211> LENGTH: 639
<212> TYPE: DNA
<213> ORGANISM: artificial sequence
<220> FEATURE:
<223> OTHER INFORMATION: hod11
```

-continued

<400> SEQUENCE: 13

```
cccccttgact gcggtgtgta aagcgcccca gcctgtgcct gcacagtgcc tgtgtggtgt    60
gaacccatga ccaggcctct ggagggaagg aaggttaggc ttagtggaca ccagctttcc   120
taaggtgggt cttagaccaa ctcattaaaa tggcaggatg ggcttttgtg ctgtatttct   180
tgggattttc aagatgcccc acacagcaga agggatgtgc attttttct ctgccctgag    240
ttgtttgata aaaatcagtg acctcgttct ccacttagaa ctcccctgaa ctgcactcgg   300
tgtctaggac tgttggggaa ggaagtgaag agccagcatg tagtctcctc tggactctta   360
caggatctgt ccacctctgg gctctttatg taggggaagg tgtgagctcc tgggagtact   420
cctgatagag gactgtttcc ctgaaaacct cagcagtgtt tgaggcccta gcaggggaa    480
cccagacccc gcctgccaaa gcccctaatc cctcagggct attatcagca gcctaagcgc   540
cttagggtgg ccagagtcca gcccagcaag cagcaaagtc agcagcctcc tcgccctatc   600
ctctccatgc cccggggcac tccagtcccg accgaattg                          639
```

<210> SEQ ID NO 14
<211> LENGTH: 358
<212> TYPE: DNA
<213> ORGANISM: artificial sequence
<220> FEATURE:
<223> OTHER INFORMATION: hodL.VvWw.1.sequence

<400> SEQUENCE: 14

```
tcccctgaac tgcactcggt gtctaggact gttggggaag gaagtgaaga gccagcatgt    60
agtctcctct ggactcttac aggatctgtc cacctctggg ctctttatgt agggggaaggt  120
gtgagctcct gggagtactc ctgatagagg actgtttccc tgaaaacctc agcagtgttt   180
gaggccctag caggggggaac ccagacccg cctgccaaag cccctaatcc ctcagggcta   240
ttatcagcag cctaagcgcc ttagggtggc cagagtccag cccagcaagc agcaaagtca   300
gcagcctcct cgccctatcc tctccatgcc ccggggcact ccagtcccga ccgaattg     358
```

<210> SEQ ID NO 15
<211> LENGTH: 360
<212> TYPE: DNA
<213> ORGANISM: Homo sapiens

<400> SEQUENCE: 15

```
tcccctgaac tgcactcggt gtctaggact gttggggaag gaagtgaaga gccagcatgt    60
agtctcctct ggactcttac aggatctgtc cacctctggg ctctttatgt agggggaaggt  120
gtgagctcct gggagtactc ctgatagagg actgtttccc tgaaaacctc agcagtgttt   180
gaggccctag caggggggaac ccagacccg cctgccaaag cccctaatcc ctcagggcta   240
ttatcagcag cctaagcgcc ttagggtggc cagagtccag cccagcaagc agcaaagtca   300
gcagcctcct cgccctatcc tctccatgcc ccggggcact ccagtcccag ctggctgatc   360
```

<210> SEQ ID NO 16
<211> LENGTH: 288
<212> TYPE: DNA
<213> ORGANISM: artificial sequence
<220> FEATURE:
<223> OTHER INFORMATION: VvWw.1.sequence
<220> FEATURE:
<221> NAME/KEY: misc_feature
<222> LOCATION: (222)..(228)
<223> OTHER INFORMATION: n is a, c, g, or t

<400> SEQUENCE: 16

```
ccccttgact gcggtgtgta aagcgcccca gcctgtgcct gcacagtgcc tgtgtggtgt    60
gaacccatga ccaggcctct ggagggaagg aaggttaggc ttagtggaca ccagctttcc   120
taaggtgggt cttagaccaa ctcattaaaa tggcaggatg ggcttttgtg ctgtatttct   180
tgggattttc aagatgcccc acacagcaga agggatgtgc annnnnnnct ctgccctgag   240
ttgtttgata aaaatcagtg acctcgttct ccacttagaa ctcccctg                288
```

<210> SEQ ID NO 17
<211> LENGTH: 289
<212> TYPE: DNA
<213> ORGANISM: Homo sapiens

<400> SEQUENCE: 17

```
ttcagttagc tgctgtgtgt aaagcgcccc agcctgtgcc tgcacagtgc ctgtgtggtg    60
tgaacccatg accaggcctc tggagggaag gaaggttagg cttagtggac accagctttc   120
ctaaggtggg tcttagacca actcattaaa atggcaggat gggcttttgt gctgtatttc   180
ttgggatttt caagatgccc cacacagcag aagggatgtg catttttttc tctgccctga   240
gttgtttgat aaaaatcagt gacctcgttc tccacttaga actcccctg                289
```

<210> SEQ ID NO 18
<211> LENGTH: 3387
<212> TYPE: DNA
<213> ORGANISM: artificial sequence
<220> FEATURE:
<223> OTHER INFORMATION: hoht33

<400> SEQUENCE: 18

```
aattcggtcg ggactggcag agtgacgctc aggtcagcct gacagcaggg tgattgaagg    60
ggccagatac cccagcaggg cctgaggcca gaacacagca taggctggct ctgatgggtg   120
gaggaggtgg ccaggcatca tctggagctt ggagttgaga acatctgtga ctcctccttc   180
aggagggtgc tctaggagtt gagagcatcc taggtaggac catacatcta cccccatcct   240
agttccctcc agcctctctt ttcagctcca ggtctacctt aagggaccta ggacacctgg   300 gctgggcat aacaggactt ggtttatgt aaaggagctg ggaagagact gagataacag    360
agggctgcaa ggagagagac agagagagaa gaacctgcca gaagaagctc ctcagcaatc   420
cactaagccc tgatctttgc ctcactgcct gtcccttccc atccgctctt ctgctctctc   480
aatctctgcc ttcaagaaat tggtgcata ttggaatagg gaggaataga agcaccctgg    540
gtggagctct gggcttggct gtgcacgagc tttcagtggg tggtttgctg gtctccaaag   600
atgaccctcc attagtcatg cttctcggtg tttgtcctca ggtagtctca tcccatcttg   660
agtctgggct tgcccgtgtga ctcactttaa ccacaagaat gtggcagaaa ggatgttgtg   720
ccagttctag aactaagcct tcagaaagcc tagcaccttc tgcttttagg agcactgagc   780
ccccatgtta gaagtccact tttatactct gctctggaga ctagcagaat tagaaatgca   840
ctgctgaatg ctgctcgaga gactaatgga gaggccatgt gaataaggag gcctgaaact   900
acatggagat agagggccag ccaccccagc accacggctc agctgtgcct cccagccatc   960
tctgccagtc ctccagggct atgagtgaac catcttggat gttctagctc ggtggagccc  1020
ccaggtgatt gcagcctcag ccaccatctg actgtagctg catgagaggc cccagtggg   1080 accagcagga ctgccaagct gagccctgcc caccccacaga actgtgagaa ataaaaaaat  1140
ggttgtttcc ttaagccatt aagttttgga atgatttgtt actcacaatt gataactgat  1200
```

```
acagtctgtc tttagggaaa acaagggata actctgggct ccaggtgtct tctataggat    1260
gaatgggact tggttgctga caagctgaca agtttgagca tgaaactctt tttttttttt    1320
ggagaaggaa ttttgctctt gttatccagg ctggaataca gtggtgcgat ctcggcccaa    1380
ggcaacctct gcctcctggg ttcaagcaat tctcctgcct cagcctcctg agtagctggg    1440
attacaggca cccaccacta cacctggctc tttttttttt ttgtattttt agtagagaca    1500
ggttttcatt atgttggcct ggtcaggttt tgaactcctg acctcaggtg atccacctgc    1560
cttggcctcc taaaatgctg ggattacagg tgtgagccac cgtgcctggc ctgagcatga    1620
aactttatg ctcaaacatt aaagtgtaaa cactcaccag ctcagctgaa taagaacttc     1680
tgggggcaag gcccaggaat ctacagttta gtaagtgccc ccaccactgg accctgggaa    1740
agtggactgc atttgaaaa actctagatc agttgatacc caggagtcct cataacacta    1800
agttgtaata cctcagtgtg aattagtctg atgcagctct tcttagaggt cattgacaga    1860
gggcaagaca tttccaaaag gaaggaatag ccaatatgga atgacaggtg gattggatga    1920
ccctctatta tttagtttca acctgcccct cctgccttcc ctcccacaaa ttcccttca     1980
gatcctccgt cctaatcctc ttcgatagtt cattgttctt ctgcagacag agcagcgaag    2040
tgttatctgt tgtacccact atgactagtt gatggtgcat ggcttccatg gagcagtgct    2100
gtgatccatt agtcatggag cagtgctgtg atccattgtc atgtctgcca tgaacactgg    2160
aaggggcagt ggtaatgaca gcctcttaca tttgccaact ctgcccaaca ttcttcccag    2220
tgttgggaaa gcctttgctt attccattcc ttcttggaaa gctttgttcc tccatttcac    2280
atttttaatt tttctcattt ttatggtgca ccatggatac cacctgtcca tatagctggc    2340
ttctgatttt tccagatgaa agtaatcctt cctctcctaa cctcccatga cacctaacct    2400
ggcactcatt tacggtgttc agctccttct cctgtacgtt ctcattgttc tcctctcatc    2460
ttctccccag gaatggattc cccgccaagg gaggtaccag gtcagtttct tctttgtgca    2520
acagggtgtc cctgatgagc acaaacctgg aacaagtgtt tgtagggctg gtgggcatct    2580
ggttcctctg ggtgttgtgt agcctgagcc ggggggcaaa tgggtgtttg ttttctgaa     2640
gaaggcaggc gttctgtggc agatgtgggt ggaggggtt gggagtagt atcatggaga      2700
ggctgggatc ctatctatct ccttcccctg cttgaagggc aacttgggag aagctcaaga    2760
gggaggagtt gactgcagaa gctgggatac ctgcataact ctcaggttca agcatcactg    2820
ctttagggcc ctgggggcct atgtgtgagt caagaaaggg agatagagag agaagagaga    2880
gagaggagag agagagagag agagagaaga cagaggagag agagagagaa gaaagaggag    2940
agagagagaa gagagagcag agagagagag catgctgtca gtgaggtggc cctaagccct    3000
cttgaaaata acttggaggc actgtggggt ggctctgagg tgctgaggta tacctgtagt    3060
ggggctagga cctttccaac ctgggtctga aggttgaggc aaccttgggt gtacctgctg    3120
gtgagctgag agccctgggg acctttggca gacattccca cccctgcagc ctggagggtt    3180
tgcatgcagt gaggctgtcc tgctcatcac tacgtcctct gggacagcac attgcctgtg    3240
ctgaacaggc attcagttgc gatttgtgga atcagtgttg gtgaggaggg caagtggcaa    3300
cagaaatggg ggtgtgctcc ccccagttcc tcagctacaa tctccatgac cttctacact    3360
gccctgggcc cagtcccgac cgaattg                                        3387
```

<210> SEQ ID NO 19
<211> LENGTH: 1790
<212> TYPE: DNA
<213> ORGANISM: artificial sequence

```
<220> FEATURE:
<223> OTHER INFORMATION: hoht22

<400> SEQUENCE: 19
caattcggtc gggactgggg agctgtgaga aagagaagag aaggtcagat caggaacatt      60
acacagaagt cggcaaaact ggaacgagga gggaaagaaa tgagcgagtc tgacactcag     120
tccatcctag ttcctatcac acagggaggg acattgccat gcacatcccc acagagatgc    180
accgtgtaag gggtcgaggc agatcctgtc cactattgcc agctctgagg tgatcaaatt    240
gtgtctgccc agggtaaccc ggttgaccta aaccaaccca ctcccttgca catcttaggt    300
gttcctgagt cagcaaggct gaggaagcca ctccagccaa aatcccttgt gcgatcttca    360
agccccaatc acaggcaatg acaaggccat gtctggctgg cctcatgggg actgccctcc    420
cctcaccaga cctagaacac aggcaatgct cagcagcgtt ctgagaagag ctgaggtcaa    480
gaactccaac cccacgcaac ccagacctga tacaaacaga cacccatttg cactcctaac    540
ccttgagcct ctatttccag acctcctcac tgggtctcag ctgagaaccc acttttagcc    600
aagcatcttt agttcagagt tcctcgcagt gaggggatcc ctcccctgcc ttgctgtctg    660
tgctgcatcc attatcccct cacaccgtgc tactcagcag gggagaaatg gagccctggg    720
gagccggcac ttttctcttc tgcctcttcc ttgccttgcc tcaggaaggg gaaaaactct    780
gggttgtttt agtttgatcc cctgtcctaa gtgaccacag gaacactagg cagtgagtac    840
atatggattc ttagcagaga gctgacaagt cttcagaaac atagaaaaca tagaagcttt    900
gagtgaggag atcagaatgt aattaggagt ttcttttgga gcaaaccca ccccaagaga     960
gtgagcccaa gttcttgaag gcccacctga gcagatgaca ccagcgtctt cactatggcc   1020
acagttgtgg gtgagccagc cattgtgggg gcagctccac aggtaggact cgtgtcctga   1080
gcagcgcaca tcatccagga caatgggtcc tgagccctgg ccaaactggg catttcctgg   1140
ggctgacatg gcccagccac agcccggctg cctgcagacc acattggcat cattggtgtc   1200
ccagtagtca tcacacacgg tgccccagga gcctcggtat aggacctcca ctcggcctcg   1260
acacctgtcg cctccattca ccagcctcag ggccaaactg gattcagatc ctacagggga   1320
acacaagaac ctttcatcca tccctatcat gaggtcaaga atctaaggta agttccacac   1380
tcagggtact tcctaatgaa ctaagtcacc taggcaggca gtcacctttg catatgacta   1440
cagactaggc ttcatcaccg tgaaagtagc actgataacc tactctgccc aggtctatgg   1500
gtgctcaact tttggggaag cacctgtgac cccagtggat gtgatgggaa tggatgcccc   1560
actccccagt tgggtacaca gaggatggag ctgctcagct ccagatggca ggcccagacc   1620
cctcccttat tcaggagcat ggtcctatct gggatctgac tggcagagta ccagagatgg   1680
cagggatgag gtcccatag gattaggag accccaggg cttgttctga gcccatagat      1740
aaggatcttt tctgaccact tggaacagga tcccagtccc gaccgaattg               1790

<210> SEQ ID NO 20
<211> LENGTH: 18
<212> TYPE: DNA
<213> ORGANISM: artificial sequence
<220> FEATURE:
<223> OTHER INFORMATION: DhDi primer forward

<400> SEQUENCE: 20
caattcgggc acgggact                                                    18

<210> SEQ ID NO 21
```

```
<211> LENGTH: 24
<212> TYPE: DNA
<213> ORGANISM: artificial sequence
<220> FEATURE:
<223> OTHER INFORMATION: DhDi primer reverse

<400> SEQUENCE: 21 cccttgact tcggtgtgta aact                                          24

<210> SEQ ID NO 22
<211> LENGTH: 28
<212> TYPE: DNA
<213> ORGANISM: artificial sequence
<220> FEATURE:
<223> OTHER INFORMATION: cd, primer forward

<400> SEQUENCE: 22
cagcgagaac gccacggagg gagatcct                                     28

<210> SEQ ID NO 23
<211> LENGTH: 28
<212> TYPE: DNA
<213> ORGANISM: artificial sequence
<220> FEATURE:
<223> OTHER INFORMATION: cd; primer reverse

<400> SEQUENCE: 23
cggacgggcg tggaaaactc agccattc                                     28

<210> SEQ ID NO 24
<211> LENGTH: 18
<212> TYPE: DNA
<213> ORGANISM: artificial sequence
<220> FEATURE:
<223> OTHER INFORMATION: DfDg primer forward

<400> SEQUENCE: 24
cgggactggc cgggctat                                                18

<210> SEQ ID NO 25
<211> LENGTH: 19
<212> TYPE: DNA
<213> ORGANISM: artificial sequence
<220> FEATURE:
<223> OTHER INFORMATION: DfDg primer reverse

<400> SEQUENCE: 25
agcccgaatt gccccttga                                               19

<210> SEQ ID NO 26
<211> LENGTH: 3725
<212> TYPE: DNA
<213> ORGANISM: artificial sequence
<220> FEATURE:
<223> OTHER INFORMATION: ttgb33.35
<220> FEATURE:
<221> NAME/KEY: misc_feature
<222> LOCATION: (3580)..(3597)
<223> OTHER INFORMATION: n is a, c, g, or t

<400> SEQUENCE: 26
attttgtgca gcccgccaat ttctgttcaa acagaccaat caggaccttc tacgtgcact    60
tcctggggcg tgtctacgag gtctatataa gcaacagcgg tgacgaatgg tagagttttt   120
cttcgcccgt ccgcggcgag agcgcgagcg aagcgagcga tcgagcgtcc cgtgggcggg   180
tgccgtaggt gagtttacac accgaagtca aggggcaatt cgggcacggg actggccggg   240
```

```
ctatgggcaa ggctcttaaa aaattccccc gctctgctct ccggcaggac acaaagtcat    300
gccgtggaga ccgccggtcc ataacgtgcc aggtagagag aatcaatggt ttgcagcgtt    360
ctttcacggt catgctgctt tctgcgggtg tggtgaccct gttgggcatc ttaacggcat    420
tgctcctcgc tttcctaacg ccggtccacc gagaccacct ccagggctag accagcttaa    480
tcccgagggc ccggcaggtc ccggagggcc ccccgccatc ttgccagctc tgccggcccc    540
ggcagaccct gaaccggcac cacggcgtgg tggtggggca gatggaggcg ccgccgctgg    600
ggccgccgcc gacgcagacc ataccgggta cgaagaagga gacctagaag atcttttcgc    660
cgccgcggcc gaggacgata tgtgagtagg cggaggcgcc gccgctacta caggcgcaga    720
ctgagacggg gcagacgcag agggcgacga agagacaca gacagactct agtagtgagg     780
cagtggcaac ctgacgttgt taaaaagtgt aaaataacag gatggatgcc tcttataatc    840
tgtggctctg gaagcacaca gatgaacttt ataactcaca tggacgatac tcccctatg    900 ggatacacct acgggggcaa ctttgtaaat gtaactttca gtctagaggc catctatgaa    960
caattcctgt accacagaaa caggtggtcc aggtctaacc atgacttaga cctggccaga   1020
taccaaggaa ccactctaaa actttacaga caccaaaccg tggactatat agttagctac   1080
aacagaacag gccccttttac tataagtgaa atgacttaca tgagcacaca cccggctctc  1140
atgctactac aaaacatag aatagttgta cccagcttca gaaccaagcc aaaaggcaaa    1200
agagccataa aaattagaat aagggcccca aaactaatgc tcaccaagtg gtactttaca   1260
aaagacattt gctccatggg cctctttcaa ctaatggcaa cagctgcaga acttacaaac   1320
ccatggctca gagacaccac aaaaagccca gtaattggct tcagagtctt aaaaaacagc   1380
ttatacacat gcctttccaa cttaaaagac caagcaatac aaggtgaaag aaagactgta   1440
caaaatagat tacacccaga aaacctacat ggcacaggac ctaatgctaa aggctgggaa   1500
tacacataca caaaactaat ggcatctaca tactactcag ccaacagaaa cagcacctac   1560
aactggcaaa actatcaaac taactatgca aacacatata caaaatttaa agaaaaaaga   1620
acagcaaact taaacttaat taaagcagaa tacctatatc attaccctaa caatgtcaca   1680
caatctgact ttatattaga ctacacacta acacccgact ggggcatata cagcccctac   1740
tacctaacac ccaccagaat tagcctagac tgggacacac catggacata tgtaagatac   1800
aacccactat cagacaaagg cataggtaac agaatatatg cacagtggtg ctcagaaaaa   1860
tctagtaaat tagacaccac aaagagcaag tgcatactaa gagacttccc actgtgggcc   1920
atggcctatg gctactgtga ctgggtggtg aagtgcacag gagtgtccag tgcttggaca   1980
gacatgagaa tagccattat atgtccctac acagaaccag cacttatagg gtcaacagaa   2040
gacgtaggct tcattccagt aagtgacacc ttttgcaacg gagacatgcc gtttcttgca   2100
ccatacatac ctattacatg gtggattaag tggtacccca tgattacaca ccaaaaggaa   2160
gttcttgagg caatagttaa ctgtggaccg tttgtacccc gagaccaaac ttccccagct   2220
tgggaataac catgggttac aaaatggatt ggaaatgggg cggctctccc ctgccttcac   2280
aggcaatcga cgaccctgc cagaagtcca cccacgaact tcccgacccc gatagacacc    2340
ctcgcatgtt acaagtctct gacccgacaa agctcggacc gaagacagtt tttcacaaat   2400
gggactggag acgtgggatg cttagcaaaa gaagtattaa agagtccaa gaagactcaa    2460 cagacgatga atatgttgca ggacccttac caagaaaaag aaacaagttc gatactcgag   2520
tccaaggccc tccaaccca gaaaagaaa gttacacttt actccaagcc ctccaagagt     2580
```

```
cggggcaaga gagcagctca gaggaccaag aacaagcacc ccaagaaaaa gaggaccaga      2640
aggaagcgct catggagcag ctccagctcc agaaacacca ccagcgagtc ctcaagcgag      2700
gcctcaaact cctcctcgga gacgtgctcc gactccggag aggagtccac tgggacccca      2760
tcctgtccta attcaaggtc ccagtatccc agacctgctt ttccctaaca cacaaaaaaa      2820
aaaacgattt tccaactacg actgggtgtg cgagtacgag ctggccaaat ggatggatcg      2880
gcccttgcgg cactacccat cagaccccc tcactacccc tggctaccaa aaaagcctcc       2940 taccctcct acatgtagag taagtttcaa attaaagctc aatgactaaa attcaaggcc       3000
gtgggtgttt cacttcatcg gtgtctacct ctaaaagtca ctaagcactc cgagcgtaag      3060
cgaggagtgc gacccccctg cccggtagca acttcctcgg ggtccggcgc tacgccttcg      3120
gctgcgccgg cgcctcgga cccccccctcg acccgaatcg ctcgcgcgat tcggacctgc      3180
ggcctcgggg gggtcggggg ctttactaaa cagactctga ggtgccgttg gacactgagg      3240
gggtgaacag caacgaaagt gagtggggcc aaacttcgcc ataaggcctt taactttggg      3300
tcgcttgtca gcagcttccg ggtccgcctg gaggccgcca ttttacattc ggccgccatt      3360
ttaggccctc gcgggcctcc atagtcgcac atcagtgacg tcacggcagc catcttggct      3420
gtgacgtcaa cgtcacgtgg ggaggacggc gtgtaacccg gaagtcatcc tcatcacgcg      3480
acctgacgtc acggccgcca ttttgtgctg tccgccatct tgtgacttcc ttccgctttt      3540
tgtaaaaaaa agaggaagtg tgacgtagcg gcggggggn nnnnnnnnn nnnnnnncgc        3600 caccagggg cgctacgcgc cccccccgc gcatgtgcgg gtccccccc tcggggggg          3660 ctccgccccc ccggccccc cccgggctaa atacaccgcg catgcgcggc cacgccccg        3720 ccgcc                                                                  3725

<210> SEQ ID NO 27
<211> LENGTH: 719
<212> TYPE: DNA
<213> ORGANISM: artificial sequence
<220> FEATURE:
<223> OTHER INFORMATION: zpr4.20

<400> SEQUENCE: 27
caattcgggc acgggactgg ccgggctatg gcaaggctc ttaaaaaatt ccccgctct         60 gctctccggc aggacacaaa gtcatgccgt ggagaccgcc ggtccataac gtgccaggta      120
gagagaatca atggtttgca cgttctttc acggtcatgc tgctttctgc gggtgtggtg      180
accctgttgg gcatcttaac ggcattgctc ctcgctttcc taacgccggt ccaccgagac     240 caccctccagg gctagaccag cttaatcccg agggcccggc aggtcccgga gggccccccg    300
ccatcttgcc agctctgccg gccccggcag accctgaacc ggcaccacgg cgtggtggtg    360
gggcagatgg aggcgccgcc gctggggccg ccgccgacgc agaccatacc gggtacgaag     420
aaggagacct cggggggggc tccgcccccc cggcccccc ccgggctaaa tacaccgcgc      480
atgcgcggcc acgccccgc cgccattttg tgcagcccgc caatttctgt tcaaacagac      540
caatcaggac cttctacgtg cacttcctgg ggcgtgtcta cgaggtctat ataagcaaca     600
gcggtgacga atggtagagt ttttcttcgc ccgtccgcgg cgagagcgcg agcgaagcga      660
gcgatcgagc gtcccgtggg cgggtgccgt aggtgagttt acacaccgaa gtcaagggg       719

<210> SEQ ID NO 28
<211> LENGTH: 3758
<212> TYPE: DNA
<213> ORGANISM: artificial sequence
```

```
<220> FEATURE:
<223> OTHER INFORMATION: tth25

<400> SEQUENCE: 28
aagtacgtca ctaaccacgt gactcccgca ggccaaccag agtctacgtc gtgcacttcc      60
tgggcatggt ctacatcata atataagaac gtgcacttcc gaatggctga gttttccacg     120
cccgtccgca gcgagaacgc cacggaggga gatcctcgcg tcccgagggc gggtgccgga     180
ggtgagttta cacaccgcag tcaagggca  attcgggctc gggactggcc gggcccgggg     240
caaggctctt aaaaaatgcg ttttcgcagg gttgcccaga aaggaaagt  gcttttgcaa     300
actgtgccag ctgcaaagaa ggctaggcgg cttctaggta tgtggcagcc ccccacgcac     360
aatgtcccgg gcatcgagag aaactggtac gagagctgtt ttagatccca cgctgctgtt     420
tgtggctgtg gcgattttgt tggccatctt aatcatctgg caactactct gggtcgtcct     480
ccgcgtcctg gcccccaggc ggaccccgc  acgccgcaaa taagaaacct gccagcgctc     540
ccggcgcccc agggcgagcc cggtgacaga gcgccatggc atggggcttc tggggccgac     600
gccgccggtg gagacgatgg agagcgcggc gcagacggtg gagacccgc  agacgtagga     660
gacgacgccc tactcgccgc tttcgagctc gtcgaagagt aaggaggcgc ggggggaggt     720
ggcgcagacg ctacagaaaa tggcgacggg gcagacgcag acggactcat agaaaaaga     780
tagtcataaa acagtggcaa ccaaactta  taagacgctg ctacgtcata gggtacttac     840
cacttatatt ctgcggcgaa aatacaaccg cccagaactt tgccactcac tcggacgaca     900
tgataagcaa aggaccgtac gggggggca  tgactaccac caaattcact ctgagaatac     960
tgtacgacga gtttaccagg tttatgaact tttggactgt cagtaacgaa gacctagacc    1020
tgtgtagata cgtgggctgc aaactaatat tttttaaaca ccccacggtg gactttatag    1080
tacagataaa cactcagcct cctttcttag acacgcacct caccgcggcc agcatacacc    1140
cgggcatcat gatgctcagc aagagacaca tactaatacc ctctctaaag acccggccca    1200
gcagaaaaca cagggtggtc gtcagggtgg gcgccccaag acttttttcag gacaagtggt    1260
acccccagtc agacctgtgt gacacagttc tgctttccat atttgcaacc gcctgcgact    1320
tgcaatatcc gttcggctca ccactaactg acaacccttg cgtcaacttc cagatcctgg    1380
ggccccagta caaaaaacac cttagtatta gctccactat ggatcaaact aacgaaaacc    1440
attataaaga aaacttattt aacaaaactg aactatacaa cacctttcaa accatagctc    1500
agcttaaaga gacaggacac atttcaggca ttagtcctac ttggaatgaa gtccagaatt    1560
caacaacact tactaaagga ggtgacaatg ccactcagag tagagacact tggtataaag    1620
gaaatacata caacgagaag atatgcgagt tagcacaaat aaccagaaac agatttaaaa    1680
atgcaaccaa aggagcacta ccaaactacc ccacaataat gtccacagac ctatatgaat    1740
accactcagg catacactcc agcatatatc tatcagctgg caggagctac tttgaaacca    1800
ccggggccta ctctgacatt atatacaacc ctttcacaga caaaggcaca ggcaacataa    1860
tctggataga ctacctcaca aaagaagaca ccatttttgt gaaaaacaaa agcaaatgcg    1920
agataatgga catgccccctg tgggcggcct gcacaggata cacagagttt tgtgcaaagt    1980
atacaggcga ctctgccatt atctacaatg caagaatact cataagatgc ccatacactg    2040
agcccatgtt aatagaccac tcagacccaa acaaaagctt cgttccctac tcatttaact    2100
ttggcaacgg aaagatgccc ggaggcagct ccaacgtgcc cataagaatg agagccaagt    2160
ggtacgtgaa catattccac caaaagaag  tattagagag catagtacag tccggaccgt    2220
```

| | |
|---|---|
| ttgggtacaa gggcgacata agatcagctg tactagccat gaaatacaga tttcactgga | 2280 |
| agtggggcgg aaaccctata tccaaacagg tcgtcaggaa tccctgctcc aactccagct | 2340 |
| cctccgcggc ccatagagga cctcgcagcg tacaagcggt tgacccgaaa tacaataccc | 2400 |
| cagaggtcac gtggcactcg tgggacatta gacgaggact cttggcaaa gcaggtatta | 2460 |
| aaagaatgca acaggaatca gatgctcttt acattcctcc aggaccaatc aagagacctc | 2520 |
| gcagggacac caacgcccaa gacccagaag agcaaaacga aagctcaggt ttcagagtcc | 2580 |
| agcagcgact cccgtgggtc cactccagcc aagagacgca aagctcccaa gaagagacgg | 2640 |
| aggcgcaggg gtcggtacaa gaccaactac tcctccagct ccgagagcag cgagttctcc | 2700 |
| gactccagct ccagcaactc gcaacccaag tcctcaaagt ccaagcaggg cacagcctac | 2760 |
| accccctatt atcttcccaa gcataaacaa agcctttatg tttgagcccc agggtcctaa | 2820 |
| acccatacag gggtacaacg actggctaga agagtacact gcttgcaaat tctgggacag | 2880 |
| acccccaga aagctacaca cagacatacc cttctacccc tgggcaccaa accccaaca | 2940 |
| gcaagtcagg gtgtcccttta aactcaactt tcaataaaaa ttctaggccg tgggagtttc | 3000 |
| acttgtcggt gtctgcttct taaggtcgcc aagcactccg agcgccagcg aggagtgcga | 3060 |
| cccccctcc ggtagcaacg ccttcggagc cgcgcgctac gccttcggct gcgcgcggca | 3120 |
| cctcagaccc cccctccacc cgaaacgctt gcgcgtttcg gaccttcggc gtcgggggg | 3180 |
| tcgggagctt tattaaacag actccgagtt gccattggac actggagctg tgaatcagta | 3240 |
| acgaaagtga gtggggccag acttcgccat agggccttta tcttctcgcc attggatagt | 3300 |
| gtccggggtc gccgtaggct tcggcctcgt ttttaggcct tccggactac aaaaatggcg | 3360 |
| gttttagtga cgtcacggcc gccattttaa gtaaggcgga agcagctcca ctttctcaca | 3420 |
| aaatggcggc ggagcacttc cggcttgccc aaaatggcgg gcaagctctt ccgggtaaag | 3480 |
| ggtcagcagc tacgtcacaa gtcacctgac tggggagggg tcacaacccg gaagccctcc | 3540 |
| tcagtcacgt ggctgttcac gtggttgcta cgtcatcggc gccatcttgt gtcgcaaaat | 3600 |
| ggcggacaac ttccgctttt ttaaaaaaag gcgcgaaaaa acggcggcgg cggcgcgcgc | 3660 |
| gctgtgcgcg cgcgccgggg gggcgccagc gccccccccc ccgcgcatgc gcgggtcccc | 3720 |
| cccccgcgg ggggctccgc ccccggccc ccccccg | 3758 |

<210> SEQ ID NO 29
<211> LENGTH: 621
<212> TYPE: DNA
<213> ORGANISM: artificial sequence
<220> FEATURE:
<223> OTHER INFORMATION: zpr9.6

<400> SEQUENCE: 29

| | |
|---|---|
| ccgcagcgag aacgccacgg agggagatcc tcgcgtcccg agggcgggtg ccggaggtga | 60 |
| gtttacacac cgcagtcaag gggcaattcg ggctcgggac tggccgggcc ccgggcaagg | 120 |
| ctcttaaaaa atgcgttttc gcagggttgc ccagaaaagg aaagtgcttt tgcaaactgt | 180 |
| gccagctgca aagaaggcta ggcggcttct aggtatgtgg cagcccccca cgcacaatgt | 240 |
| cccgggcatc gagagaaact ggtacgagag ctgttttaga tcccacgctg ctgtttgtgg | 300 |
| ctgtggcgat tttgttggcc atcttaatca tctggcaact actctgggtc gtcctccgcg | 360 |
| tcctgggccc ccaggcggac cccgcacgcc gcaaataaga aacctgccag cgctcccggc | 420 |
| gccccagggc gagcccggtg acagagcgcc atggcatggg gcttctgggg ccgacgccgc | 480 |
| cggtggagac gatggagagc gcggcgcaga cggtggagac cccgcaggcc aaccagagtc | 540 |

```
tacgtcgtgc acttcctggg catggtctac atcataatat aagaacgtgc acttccgaat    600
ggctgagttt tccacgcccg t                                              621
```

<210> SEQ ID NO 30
<211> LENGTH: 3758
<212> TYPE: DNA
<213> ORGANISM: artificial sequence
<220> FEATURE:
<223> OTHER INFORMATION: ttrh215

<400> SEQUENCE: 30

```
aaagtacgtc actaaccacg tgactcccac aggccaacca cagtctacgt cgtgcatttc     60
ctgggcatgg tctacatcat aatataagaa ggcgcacttc cgaatggctg agttttccac    120
gcccgtccgc agcgagaacg ccacggaggg agatcctcgc gtcccgaggg cgggtgccgg    180
aggtgagttt acacaccgca gtcaaggggc aattcgggct cgggactggc cgggccctgg    240
gcaaggctct taaaaaatgc gctttcgcag ggttgcggag aaaaggaaag tgcttctgca    300
aactctgcga gctgcaaagc aggctaggcg gcttctaggt atgtggcagc ccccgcgca    360 caatgtcccc ggcatcgaga gaaactggta cgagagctgc ttcaggtctc acgctgctgt    420 tgtggctgt ggcgactttg ttggccatat taatcatttg gcaactactc tgggtcgtcc    480
tccgcgtcct gggcccccag gcggaccccg cacgccgcaa ataagaaacc tgccagcgct    540
cccggcgccc cagggcgagc ccggtgacag agcgccatgg cgtggggttt ctggggccga    600
cgccgccggt ggagacggtg gagagcgcgg cgcagacggt ggagaccccg gagacgtagg    660
agacgacgcc ctgctcgccg ctttcgagct cgtcgaagag taaggagacg cggggggagg    720
tggcgcagac gctacagaaa atggcgacgg ggcagacgca gacggactca cagaaaaaag    780
ataattataa aacagtggca accaaacttt attagacgct gctacataat aggatgccta    840
cctctcgttt tctgtggcga aaatacaacc gcccagaact atgccactca ctcagacgat    900
atgataagca aaggaccgta cggggggggc atgactacca cgaaattcac tctgagaata    960
ctgtacgacg agtttaccag gtttatgaac ttttggactg tcagtaacga agacctagac   1020
ctgtgtagat acgtgggctg caaactgata ttttttaaac accccacggt ggactttatg   1080
gtacagataa acactcagcc tcctttctta gacacaagcc tcaccgcggc cagcatacac   1140
ccgggcatca tgatgctcag caagagacgc atattaatac cctctctaaa gacccggccg   1200
agcagaaaac acagggtggt cgtcagggtg ggcgccccaa gactttttca ggacaagtgg   1260
tacccccagt cagacctatg tgacacagtt ctgctttcca tatttgcaac cgcccgcgac   1320
ttgcaatatc cgttcggctc accactaact gacaacccttt gcgtcaactt ccagatcctg   1380 gggcccagt acaaaaaaca ccttagtatt agctccacta tggatgatac taacaaacag   1440
cactataaca gcaacttatt taataaaact gcactataca acacctttca aaccatagcc   1500
cggcttaaag agacaggaca aactgcaaac attagtccaa gttggagtga agtacaaaac   1560
acaaaactac tagatcacac aggtgctaat gcaactgcca gcagagacac ttggtacaag   1620
ggaaacacat acaatgacta catacaacag ttagcagaga aaacaagaga aaggtttaaa   1680
aaagcaacaa tgtcagcact accaaactac cccacaataa tgtccacaga cttatacgaa   1740
taccactcag gcatatactc cagcatattt ctatcagctg caggagcta ctttgaaacc   1800 actggggcct actctgacat tatatacaac cctttgacag acaaaggcac aggcaacata   1860
atctggatag actaccttac aaaagacgac acaatctttg taaaaacaa aagcaaatgt   1920
```

```
gagataatgg acatgcccct gtgggcggcc ggcacaggat acacagagtt ttgtgcaaag    1980
tacacaggag actctgccat tatttacaat gccagaatac tcataagatg cccatacact    2040
gaacccatgc taatagacca ctcagaccca aacaaaggct ttgtaccgta ctcatttaac    2100
tttggcaacg gaaagatgcc gggaggcagc tccaacgtgc ccataagaat gagagccaag    2160
tggtacgtaa acatattcca ccaaaaagaa gtattggaga gcatagtaca gtccggaccg    2220
ttcgggtaca gggcgacat aaaatcagct gtactgtcca tgaaatacag atttcactgg    2280
aaatggggcg gaaaccctat atccaaacag gtcgtcagga atccctgctc caactccagc    2340
acctccgcgg cccatagagg acctcgcagc gtacaagcgg ttgacccgaa atacaatacc    2400
ccagaagtca cttggcactc gtgggacatc agacgaggac tctttggcaa agcaggtatt    2460
aaagaatgc aacaagaatc agatgctctt tacgttcctg caggaccact caagaggcct    2520
cgcagagaca ccaacgccca gacccggaa aagcaaaacg aaagctcacg tttcggagtc    2580
cagcagcgac tcccgtgggt ccactccagc caagagacgc aaagctccga agaagagacg    2640
caggcgcagg ggtcggtaca agaccaacta ctcctccagc tccgagagca gcgagtactc    2700
cgactccagc tccaacaact cgcacccaa gtcctcaaag ttcaagcagg acacagccta    2760
cacccctat tatcctccca agcataaaca aagcctatat gtttgaaccc cagggtccta    2820
aacccataca ggggtacaac gattggctag aggagtacac tagttgcaag ttccgggaca    2880
gaccccgag aatgctacac acagacttac ccttttaccc ctgggcacca aaaccccaag    2940
accaagtcag ggtaaccttt aaactcaact ttcaataaaa attctaggcc gtgggacttt    3000
cacttgtcgg tgtctgcttc ttaaggtcgc caagcactcc gagcgtcagc gaggagtgcg    3060
acccccccc tcggtagcaa cgccttcgga gccgcgcgct acgccttcgg ctgcgcgcgg    3120
cacctcagac ccccctcca cccgaaacgc ttgcgcgttt cggaccttcg gcgtcggggg    3180
ggtcgggagc tttattaaac agactccgag ttgccattgg acactggagc tgtgaatcag    3240
taacgaaagt gagtggggcc agacttcgcc atagggcctt tatcttctcg ccattggata    3300
gtgtccgggg ttgccgtagg cttcggcctc gttttaggc cttccggact acaaaaatgg    3360
cggatttgt gacgtcacgg ccgccatttt aagtaaggcg gaagcagctc caccctctca    3420
cataatggcg gcggagcact cccggcttgc ccaaaatggc gggcaagctc ttccgggtca    3480
aaggttggca gctacgtcac aagtcacctg actggggagg agttacatcc cggaagttct    3540
cctcggtcac gtgactgtac acgtgactgc tacgtcattg acgccatctt gtgtcacaaa    3600
atggcggtgc acttccgctt ttttgaaaaa aggcgcgaaa aaacggcggc ggcggcgcgc    3660
gcgctgcgcg cgcgcgccgg gggggcgcca gcgcccccc ccccgcgcat gcacgggtcc    3720
cccccccac gggggctcc gcccccggc ccccccc                                 3758
```

<210> SEQ ID NO 31
<211> LENGTH: 642
<212> TYPE: DNA
<213> ORGANISM: artificial sequence
<220> FEATURE:
<223> OTHER INFORMATION: zpr12.24

<400> SEQUENCE: 31

```
cagcgagaac gccacggagg gagatcctcg cgtcccgagg gcgggtgccg gaggtgagtt      60
tacacaccgc agtcaagggg caattcgggc tcgggactgg ccgggccccg gcaaggctc     120
ttaaaaaatg cgctttcgca gggttgctga gaaaaggaaa gtgcttctgc aaactgtgcg    180
agctacacag aagactaggc ggcttctaag ccgcccacag gggcatgtct acatgcttcc    240
```

```
gcagcgagaa cgccacggag ggagatcctc gcgtcccgag ggcgggtgcc ggaggtgagt    300
ttacacaccg cagtcaaagg gcaattcggg ctcgggactg gccgggcccc gggcaaggct    360
cttaaaaaat gcgctttcgc ggggttgctg agaaaaggaa agtgcttctg caaactgtgc    420
gagctacaca gaagactagg cggcttctag gtatgtggca gccccccgtg cacaatgtcc    480
ccggcatctt attagtactc tggcgttgta gataatggca gagtctccag tgtactttgc    540
acagaactct gtgtatcctg tgcaggccgc ccacaggggc atgtctacat cataatataa    600
taaggcgcac ttccgaatgg ctgagttttc cacgcccgtc cg                      642
```

```
<210> SEQ ID NO 32
<211> LENGTH: 23
<212> TYPE: PRT
<213> ORGANISM: artificial sequence
<220> FEATURE:
<223> OTHER INFORMATION: zyb2.1. peptide

<400> SEQUENCE: 32

Arg Val Pro Lys Val Ser Leu His Thr Ala Val Lys Gly Gln Phe Gly
1               5                   10                  15

Leu Gly Thr Gly Arg Ala Met
            20

<210> SEQ ID NO 33
<211> LENGTH: 23
<212> TYPE: PRT
<213> ORGANISM: artificial sequence
<220> FEATURE:
<223> OTHER INFORMATION: zyb9.1 peptide

<400> SEQUENCE: 33

Arg Val Pro Lys Val Ser Leu His Thr Ala Val Lys Gly Gln Phe Gly
1               5                   10                  15

Leu Gly Thr Gly Arg Ala Met
            20

<210> SEQ ID NO 34
<211> LENGTH: 23
<212> TYPE: PRT
<213> ORGANISM: artificial sequence
<220> FEATURE:
<223> OTHER INFORMATION: zyb69.1 peptide

<400> SEQUENCE: 34

Arg Val Pro Glu Val Ser Leu His Thr Ala Val Lys Gly Gln Phe Gly
1               5                   10                  15

Leu Gly Thr Gly Arg Ala Met
            20

<210> SEQ ID NO 35
<211> LENGTH: 23
<212> TYPE: PRT
<213> ORGANISM: artificial sequence
<220> FEATURE:
<223> OTHER INFORMATION: zyb2.3. peptide

<400> SEQUENCE: 35

Gly Ala Glu Gly Glu Phe Thr His Arg Ser Gln Gly Ala Ile Arg Ala
1               5                   10                  15

Arg Asp Trp Pro Gly His Gly
            20
```

```
<210> SEQ ID NO 36
<211> LENGTH: 23
<212> TYPE: PRT
<213> ORGANISM: artificial sequence
<220> FEATURE:
<223> OTHER INFORMATION: zyb9.3. peptide

<400> SEQUENCE: 36

Gly Ala Glu Gly Glu Phe Thr His Arg Ser Gln Gly Ala Ile Arg Ala
1               5                   10                  15

Arg Asp Trp Pro Gly Tyr Gly
            20

<210> SEQ ID NO 37
<211> LENGTH: 23
<212> TYPE: PRT
<213> ORGANISM: artificial sequence
<220> FEATURE:
<223> OTHER INFORMATION: zyb5.3. peptide

<400> SEQUENCE: 37

Gly Ala Val Gly Glu Phe Thr His Arg Ser Gln Gly Ala Ile Arg Ala
1               5                   10                  15

Arg Asp Trp Pro Gly Tyr Gly
            20

<210> SEQ ID NO 38
<211> LENGTH: 23
<212> TYPE: PRT
<213> ORGANISM: artificial sequence
<220> FEATURE:
<223> OTHER INFORMATION: zkb69.3 peptide

<400> SEQUENCE: 38

Gly Ala Gly Gly Glu Phe Thr His Arg Ser Gln Gly Ala Ile Arg Ala
1               5                   10                  15

Arg Asp Trp Pro Gly Tyr Gly
            20

<210> SEQ ID NO 39
<211> LENGTH: 23
<212> TYPE: PRT
<213> ORGANISM: artificial sequence
<220> FEATURE:
<223> OTHER INFORMATION: Q9WB09_9Viru

<400> SEQUENCE: 39

Arg Val Pro Lys Val Ser Leu His Thr Glu Val Lys Gly Gln Phe Gly
1               5                   10                  15

Leu Gly Thr Gly Arg Ala Met
            20

<210> SEQ ID NO 40
<211> LENGTH: 204
<212> TYPE: PRT
<213> ORGANISM: artificial sequence
<220> FEATURE:
<223> OTHER INFORMATION: torque teno virus
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (196)..(196)
<223> OTHER INFORMATION: Xaa can be any naturally occurring amino acid
```

<400> SEQUENCE: 40

Cys Thr Ser Glu Trp Leu Ser Phe Pro Arg Pro Ser Ala Ala Ala Xaa
1               5                   10                  15

Pro Arg Arg Val Ile Pro Ala Ser Arg Trp Arg Val Pro Lys Val Ser
                20                  25                  30

Leu His Thr Ala Val Lys Gly Gln Phe Gly Leu Gly Thr Gly Arg Ala
            35                  40                  45

Met Gly Lys Ala Leu Lys Val Phe Ile Leu Lys Met His Phe Ser Arg
    50                  55                  60

Ile Ser Arg Ser Lys Arg Lys Val Leu Leu Pro Ala Leu Pro Ala Pro
65                  70                  75                  80

Pro Pro Pro Arg Gln Leu Leu Met Trp Gln Pro Pro Ile Gln Asn Gly
                85                  90                  95

Thr Gln Leu Asp Arg His Trp Phe Glu Ser Val Trp Arg Ser His Ala
            100                 105                 110

Ala Tyr Cys Gly Cys Gly Asp Cys Val Gly His Leu Gln His Leu Ala
        115                 120                 125

Ala Asn Leu Gly Arg Pro Pro His Pro Gln Pro Pro Arg Glu Gln His
    130                 135                 140

Pro Pro Gln Ile Arg Gly Leu Pro Ala Leu Pro Ala Pro Ser Asn
145                 150                 155                 160

Arg Asn Ser Trp Pro Gly Thr Gly Gly Asp Ala Ala Gly Glu Gln Ala
                165                 170                 175

Gly Gly Ser Arg Gly Ala Gly Asp Gly Gly Asp Gly Glu Leu Ala Asp
            180                 185                 190

Asp Asp Leu Xaa Asp Ala Ala Ala Leu Val Glu Glu
        195                 200

<210> SEQ ID NO 41
<211> LENGTH: 138
<212> TYPE: PRT
<213> ORGANISM: artificial sequence
<220> FEATURE:
<223> OTHER INFORMATION: torque teno virus

<400> SEQUENCE: 41

Ala Val Lys Pro Arg Arg Glu Ile Ser Ala Ser Arg Gly Arg Val Pro
1               5                   10                  15

Lys Val Ser Leu His Thr Glu Val Lys Gly Gln Phe Gly Leu Gly Thr
                20                  25                  30

Gly Arg Ala Met Gly Lys Ala Leu Lys Ser Met Phe Ile Gly Arg
            35                  40                  45

His Tyr Arg Lys Lys Arg Ala Leu Ser Leu Cys Ala Val Arg Thr Thr
    50                  55                  60

Lys Lys Ala Cys Lys Leu Leu Ile Val Met Trp Thr Pro Arg Asn
65                  70                  75                  80

Asp Gln Gln Tyr Leu Asn Trp Gln Trp Tyr Ser Ser Val Leu Ser Ser
                85                  90                  95

His Ala Ala Met Cys Gly Cys Pro Asp Ala Ile Ala His Leu Ser His
            100                 105                 110

Leu Ala Phe Val Phe Arg Ala Pro Gln Asn Pro Pro Pro Gly Pro
        115                 120                 125

Gln Arg Asn Leu Pro Leu Arg Arg Leu Pro
    130                 135

<210> SEQ ID NO 42
<211> LENGTH: 202
<212> TYPE: PRT
<213> ORGANISM: artificial sequence
<220> FEATURE:
<223> OTHER INFORMATION: torque teno virus

<400> SEQUENCE: 42

```
Met Ala Glu Phe Ser Thr Pro Val Arg Ser Gly Glu Ala Thr Glu Gly
1               5                   10                  15

Asp His Arg Val Pro Arg Ala Gly Ala Glu Gly Glu Phe Thr His Arg
            20                  25                  30

Ser Gln Gly Ala Ile Arg Ala Arg Asp Trp Pro Gly Tyr Gly Gln Gly
        35                  40                  45

Ser Glu Lys Ser Met Phe Ile Gly Arg His Tyr Arg Lys Lys Arg Ala
    50                  55                  60

Leu Ser Leu Cys Ala Val Arg Thr Thr Lys Lys Ala Cys Lys Leu Leu
65                  70                  75                  80

Ile Val Met Trp Thr Pro Pro Arg Asn Asp Gln Gln Tyr Leu Asn Trp
                85                  90                  95

Gln Trp Tyr Ser Ser Val Leu Ser Ser His Ala Ser Met Cys Gly Cys
            100                 105                 110

Pro Asp Ala Val Ala His Leu Ile Asn Leu Ala Ser Val Leu Arg Ala
        115                 120                 125

Pro Gln Asn Pro Pro Pro Gly Pro Gln Arg Asn Leu Pro Leu Arg
    130                 135                 140

Arg Leu Pro Ala Leu Pro Ala Ala Pro Glu Ala Pro Gly Asp Arg Ala
145                 150                 155                 160

Pro Trp Pro Met Ala Gly Gly Ala Glu Gly Glu Asn Gly Gly Ala Gly
                165                 170                 175

Gly Asp Ala Asp His Gly Gly Ala Ala Gly Gly Pro Glu Asp Ala Asn
            180                 185                 190

Leu Leu Asp Ala Val Ala Ala Ala Glu Thr
        195                 200
```

<210> SEQ ID NO 43
<211> LENGTH: 204
<212> TYPE: PRT
<213> ORGANISM: artificial sequence
<220> FEATURE:
<223> OTHER INFORMATION: torque teno virus
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (196)..(196)
<223> OTHER INFORMATION: Xaa can be any naturally occurring amino acid

<400> SEQUENCE: 43

```
Cys Thr Ser Glu Trp Leu Ser Phe Pro Arg Pro Ser Ala Ala Ala Xaa
1               5                   10                  15

Pro Arg Arg Val Ile Pro Ala Ser Arg Trp Arg Val Pro Lys Val Ser
            20                  25                  30

Leu His Thr Ala Val Lys Gly Gln Phe Gly Leu Gly Thr Gly Arg Ala
        35                  40                  45

Met Gly Lys Ala Leu Lys Val Phe Ile Leu Lys Met His Phe Ser Arg
    50                  55                  60
```

Ile Ser Arg Ser Lys Arg Lys Val Leu Leu Pro Ala Leu Pro Ala Pro
65                  70                  75                  80

Pro Pro Pro Arg Gln Leu Leu Met Trp Gln Pro Ile Gln Asn Gly
            85                  90                  95

Thr Gln Leu Asp Arg His Trp Phe Glu Ser Val Trp Arg Ser His Ala
        100                 105                 110

Ala Tyr Cys Gly Cys Gly Asp Cys Val Gly His Leu Gln His Leu Ala
        115                 120                 125

Ala Asn Leu Gly Arg Pro His Pro Gln Pro Pro Arg Glu Gln His
130                 135                 140

Pro Pro Gln Ile Arg Gly Leu Pro Ala Leu Pro Ala Pro Ser Asn
145                 150                 155                 160

Arg Asn Ser Trp Pro Gly Thr Gly Gly Asp Ala Ala Gly Glu Gln Ala
                165                 170                 175

Gly Gly Ser Arg Gly Ala Gly Asp Gly Gly Asp Gly Glu Leu Ala Asp
                180                 185                 190

Asp Asp Leu Xaa Asp Ala Ala Ala Leu Val Glu Glu
            195                 200

<210> SEQ ID NO 44
<211> LENGTH: 138
<212> TYPE: PRT
<213> ORGANISM: artificial sequence
<220> FEATURE:
<223> OTHER INFORMATION: torque teno virus

<400> SEQUENCE: 44

Ala Val Lys Pro Arg Arg Glu Ile Ser Ala Ser Arg Gly Arg Val Pro
1               5                   10                  15

Lys Val Ser Leu His Thr Glu Val Lys Gly Gln Phe Gly Leu Gly Thr
            20                  25                  30

Gly Arg Ala Met Gly Lys Ala Leu Lys Lys Ser Met Phe Ile Gly Arg
        35                  40                  45

His Tyr Arg Lys Lys Arg Ala Leu Ser Leu Cys Ala Val Arg Thr Thr
    50                  55                  60

Lys Lys Ala Cys Lys Leu Leu Ile Val Met Trp Thr Pro Pro Arg Asn
65                  70                  75                  80

Asp Gln Gln Tyr Leu Asn Trp Gln Trp Tyr Ser Ser Val Leu Ser Ser
            85                  90                  95

His Ala Ala Met Cys Gly Cys Pro Asp Ala Ile Ala His Leu Ser His
        100                 105                 110

Leu Ala Phe Val Phe Arg Ala Pro Gln Asn Pro Pro Pro Gly Pro
        115                 120                 125

Gln Arg Asn Leu Pro Leu Arg Arg Leu Pro
130                 135

<210> SEQ ID NO 45
<211> LENGTH: 138
<212> TYPE: PRT
<213> ORGANISM: artificial sequence
<220> FEATURE:
<223> OTHER INFORMATION: torque teno virus

<400> SEQUENCE: 45

Ser Gly Glu Ala Thr Glu Gly Asp Leu Arg Val Pro Arg Ala Gly Ala
1               5                   10                  15

Glu Gly Glu Phe Thr His Arg Ser Gln Gly Ala Ile Arg Ala Arg Asp
            20                  25                  30

```
Trp Pro Gly Tyr Gly Gln Gly Ser Glu Lys Ser Met Phe Ile Gly Arg
             35                  40                  45

His Tyr Arg Lys Lys Arg Ala Leu Ser Leu Cys Ala Val Arg Thr Thr
 50                  55                  60

Lys Lys Ala Cys Lys Leu Leu Ile Val Met Trp Thr Pro Pro Arg Asn
 65                  70                  75                  80

Asp Gln Gln Tyr Leu Asn Trp Gln Trp Tyr Ser Ser Val Leu Ser Ser
                 85                  90                  95

His Ala Ala Met Cys Gly Cys Pro Asp Ala Val Ala His Phe Asn His
                100                 105                 110

Leu Ala Ala Val Leu Arg Ala Pro Gln Asn Pro Pro Pro Gly Pro
            115                 120                 125

Gln Arg Asn Leu Pro Leu Arg Arg Leu Pro
    130                 135

<210> SEQ ID NO 46
<211> LENGTH: 23
<212> TYPE: PRT
<213> ORGANISM: artificial sequence
<220> FEATURE:
<223> OTHER INFORMATION: peptide of subject 24

<400> SEQUENCE: 46

Gly Ala Glu Gly Glu Phe Thr His Arg Ser Gln Gly Ala Ile Arg Ala
1               5                  10                  15

Arg Asp Trp Pro Gly Tyr Gly
            20

<210> SEQ ID NO 47
<211> LENGTH: 202
<212> TYPE: PRT
<213> ORGANISM: artificial sequence
<220> FEATURE:
<223> OTHER INFORMATION: torque teno virus

<400> SEQUENCE: 47

Met Ala Glu Phe Ser Thr Pro Val Arg Ser Gly Glu Ala Thr Glu Gly
1               5                  10                  15

Asp His Arg Val Pro Arg Ala Gly Ala Glu Gly Glu Phe Thr His Arg
            20                  25                  30

Ser Gln Gly Ala Ile Arg Ala Arg Asp Trp Pro Gly Tyr Gly Gln Gly
        35                  40                  45

Ser Glu Lys Ser Met Phe Ile Gly Arg His Tyr Arg Lys Lys Arg Ala
    50                  55                  60

Leu Ser Leu Cys Ala Val Arg Thr Thr Lys Lys Ala Cys Lys Leu Leu
65                  70                  75                  80

Ile Val Met Trp Thr Pro Pro Arg Asn Asp Gln Gln Tyr Leu Asn Trp
                85                  90                  95

Gln Trp Tyr Ser Ser Val Leu Ser Ser His Ala Ser Met Cys Gly Cys
            100                 105                 110

Pro Asp Ala Val Ala His Leu Ile Asn Leu Ala Ser Val Leu Arg Ala
        115                 120                 125

Pro Gln Asn Pro Pro Pro Gly Pro Gln Arg Asn Leu Pro Leu Arg
    130                 135                 140

Arg Leu Pro Ala Leu Pro Ala Pro Glu Ala Pro Gly Asp Arg Ala
145                 150                 155                 160

Pro Trp Pro Met Ala Gly Gly Ala Glu Gly Glu Asn Gly Gly Ala Gly
                165                 170                 175
```

```
Gly Asp Ala Asp His Gly Gly Ala Ala Gly Gly Pro Glu Asp Ala Asn
            180                 185                 190

Leu Leu Asp Ala Val Ala Ala Ala Glu Thr
        195                 200

<210> SEQ ID NO 48
<211> LENGTH: 152
<212> TYPE: PRT
<213> ORGANISM: artificial sequence
<220> FEATURE:
<223> OTHER INFORMATION: torque teno virus

<400> SEQUENCE: 48

Ala Arg Thr Pro Arg Arg Gly Val Arg Ala Ser Arg Gly Arg Val Pro
1               5                   10                  15

Glu Val Ser Leu His Thr Ala Val Lys Gly Gln Phe Gly Leu Gly Thr
            20                  25                  30

Gly Arg Ala Met Gly Lys Ala Leu Lys Lys Ala Met Phe Leu Gly Arg
        35                  40                  45

Ile Tyr Arg Lys Lys Arg Arg Leu Pro Leu Ser Pro Leu His Ser Pro
    50                  55                  60

Pro Lys Ala Arg Lys Leu Leu Arg Gly Met Trp Arg Pro Pro Thr Gln
65                  70                  75                  80

Asn Val Ser Gly Gln Glu Arg Ser Trp Tyr Asp Ser Val Phe Tyr Ser
                85                  90                  95

His Ala Ala Phe Cys Gly Cys Gly Asp Cys Val Gly His Leu Ser Tyr
            100                 105                 110

Leu Ala Thr His Leu Gly Arg Pro Pro Ser Ala Gln Pro Pro Pro Gln
        115                 120                 125

Leu Gln Pro Pro Val Ile Arg Arg Leu Pro Ala Leu Pro Ala Pro Pro
    130                 135                 140

Asn Pro Ser Gly Asp Arg Ala Ala
145                 150

<210> SEQ ID NO 49
<211> LENGTH: 49
<212> TYPE: PRT
<213> ORGANISM: artificial sequence
<220> FEATURE:
<223> OTHER INFORMATION: torque teno virus

<400> SEQUENCE: 49

Met Ala Glu Phe Ser Thr Pro Val Arg Ser Glu Gly Ala Thr Glu Gly
1               5                   10                  15

Ile Pro Asn Val Pro Arg Ala Gly Ala Gly Gly Glu Phe Thr His Arg
            20                  25                  30

Ser Gln Gly Ala Ile Arg Ala Arg Asp Trp Pro Gly Tyr Gly Gln Gly
        35                  40                  45

Ser
```

SPECIFIC TT VIRUS SEQUENCES AND CHIMERIC TT VIRUS HOST CELL DNA MOLECULES FOR USE IN DIAGNOSIS, PREVENTION AND TREATMENT OF CANCER AND AUTOIMMUNITY

FIELD OF THE INVENTION

The present invention relates to single-stranded new sequences of TT viruses and hybrid molecules of a specific TT virus sequence and host cell DNA that are capable of replicating autonomously for use in diagnosis, prevention and treatment of diseases like cancer and autoimmunity. In addition, it relates to the use of such molecules as gene vectors and artificial chromosomes.

BACKGROUND OF THE TECHNOLOGY

Since their discovery in 1997 by Okamoto and colleagues TT viruses (TTV) have been found to be widely spread in all human populations, in domestic animals, and in old world primates (1,2). A large number of types and pseudotypes have been identified in humans, pointing to a remarkable heterogeneity of this virus family now being assigned as a new virus family, Anelloviridae (3). Viral DNA can be demonstrated in sera of almost every human being and some reports even document such DNA in newborn children and cord blood, suggesting prenatal transmission of these agents (4,5). In spite of the widespread occurrence of these viruses, intensive research performed during more than 10 years failed to demonstrate a pathogenic role of such infections in human disease.

TT viruses have not been successfully replicated in human tissue culture cells, although indications exist that replication can be achieved in human cells of epithelial or hematopoietic origin. In the latter, replicative cycles of herpes group viruses (Epstein-Barr virus) seem to exert an enhancing effect for the amplification of latent or transfected TTV genomes (6). In addition, TT viruses frequently reveal intramolecular rearrangements which lead to subviral DNA genomes in part defective and with novel open reading frames. They replicate autonomously over prolonged periods of time in infected tissues (7). These subviral DNAs are found in normal and malignant human biopsy materials.

During the past years, some data have been compiled indicative of an association of TT virus infection with human malignant tumors. A high rate of TT virus load has been noted in a spleen biopsy of a patient with Hodgkin's lymphoma (24 individual TTV genotypes) (8). Similarly, other reports describe a higher rate of TTV prevalence in colorectal and esophageal cancer and in hematopoietic malignancies in comparison to non-tumorous tissue from the same or other patients (9,10). Yet, the ubiquity of these infections rendered an interpretation of these results rather difficult and did not permit a linkage of these observations with tumor development.

SUMMARY OF THE INVENTION

The technical problem underlying the present invention is to identify specific TTV sequences that might be clearly associated with diseases like cancer or autoimmune diseases and, thus, to provide means for diagnosis and therapy.

The solution to said technical problem is achieved by providing the embodiments characterized in the claims. Recent observations of the persistence of a 71 base highly conserved region (HCR), present with only minor variation in all TTV isolates characterized thus far, in a larger number of human cancer and immortalized cell lines were somewhat surprising in view of the regular long-time non-permissibility of the same cells for transfected TTV DNA. Even more surprising has been the linkage of host cell DNA sequences in an apparently single-stranded form to the TTV-HCR. The frequency and regularity of persistence of this obviously extrachromosomal genetic material in a large number of cancer cell lines as well as in biopsies of affected brain tissue from patients with multiple sclerosis prompted the following hypothesis: Host cell genes either modified in the recombinatory process or dys-regulated by novel TTV regulatory sequences play a significant role in human carcinogenesis and also in some autoimmune reactions. They may even replace or, in a certain sense, functionally correspond to retrovirus infections in rodent and chicken cells.

A Novel Role for TT Viruses in Human Cancer and Autoimmunity

The surprising observation of host cell DNA linked to an apparently single-stranded form to TT virus HCR is the basis for the following conclusion: TT viral sequences have not yet been demonstrated as integrated into double-stranded cellular DNA, persisting within host cell chromosomes. Thus, the opposite finding of host cell DNA, linked in a single-stranded state to the TTV HCR should have biological significance. The present data indicate their long-time persistence as episomes in human cancer cell lines, pointing to a role of this persistence in cell proliferation. Two aspects seem to require specific consideration: a possible role of those recombinants in cancer and in autoimmunity.

One possibility is the random integration of host cell sequences into TTV episomes. This may happen after strand displacement in the course of aberrant DNA replication or after reverse transcription of cellular RNA. In case of random integration a larger number of recombinants should be innocuous and harmless for cells carrying these recombinants. A growth-promoting property of transcripts of the TTV HCR, as well as integration and transcription of growth-stimulating host cell genes, their modification in the process of integration or their dysregulation by the TTV HCR however, will result in proliferative consequences. These episomes should acquire immortalizing and under certain conditions transforming properties. In combination with additional modifications of the host cell genome they may direct malignant growth. This mode of action reveals a distant resemblance to the insertion of cellular oncogenes into retroviral genomes.

The TTV-Oncogene Concept

Figure 4:
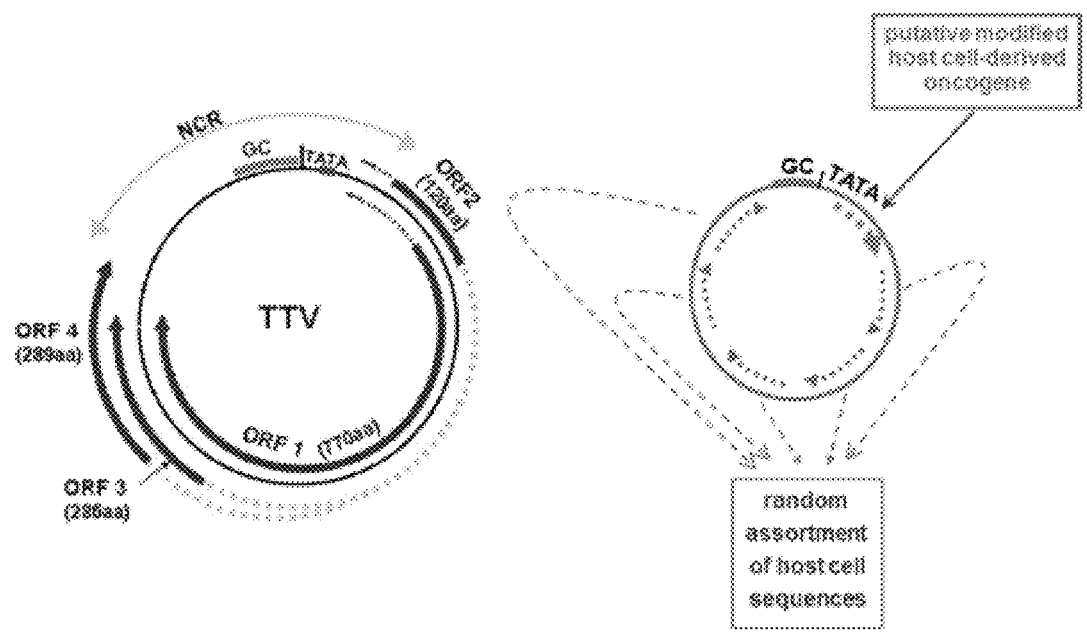

The previous considerations are summarized in FIG. 4. Obviously, the recombination between the TTV regulatory region and cellular nucleic acids must be a relatively frequent process, since such recombinants are found in the majority of cell lines thus far analyzed. It also should contribute to cell proliferation, otherwise the regular persistence of such molecules, in part over decades of continuous proliferation, would be difficult to explain. It is assumed that this type of recombination is a random process, involving different types of cellular genes. The coding function of the TTV HCR and/or the uptake of genes steering cell proliferation, or blocking the function of proliferation antagonists, or inhibiting cell differentiation should lead to an accumulation of cells containing these types of recombinants. It is envisaged that this, in combination with additional mutational or recombinational events of the cells harbouring such TTV-host cell nucleic acid recombinants, provides a selective advantage for cells carrying such episomes. The presence of the latter would represent a prime risk factor for malignant conversion. In this sense those recombinations should be of general importance for different types of human cancers, although a certain degree of specificity for a limited set of genes would be expected for individual cancer types.

The implications of this model are profound. They reach from cancer prevention, early detection into cancer therapy. The important role of TTV infections and of the persistence of TTV HCR is stressed by the available information. Prevention of these infections should reduce the risk for the development of the described recombinants. The diagnosis of specific recombinants would probably contribute to cancer risk assessment. Profound implications would be expected for cancer therapy: the TTV HCR emerges as the prime determinant for the persistence and maintenance of the single-stranded episomes. Since this region appears to be part of an open reading frame, it should be vulnerable to small interfering RNAs or DNAs. Thus, it offers a suitable target for future therapeutic deliberations.

Two other aspects deserve discussion: certain parallels which seem to exist to retroviral carcinogenesis in rodents and chicken and the use of autonomously replicating TTV-based vector systems for gene therapy. Insertional mutagenesis, the uptake and modification of cellular growth-stimulating genes, rendering them into oncogenes has frequently been analyzed in animal systems. This has thus far not been reported for human cancers. Do TT viruses replace this niche in human and other primate cells? Do TTV compete successfully with retrovirus infections in taking over their role in specific species? The episomal persistence of single-stranded DNA, however, emerges as a remarkable difference to retrovirus-induced carcinogenesis.

Autonomously replicating subviral DNA molecules of approximately 400 bases of TTV origin have been described before (11). It is tempting to speculate that they or specific TTV-host cell recombinants may represent optimal vector systems for future approaches in gene therapy and for the construction of artificial chromosomes.

The Recombinant TTV-Host Cell DNA Autoimmunity Concept

Figure 5:
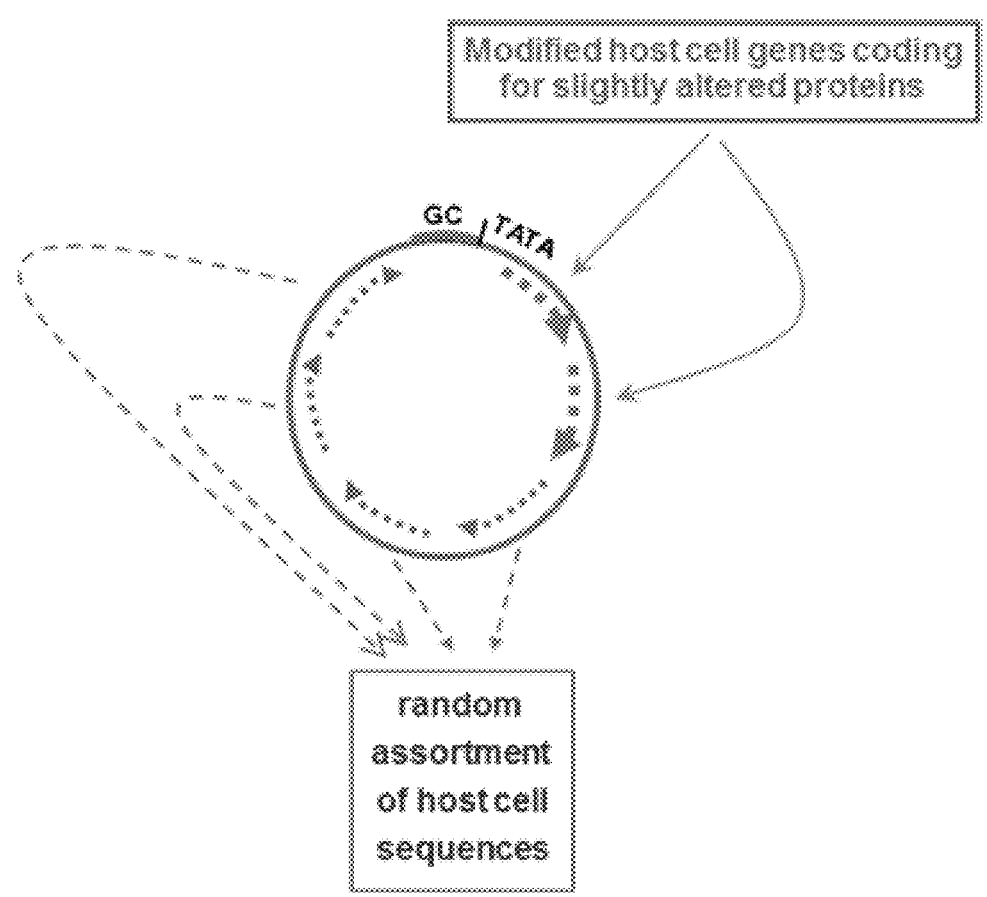

The existence of TTV host cell nucleic acid recombinants also permits a novel view on aspects of autoimmune diseases and other chronic diseases (potentially even conditions like arteriosclerosis and Alzheimer's disease). Modification or dys-regulation of cellular proteins may originate from insertional events of cellular genes into single-stranded DNA or to the different HCRs exerted by TTV elements (FIG. 5). They could provide a convenient explanation for autoimmune reactions, even for local ones, like in multiple sclerosis (MS) or Crohn's disease. In the latter two cases in particular, the reactivation of other local infections (potentially herpes-type viruses) would provide a stimulus for the local amplification and gene activity of the respective TTV-host cell nucleic acid recombinants. In MS, this could explain recurrent episodes of disease progression. A model of the autoimmunity concept is depicted in FIG. 5.

Similarly, rearranged TT virus molecules of 719, 642, and 621 bases have been identified which replicate autonomously upon transfection of specific cell lines. Their DNA composition and derivation from specific complete TTV genotypes is shown in FIG. 6. Here the rearrangement results in novel open reading frames in part with epitopes related to those of juvenile diabetes and rheumatoid arthritis.

CONCLUSION

The models of the present invention for a role of TTV-host cell nucleic acid recombinants is based on the demonstration of the single-stranded chimeric molecules between the TTV HCR and host cell DNA and rearranged autonomously replicating TTV molecules of substantially reduced molecular weights. Both, the TTV oncogene concept and the TTV autoimmunity concept will clearly provide novel approaches to prevention, diagnosis, and in particular to therapy of these conditions and will improve the prognosis of the respective patients.

Thus, in a first aspect, the present invention relates to a TT virus polynucleic acid comprising
(a) a 71 base nucleotide sequence (HCR) shown in FIG. 6;
(b) a nucleotide sequence which shows 70% identity with an HCR of (a) and is capable of replicating autonomously;
(c) a fragment of a nucleotide sequence of (a) or (b) which is capable of replicating autonomously;
(d) a nucleotide sequence which is the complement of the nucleotide sequence of (a), (b) or (c); or
(e) a nucleotide sequence which is redundant as a result of the degeneracy of the genetic code compared to any of the above-given nucleotide sequences.

In a second aspect, the present invention provides oligonucleotide primers and probes comprising part of a polynucleic acid of a TTV polynucleic acid of the invention, with (a) said primer being able to act as primer for specifically sequencing or specifically amplifying said polynucleic acid, and (b) said probe being capable of specifically hybridizing to said polynucleic acid.

The present invention also provides an expression vector comprising a TT virus polynucleic acid (HCR) of the invention operatively linked to prokaryotic, eukaryotic or viral transcription and translation control elements as well as a host cell transformed with an expression vector according to claim 11.

Moreover, the present invention provides a polypeptide being encoded by a TT virus polynucleic acid (HCR) of the invention and an antibody specifically binding to such polypeptide.

A diagnostic kit is also provided. Such kit is for use in determining the presence of a TT virus polynucleic acid of the invention and comprises a primer, a probe, a polypeptide or an antibody of the invention. Said primer, probe, polypeptide or antibody are useful for the diagnosis of a predisposition or an early stage of cancer or an autoimmune disease.

The present invention also provides an antisense oligonucleotide abolishing the persistence of this DNA or reducing or inhibiting the expression of the TTV polynucleic acid of the invention, preferably an iRNA comprising a sense sequence and an antisense sequence, wherein the sense and antisense sequences form an RNA duplex and wherein the antisense sequence comprises a nucleotide sequence sufficiently complementary to the nucleotide sequence of the TT virus polynucleic acid of the invention.

The present invention also relates to the construction of transgenic mice, carrying the TTV sequences of the invention, for diagnostic and experimental therapeutic purposes.

In a further aspect, the present invention relates to a pharmaceutical composition comprising the antibody, antisense oligonucleotide or oligopeptide (aptamer) of the invention and a suitable pharmaceutical carrier.

Said antibody, antisense oligonucleotide or oligopeptide are useful for the prevention or treatment of cancer (preferably breast cancer, ovarian cancer, lung cancer, liver cancer, colon or rectal cancer, pancreatic cancer, prostate cancer, skin cancer, stomach cancer, a cancer of the urinary system (e.g., kidney cancer), Hodgkin's lymphoma, B-lymphoma, acute lymphocytic leukemia, Burkitt's lymphoma or brain tumors) or an autoimmune disease (preferably multiple sclerosis (MS), asthma, Crohn's disease, polyarthritis, juvenile diabetes) or early stages thereof. Said compounds are also useful in the treatment/prevention of arteriosclerosis and Alzheimer's disease (AD).

Finally, the present invention provides a vaccine comprising a polypeptide of the invention for use in a method of immunizing a mammal against a TT virus infection.

DETAILED DESCRIPTION OF THE INVENTION

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

By "antibody" is meant a protein of the immunoglobulin family that is capable of combining, interacting or otherwise associating with an antigen. The term "antigen" is used herein in its broadest sense to refer to a substance that is capable of reacting in and/or inducing an immune response. Typically, but not necessarily, antigens are foreign to the host animal in which they produce immune reactions.

By "epitope" is meant that part of an antigenic molecule against which a particular immune response is directed. Typically, in an animal, antigens present several or even many antigenic determinants simultaneously. Thus, the terms "epitope" and "antigenic determinant" mean an amino acid sequence that is immunoreactive. Generally an epitope consists of 4, and more usually 5, 6, 7, 8 or 9 contiguous amino acids. However, it should also be clear that an epitope need not be composed of a contiguous amino acid sequence. The immunoreactive sequence may be separated by a linker, which is not a functional part of the epitope. The linker does not need to be an amino acid sequence, but can be any molecule that allows the formation of the desired epitope.

The term "biological sample" as used herein refers to a sample that may be extracted, untreated, treated, diluted or concentrated from an animal. Biological sample refers to any biological sample (tissue or fluid) containing a TTV polynucleic acid of the invention and refers more particularly to blood serum samples, plasma samples, biopsy samples, cerebrospinal fluid samples etc.

By "carrier" is meant any substance of typically high molecular weight to which a non- or poorly immunogenic substance (e.g., a hapten) is naturally or artificially linked to enhance its immunogenicity.

The term "diagnosis" is used herein in its broadest sense to include detection of an antigen reactive to a sub-immunoglobulin antigen-binding molecule. Also included within its scope, is the analysis of disorder mechanisms. Accordingly, the term "diagnosis" includes the use of monoclonal antibodies for research purposes as tools to detect and understand mechanisms associated with a disease or condition of interest. It also includes the diagnostic use of TTV polynucleic acid of the invention for the detection of homologous or complementary RNA transcribed from such molecules.

The term "immunogenicity" is used herein in its broadest sense to include the property of evoking an immune response within an organism. Immunogenicity typically depends partly upon the size of the substance in question, and partly upon how unlike host molecules it is. It is generally considered that highly conserved proteins tend to have rather low immunogenicity.

The term "patient" refers to patients of human or other mammal origin and includes any individual it is desired to examine or treat using the methods of the invention. However, it will be understood that 'patient' does not imply that symptoms are present. Suitable mammals that fall within the scope of the invention include, but are not restricted to, primates, livestock animals (e.g., sheep, cows, horses, donkeys, pigs), laboratory test animals (e.g., rabbits, mice, rats, guinea pigs, hamsters), companion animals (e.g., cats, dogs) and captive wild animals (e.g., foxes, deer, dingoes).

By 'pharmaceutically acceptable carrier" is meant a solid or liquid filler, diluent or encapsulating substance that may be safely used in any kind of administration.

The term "related disease or condition" is used herein to refer to a disease or condition that is related anatomically, physiologically, pathologically and/or symptomatically to a reference disease or condition. For example, diseases or conditions may be related to one another by affecting similar anatomical locations (e.g., affecting the same organ or body part), affecting different organs or body parts with similar physiological function (e.g., the oesophagus, duodenum and colon which rely an peristalsis to move food from one end of the alimentary canal to the other), by having similar or overlapping pathologies (e.g., tissue damage or rupture, apoptosis, necrosis) or by having similar or overlapping symptoms (i.e., allergic response, inflammation, lymphocytosis). Thus, for example, an antigen associated with ulcerated colitis may also be associated with perforation of the colon because these disease affects the same organ (i.e., colon).

The term "treating" is used herein in its broadest sense to include both therapeutic and prophylactic (i.e., preventative) treatment designed to ameliorate the disease or condition.

The term "episome" is used herein to refer to a portion of genetic material that can exist independent of the main body of genetic material (chromosome) at some times or continuously and replicate autonomously, while at other times is able to integrate into the chromosome. Examples of episomes include insertion sequences, transposons and the TTV of the invention.

FIGURE LEGENDS

FIG. 1: PCR amplification of a 71 base fragment containing the highly conserved TTV region (HCR) in 4 different cell lines, L1236 (EBV-negative Hodgkin's lymphoma line), HSB-2 (acute lymphoblastic leukemia line), KR and IGL (melanoma cell lines) and placenta DNA FIG. 2: Spooled DNA remaining in the supernatant of L1236 cells after precipitation and removal of high molecular weight DNA and RNase digestion Two bands are visible in the region between 4.3 and 6.6 base bands.

Figure 3:
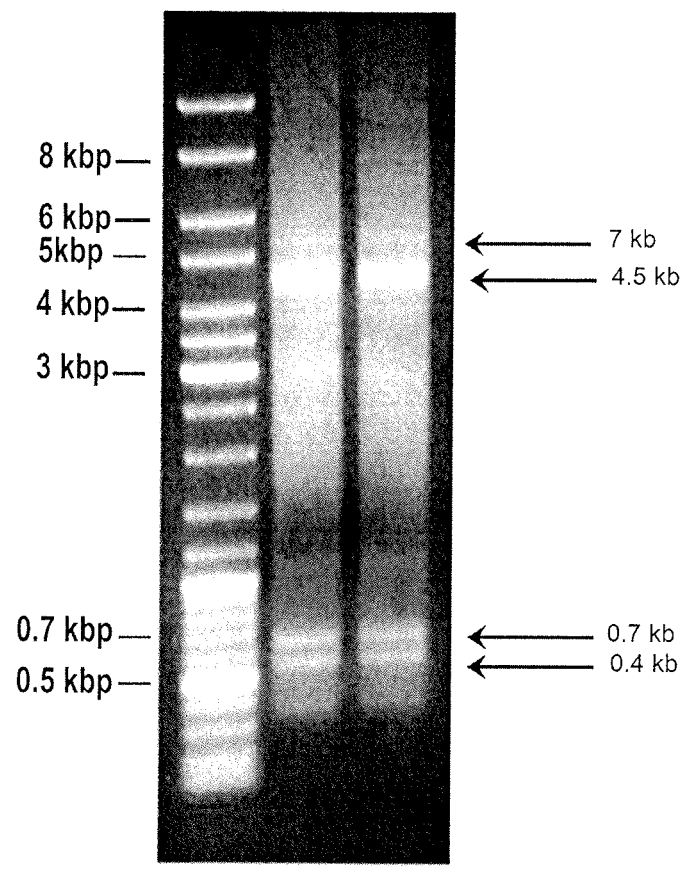

FIG. 3: Outwards-directed long-PCR, using primers of the 71 base TTV HCR region in HSB-2 DNA Two bands are visible in regions corresponding to 4.5 to 7 kb. In addition, bands emerge in the region corresponding to 0.4 to 0.7 kb.

FIG. 4: Schematic outline of the TTV oncogene concept

The left part represents the genomic organization of wild-type TTV genomes. The right part envisages the integration of host cell DNA into the single-stranded plasmids.

FIG. 5: Schematic outline of the TTV host cell DNA autoimmunity concept

The modified host cell genes should code for immunoreactive antigenic epitopes.

FIG. 6: PCR amplification of the 71 base HCR from the DNA of 4 different cell lines Zyb2 (SEQ ID NO:1), zyb9 (SEQ ID NO:2), zkb5 (SEQ ID NO:3) and zkb69 (SEQ ID NO:4). The arrows point to the two sites with variations in the nucleotide sequences.

Figure 7A:
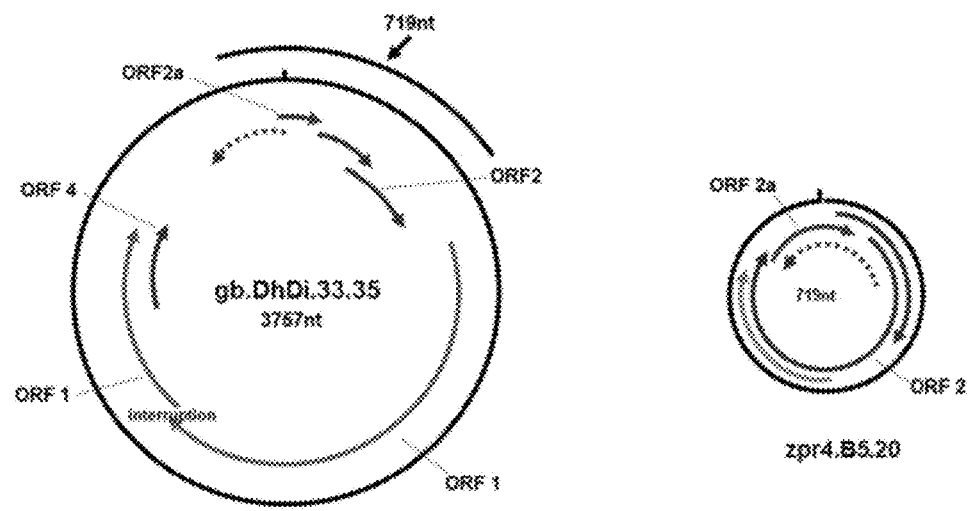

FIG. 7:

FIG. 7A, The autonomously replicating 719 base TTV DNA (right) and the complete TTV sequence from which it is derived. The nucleotide composition of both molecules is found in FIG. 11A+B.

Figure 7B:
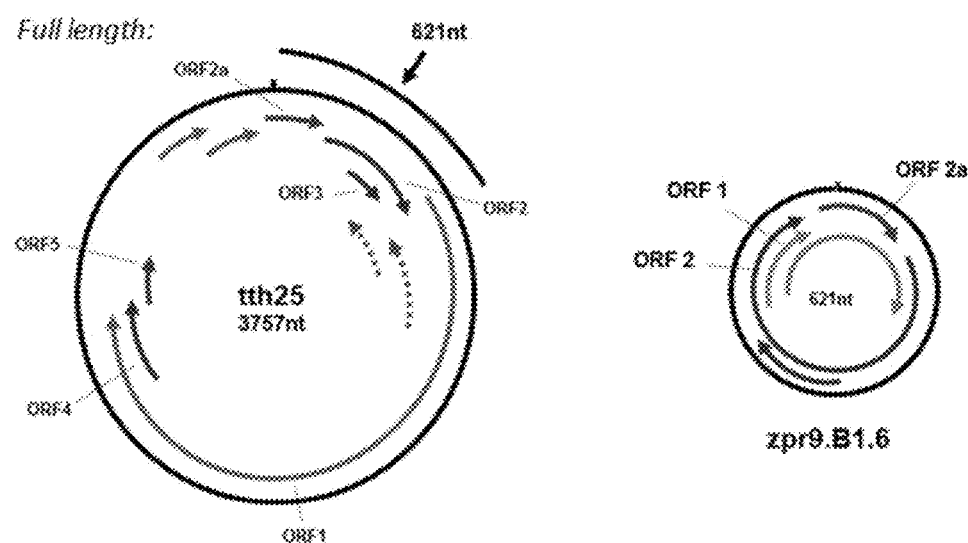

FIG. 7B, The autonomously replicating 621 base TTV DNA (right) and the complete DNA sequence from which it is derived. The nucleotide composition of both molecules is found in FIG. 12A+B.

Figure 7C:
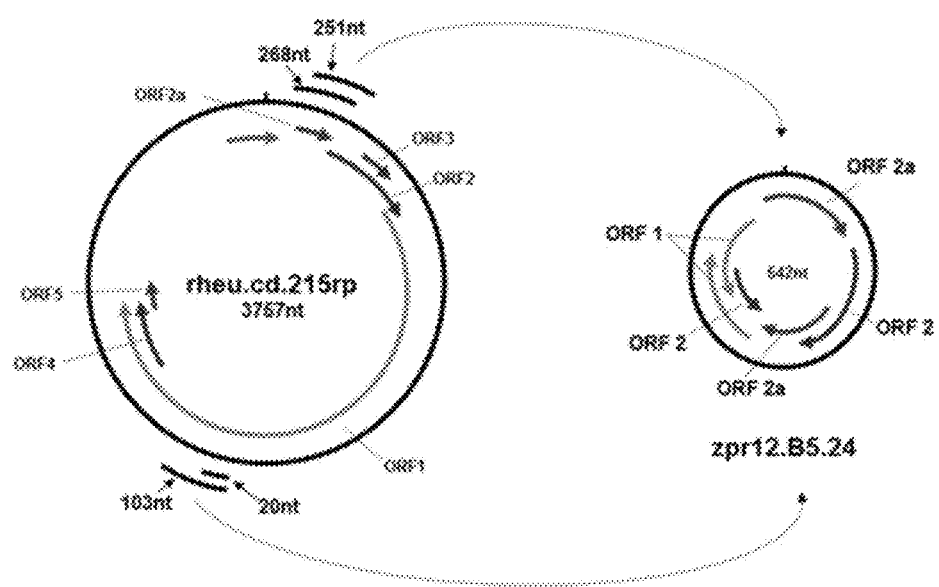

FIG. 7C, The autonomously replicating 642 base TTV DNA (right) and the complete DNA sequence from which it is derived. The nucleotide composition of both molecules is found in FIG. 13A+B.

FIG. 8: Three exemplary chimeric TTV/truncated host cell DNA sequences from brain biopsies of patients with multiple sclerosis FIG. 8A, Chimeric cellular sequences WV13038Klon6 (SEQ ID NO:5) derived from chromosome 1 with some homologies to prion and Wilms tumor sequences and the 3' end of myeloid lymphoid leukemia 3 (MLL3) pseudogene. Human DNA sequence from clone RP11-14N7 on chromosome 1. Contains 3' end of a myeloid/lymphoid or mixed lineage leukemia 3 (MLL3) pseudogene, a seven transmembrane helix receptor pseudogene, the 5'-end of a novel gene.

FIG. 8B, Chimeric cellular sequences gb40.27 (SEQ ID NO:6) derived from chromosome 16. Homologies to transcription factor 3 (TF 3C), protein signatures for chemokine receptors and leukotriene B4 receptor.

FIG. 8C, Chimeric cellular sequences derived from chromosome 10, truncated sequence of myosin, reactivity reported for multiple sclerosis patients and those with rheumatoid arthritis (sequence contains both full primers front and back). Sequence of gb43.30 (SEQ ID NO:7); J) BLAST of gbHhDi43.30 (SEQ ID NO:9) and *homo sapiens* myosin IIIA (SEQ ID NO:8), J+K) BLAST of gb43.30 (SEQ ID NO:9) and human DNA sequence on chromosome 10 (SEQ ID NO:10); L) peptide FASTA of gbDhDi43.30 (SEQ ID NO:11) and ORF2 of Torque teno virus fragment Q9WB12_9VIRU (SEQ ID NO:12); protein sequence of torque teno virus ORF2 (SEQ ID NO:12).

FIG. 9: Three exemplary chimeric TTV/truncated host cell DNA sequences from cell lines derived from patients with Hodgkin's disease or leukemia FIG. 9A, Chromosome 1 sequences with part of transgelin 2, the IGSF9 gene for immunoglobulin superfamily member 9, the SLAM9 gene. Sequence of hodll (SEQ ID NO:13); strand=plus/plus: BLAST of hodL.VvWw.1.seq (SEQ ID NO:14) and human DNA sequence on chromosome 1 (SEQ ID NO:15); strand=plus/minus: BLAST of hodL.VvWw.1.seq (SEQ ID NO:16) and human DNA sequence on chromosome 1 (SEQ ID NO:17).

FIG. 9B, Translated protein sequences with substantial homology to the oncogenes v-myb (avian myeloblastosis viral oncogene), but also to c-myb. This sequence was amplified with the forward primer at both ends. Sequence of hoht33 (SEQ ID NO:18).

FIG. 9C, Derived from chromosome 10. High homology with "Deleted in malignant 1 Protein" (DMBT), an identified tumor suppressor gene. This sequence was amplified with the forward primer at both ends. Sequence of hoht22 (SEQ ID NO:19).

FIG. 10:

Primer sequences used in the reactions described in the Examples, derived from the 71 base HCR. DhDi forward (SEQ ID NO:20), DhDi reverse (SEQ ID NO:21), cd forward (SEQ ID NO:22), cd reverse (SEQ ID NO:23), DfDg (SEQ ID NO:24), DfDg reverse (SEQ ID NO:25).

FIG. 11:

FIG. 11A, Complete TTV sequence from which autonomously replicating 719 base DNA has been obtained. Sequence of ttgb33.35 (SEQ ID NO:26).

FIG. 11B, Complete sequence of the autonomously replicating 719 base TTV DNA. Sequence of zpr4.20 (SEQ ID NO:27).

FIG. 12:

FIG. 12A, Complete TTV sequence (tth25) from which autonomously replicating 621 base DNA has been obtained (SEQ ID NO:28).

FIG. 12B, Complete sequence of the autonomously replicating 621 base TTV DNA (SEQ ID NO:29).

FIG. 13:

FIG. 13A, Complete TTV sequence (ttrh215) from which autonomously replicating 642 base DNA has been obtained (SEQ ID NO:30).

FIG. 13B, Complete sequence of the autonomously replicating 642 base TTV DNA (SEQ ID NO:31).

FIG. 14: Open reading frames (ORFs) found within the nucleotide sequence of 71 nt FIG. 14A, zyb2.1.pep (SEQ ID NO:32), zyb9.1.pep (SEQ ID NO:33), and zkb69.1.pep (SEQ ID NO:34) are starting at the first triplet, zyb2.3.pep (SEQ ID NO:35), zyb9.3.pep (SEQ ID NO:36), zkb5.3.pep (SEQ ID NO:37), and zkb69.3.pep (SEQ ID NO:38) are starting from the third triplet. This region is actively transcribed.

FIG. 14B, zyb2.1.pep and Sbjct 27 (SEQ ID NO:32), Sbjct14 (SEQ ID NO:39), Q9WSW0 (SEQ ID NO:40), Q9WB09_VIRU (SEQ ID NO:41).

FIG. 14C, zyb2.3.pep (SEQ ID NO:35), Sbjct24 (SEQ ID NO:36), Q98Y39_9VIRU (SEQ ID NO:42).

FIG. 14D, zyb9.1.pep and Sbjct27 (SEQ ID NO:33), Q9WSW09_VIRU (SEQ ID NO:43) Q9WB09_9VIRU (SEQ ID NO:44).

FIG. 14E, zyb9.3.pep and Sbjct15 (SEQ ID NO:36), Q9WAY7_9VIRU (SEQ ID NO:45).

FIG. 14F, zkb5.3.pep (SEQ ID NO:37), Subject 24 (SEQ ID NO:46), Q98Y39_9VIRU (SEQ ID NO:47).

FIG. 14G, zkb69.1.pep and Sbjct14 (SEQ ID NO:34), Q9WAZ2_9VIRU (SEQ ID NO:48).

FIG. 14H, zkb69.3.pep and Sbjct24 (SEQ ID NO:38) and Q9JGT3_9VIRU (SEQ ID NO:49).

Figure 15:
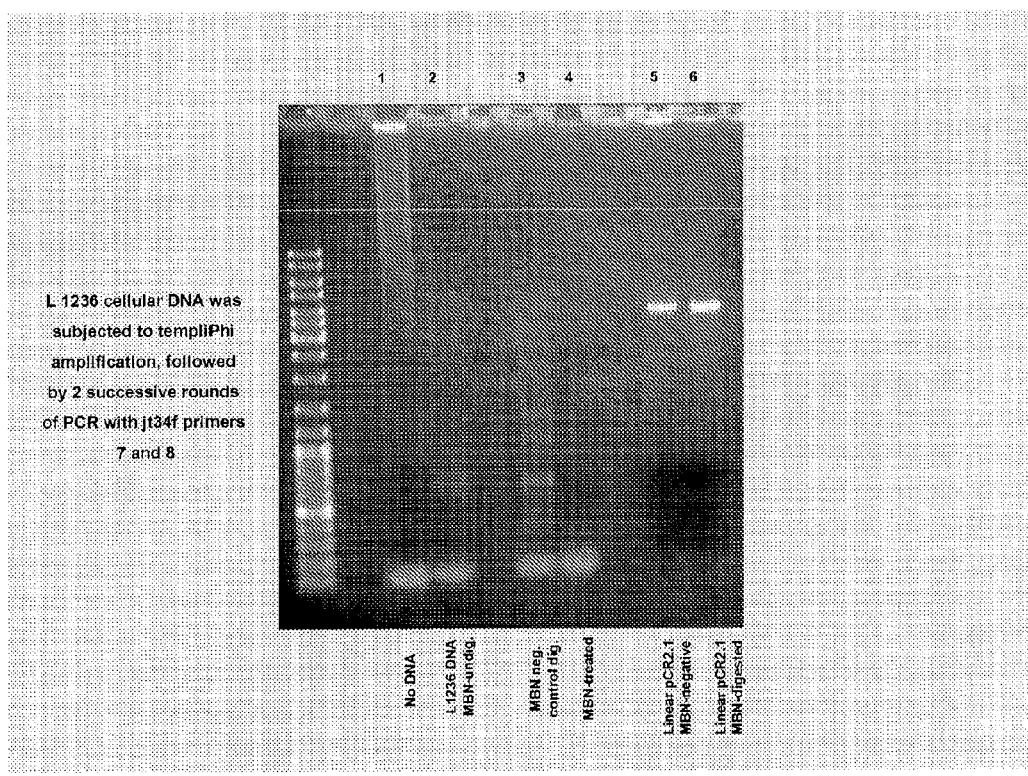

FIG. 15: Digestion of single-stranded DNA by mung-bean nuclease (MBN)

Lanes 2 and 3 show that the amplified DNA can be digested by pre-treatment with MBN. Lanes 5 and 6 demonstrate that plasmid-DNA pretreated in the same way is not digested by MBN.

The present invention provides an isolated TT virus polynucleic acid comprising a nucleotide sequence shown in FIG. 6.

The present invention also provides an isolated nucleotide sequence which shows 70%, preferably 80%, more preferably 90% and most preferably 95% identity to the corresponding regions of a nucleotide sequence of FIGS. 6 to 13 and is capable of replicating autonomously.

The present invention also provides fragments of the nucleotide sequences of the present invention described above that are capable of replicating autonomously. The skilled person can derive at fragments still having the biological activity of the full length molecule without undue experimantation. The lengths of the fragments are not critical, however, fragments having a length of at least 45, at least 55, or at least 65 nt are preferred.

The person skilled in the art can easily determine which nucleic acid sequences are related to the nucleotide sequence of FIG. 6 or which fragments are still capable of replicating autonomously by using standard assays or the assays described in the examples, below.

The present invention more specifically relates to an isolated TT virus polynucleic acid having (a) a nucleotide sequence shown in FIG. 6, (b) a nucleotide sequence which shows 70% (80%, 90%, or 95%) identity to the nucleotide sequence of (a) and is capable of replicating autonomously, (c) a fragment of the nucleotide of (a) or (b) which is capable of replicating autonomously, or (d) the complement of (a), (b), or (c).

The present invention also provides polynucleic acid sequences which are redundant as a result of the degeneracy of the genetic code compared to any of the above-given nucleotide sequences. These variant polynucleic acid sequences will thus encode the same amino acid sequence as the polynucleic acids they are derived from.

The term "polynucleic acid" refers to a single-stranded or double-stranded nucleic acid sequence. A polynucleic acid may consist of deoxyribonucleotides or ribonucleotides, nucleotide analogues or modified nucleotides, or may have been adapted for therapeutic purposes. Preferably, the TT virus polynucleic acid is a single-stranded DNA.

The TT virus polynucleic acid of the invention might be present as an extrachromosomal episome, might be integrated into the host's genome and/or might be linked to a host cell DNA, e.g., a DNA comprising a growth-stimulating host cell gene, oncogene or containing truncated host cell genes with altered immunogenicity.

Preferably, the TT virus polynucleic acid of the invention comprises a nucleotide sequence being selected from the group of nucleotide sequences shown in FIGS. 8, 9 and 11 to 13.

The present invention also relates to an oligonucleotide primer comprising or consisting of part of a polynucleic acid as defined above, with said primer being able to act as primer for specifically sequencing or specifically amplifying TT virus HCR polynucleic acid of the invention and attached cellular DNA sequences.

The term "primer" refers to a single stranded DNA oligonucleotide sequence capable of acting as a point of initiation for synthesis of a primer extension product which is complementary to the nucleic acid strand to be copied. The length and the sequence of the primer must be such that they allow priming the synthesis of the extension products. Preferably the primer is about 5-50 nucleotides. Specific length and sequence will depend on the complexity of the required DNA or RNA targets, as well as on the conditions of primer use such as temperature and ionic strength.

The fact that amplification primers do not have to match exactly with corresponding template sequence to warrant proper amplification is amply documented in the literature (17). The amplification method used can be either polymerase chain reaction (PCR; (18)), ligase chain reaction (LCR; (19, 20)), nucleic acid sequence-based amplification (NASBA; (21, 22)), transcription-based amplification system (TAS; (23)), strand displacement amplification (SDA; (24)) or amplification by means of Q13, replicase (25, 26) or any other suitable method to amplify nucleic acid molecules using primer extension. During amplification, the amplified products can be conveniently labelled either using labelled primers or by incorporating labelled nucleotides.

Labels may be isotopic (32P, 35S, etc.) or non-isotopic (biotin, digoxigenin, etc.). The amplification reaction is repeated between 20 and 70 times, advantageously between 25 and 45 times.

Any of a variety of sequencing reactions known in the art can be used to directly sequence the viral genetic information and determine the orf by translating the sequence of the sample into the corresponding amino acid sequence. Exemplary sequencing reactions include those based on techniques developed by Sanger or Maxam and Gilbert. It is also contemplated that a variety of automated sequencing procedures may be utilized when performing the subject assays including sequencing by mass spectrometry (see, for example: PCT publication WO 94/16101). It will be evident to one skilled in the art that, for example the occurrence of only two or three nucleic bases needs to be determined in the sequencing reaction.

Preferably, these primers are about 5 to 50 nucleotides long, more preferably from about 10 to 25 nucleotides. Most preferred are primers having a length of at least 13 bases.

In a preferred embodiment, a primer of the present invention has a nucleotide sequence as indicated in FIG. 10.

The present invention also relates to an oligonucleotide probe comprising or consisting of part of a TT virus polynucleic acid as defined above, with said probe being able to act as a hybridization probe for specific detection of a TTV nucleic acid according to the invention.

The probe can be labelled or attached to a solid support.

The term "probe" refers to single stranded sequence-specific oligonucleotides which have a sequence which is complementary to the target sequence of the TTV polynucleic acid to be detected.

Preferably, these probes are about 5 to 50 nucleotides long, more preferably from about 10 to 25 nucleotides. Most preferred are probes having a length of at least 13 bases.

The term "solid support" can refer to any substrate to which an oligonucleotide probe can be coupled, provided that it retains its hybridization characteristics and provided that the background level of hybridization remains low. Usually the solid substrate will be a microtiter plate, a membrane (e.g. nylon or nitrocellulose) or a microsphere (bead). Prior to application to the membrane or fixation it may be convenient to modify the nucleic acid probe in order to facilitate fixation or improve the hybridization efficiency. Such modifications may encompass homopolymer tailing, coupling with different reactive groups such as aliphatic groups, NH$_2$ groups, SH groups, carboxylic groups, or coupling with biotin or haptens.

The oligonucleotides according to the present invention, used as primers or probes may also contain or consist of nucleotide analoges such as phosphorothioates (12), alkyl-phosphoriates (13) or peptide nucleic acids (14, 15) or may contain intercalating agents (16). These modifications will necessitate adaptions with respect to the conditions under which the oligonucleotide should be used to obtain the required specificity and sensitivity. However, the eventual results will be essentially the same as those obtained with the unmodified oligonucleotides.

The introduction of these modifications may be advantageous in order to positively influence characteristics such as hybridization kinetics, reversibility of the hybrid-formation, biological stability of the oligonucleotide molecules, etc.

The polynucleic acids of the invention may be comprised in a composition of any kind. Said composition may be for diagnostic, therapeutic or prophylactic use.

Also included within the present invention are sequence variants of the polynucleic acids as selected from any of the nucleotide sequences with said sequence variants containing either deletions and/or insertions of one or more nucleotides, especially insertions or deletions of 1 or more codons, mainly at the extremities of oligonucleotides (either 3' or 5'), or substitutions of some non-essential nucleotides by others (including modified nucleotides an/or inosine).

Particularly preferred variant TTV polynucleic acids of the present invention include also sequences which hybridise under stringent conditions with any of the polynucleic acid sequences of the present invention. Particularly, sequences which show a high degree of homology (similarity) to any of the polynucleic acids of the invention as described above. Particularly preferred sequences are at least 70%, 80%, 85%, 90%, 95% or more homologous to said polynucleic acid sequences of the invention. Preferably said sequences will have less than 20%, 15%, 10%, or 5% variation of the original nucleotides of said polynucleic acid sequence.

TTV polynucleic acid sequences according to the present invention which are similar to the sequences as shown in FIG. 6 can be characterized and isolated according to any of the techniques known in the art, such as amplification by means of sequence-specific primers, hybridization with sequence-specific probes under more or less stringent conditions, sequence determination of the genetic information of TTV, etc.

The present invention also relates to a recombinant expression vector comprising a TTV polynucleic acid of the invention as defined above operably linked to prokaryotic, eukaryotic or viral transcription and translation control elements.

The term "vector" may comprise a plasmid, a cosmid, an artificial chromosome, a phage, or a virus or a transgenic non-human animal. Particularly useful for vaccine development may be TT virus recombinant molecules, BCG or adenoviral vectors, as well as avipox recombinant viruses.

The term "recombinantly expressed" used within the context of the present invention refers to the fact that the polypeptides of the present invention are produced by recombinant expression methods be it in prokaryotes, or lower or higher eukaryotes as discussed in detail below.

The term "lower eukaryote" refers to host cells such as yeast, fungi and the like. Lower eukaryotes are generally (but not necessarily) unicellular. Preferred lower eukaryotes are yeasts, particularly species within *Saccharomyces, Schizosaccharomyces, Kluiveromyces, Pichia* (e. g. *Pichia pastoris*), *Hansenula* (e. g. *Hansenula* polymorph), *Schwaniomyces, Schizosaccharomyces, Yarowia, Zygosaccharomyces* and the like. *Saccharomyces cerevisiae, S. carlsbergensis* and *K. lactis* are the most commonly used yeast hosts, and are convenient fungal hosts.

The term "higher eukaryote" refers to host cells derived from higher animals, such as mammals, reptiles, insects, and the like. Presently preferred higher eukaryote host cells are derived from Chinese hamster (e. g. CHO), monkey (e. g. COS and Vero cells), baby hamster kidney (BHK), pig kidney (PK15), rabbit kidney 13 cells (RK13), the human osteosarcoma cell line 143 B, the human cell line HeLa and human hepatoma cell lines like Hep G2, and insect cell lines (e.g. *Spodoptera frugiperda*). The host cells may be provided in suspension or flask cultures, tissue cultures, organ cultures and the like. Alternatively the host cells may also be transgenic non-human animals.

The term "prokaryotes" refers to hosts such as *E. coli, Lactobacillus, Lactococcus, Salmonella, Streptococcus, Bacillus subtilis* or *Streptomyces*. Also these hosts are contemplated within the present invention.

The term "host cell" refers to cells which can be or have been, used as recipients for a recombinant vector or other transfer polynucleotide, and include the progeny of the original cell which has been transfected.

It is understood that the progeny of a single parental cell may not necessarily be completely identical in morphology or in genomic or total DNA complement as the original parent, due to natural, accidental, or deliberate mutation or recombination.

The term "replicon" is any genetic element, e. g., a plasmid, a chromosome, a virus, a cosmid, etc., that behaves as an autonomous unit of polynucleotide replication within a cell, i. e., capable of replication under its own control.

The term "vector" is a replicon further comprising sequences providing replication and/or expression of a desired open reading frame.

The term "control element" refers to polynucleotide sequences which are necessary to effect the expression of coding sequences to which they are ligated. The nature of such control sequences differs depending upon the host organism; in prokaryotes, such control sequences generally include promoter, ribosomal binding site, splicing sites and terminators; in eukaryotes, generally, such control sequences include promoters, splicing sites, terminators and, in some instances, enhancers. The term "control elements" is intended to include, at a minimum, all components whose presence is necessary for expression, and may also include additional components whose presence is advantageous, for example, leader sequences which govern secretion.

The term "promoter" is a nucleotide sequence which is comprised of consensus sequences which allow the binding of RNA polymerase to the DNA template in a manner such that mRNA production initiates at the normal transcription initiation site for the adjacent structural gene.

The expression "operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

The segment of the TTV DNA encoding the desired sequence inserted into the vector sequence may be attached to a signal sequence. Said signal sequence may be that from a non-TTV source, but particularly preferred constructs according to the present invention contain signal sequences appearing in the TTV genome before the respective start points of the proteins.

Higher eukaryotes may be transformed with vectors, or may be infected with a recombinant virus, for example a recombinant vaccinia virus. Techniques and vectors for the insertion of foreign DNA into vaccinia virus are well known in the art, and utilize, for example homologous recombination. A wide variety of viral promoter sequences, possibly terminator sequences and poly(A)-addition sequences, possibly enhancer sequences and possibly amplification sequences, all required for the mammalian expression, are available in the art. Vaccinia is particularly preferred since vaccinia halts the expression of host cell proteins. For vaccination of humans the avipox and Ankara Modified Virus (AMV) are particularly useful vectors.

Also known are insect expression transfer vectors derived from baculovirus *Autographa californica* nuclear polyhedrosis virus (AcNPV), which is a helper-independent viral expression vector. Expression vectors derived from this system usually use the strong viral polyhedrin gene promoter to drive the expression of heterologous genes. Different vectors as well as methods for the introduction of heterologous DNA into the desired site of baculovirus are available to the man skilled in the art for baculovirus expression. Also different signals for posttranslational modification recognized by insect cells are known in the art.

The present invention also relates to a host cell as defined above transformed with a recombinant vector as defined above.

The present invention also relates to a polypeptide having an amino acid sequence encoded by a TTV polynucleic acid as defined above, or a part or an analogue thereof being substantially similar and biologically equivalent.

The term "polypeptide" refers to a polymer of amino acids and does not refer to a specific length of the product. Thus, peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogues of an amino acid (including, for example, unnatural amino acids, peptide nucleic acid (PNA), etc.), polypeptides with substituted linkages, as well as other modifications known in the art, both naturally occurring and non-naturally occurring.

By "biologically equivalent" as used throughout the specification and claims, it is meant that the compositions are immunogenically equivalent to the polypeptides of the invention as defined above and below.

By "substantially homologous" as used throughout the specification and claims to describe polypeptides, it is meant a degree of homology in the amino acid sequence to the polypeptides of the invention. Preferably the degree of homology is in excess of 70%, preferably in excess of 80%, with a particularly preferred group of proteins being in excess of 90% or even 95% homologous with the polypeptides of the invention.

The term "analogue" as used throughout the specification to describe the polypeptides of the present invention, includes any polypeptide having an amino acid residue sequence substantially identical to a sequence specifically shown herein in which one or more residues have been conservatively substituted with a biologically equivalent residue. Examples of conservative substitutions include the substitution of one nonpolar (hydrophobic) residue such as isoleucine, valine, leucine or methionine for another, the substitution of one polar (hydrophillic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that the resulting protein or peptide is biologically equivalent to the protein or peptide of the invention.

"Chemical derivative" refers to a protein or peptide having one or more residues chemically derivatized by reaction of a functional side group. Examples of such derivatized molecules, include but are not limited to, those molecules in which free amino groups have been derivatized to form amine hydrochlorides, p-toluene sulfonyl groups, carbobenzoxy groups, tbutyloxycarbonyl groups, chloracetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imbenzylhistidine. Those proteins or peptides are also included as chemical derivatives which contain one or more naturally-occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. The polypeptides of the present invention also include any polypeptide having one or more additions and/or deletions or residues relative to the sequence of a polypeptide whose sequence is shown herein, so long as the polypeptide is biologically equivalent to the polypeptides of the invention.

The polypeptides according to the present invention contain preferably at least 3, preferably 4 or 5 contiguous TTV amino acids, 6 or 7 preferably however at least 8 contiguous TTV amino acids, at least 10 or at least 15.

The polypeptides of the invention, and particularly the fragments, can be prepared by classical chemical synthesis. The synthesis can be carried out in homogeneous solution or in solid phase. For instance, the synthesis technique in homogeneous solution which can be used is the one described by Houbenweyl in the book entitled "Methode der organischen Chemie" (Method of organic chemistry) edited by E. Wunsh, vol. 15-I et II. THIEME. Stuttgart 1974.

The polypeptides of the invention can also be prepared in solid phase according to for example the methods described by Atherton and Shepard in their book entitled "Solid phase peptide synthesis" (IRL Press, Oxford, 1989).

The polypeptides according to this invention can also be prepared by means of recombinant DNA techniques as for example described by Maniatis et al., Molecular Cloning: A Laboratory Manual, New York, Cold Spring Harbor Laboratory, 1982.

The present invention also relates to a method for production of a recombinant polypeptide as defined above, comprising: (a) transformation of an appropriate cellular host with a recombinant vector, in which a polynucleic acid or a part thereof as defined above has been inserted under the control of the appropriate regulatory elements, (b) culturing said transformed cellular host under conditions enabling the expression of said insert, and (c) harvesting said polypeptide.

The present invention also relates to an antibody raised upon immunization with at least one polypeptide as defined above, with said antibody being specifically reactive with any of said polypeptides, and with said antibody being preferably a monoclonal antibody. The term "antibody", preferably, relates to antibodies which consist essentially of pooled monoclonal antibodies with different epitopic specifities, as well as distinct monoclonal antibody preparations. Monoclonal antibodies are made from an antigen containing, e.g., a polypeptide encoded by the TTV polynucleic acid of the invention or a fragment thereof by methods well known to those skilled in the art (see, e.g. (27)). As used herein, the term "antibody" (Ab) or "monoclonal antibody" (Mab) is meant to include intact molecules as well as antibody fragments (such as, for example, Fab and F(ab')2 fragments) which are capable of specifically binding to protein. Fab and F(ab')2 fragments lack the Fc fragment of intact antibody, clear more rapidly from the circulation, and may have less non-specific tissue binding than an intact antibody (28). Thus, these fragments are preferred, as well as the products of a FAB or other immunoglobulin expression library. Moreover, antibodies useful for the purposes of the present invention include chimerical, single chain, and humanized antibodies.

Preferably, the antibody or antigen binding fragment thereof carries a detectable label. The antibody/fragment can be directly or indirectly detectably labeled, for example, with a radioisotope, a fluorescent compound, a bioluminescent compound, a chemiluminescent compound, a metal chelator or an enzyme. Those of ordinary skill in the art will know of other suitable labels for binding to the antibody, or will be able to ascertain such, using routine experimentation.

The present invention also relates to a diagnostic kit for use in determining the presence of a TT virus polynucleic acid or polypeptide of the invention, said kit comprising a primer, a probe, and/or an antibody of the invention.

The present invention also relates to a method for the detection of a TTV polynucleic acid according to the invention present in a biological sample, comprising: (a) optionally extracting sample polynucleic acid, (b) amplifying the polynucleic acid as described above with at least one primer as defined above, optionally a labelled primer, and (c) detecting the amplified polynucleic acids.

The term "polynucleic acid" can also be referred to as analyte strand and corresponds to a single- or double-stranded polynucleic acid molecule.

The term "labelled" refers to the use of labelled nucleic acids. This may include the use of labelled nucleotides incorporated during the polymerase step of the amplification such as illustrated by Saiki et al. (1989) or Bej et al. (1990) or labelled primers, or by any other method known to the person skilled in the art.

The present invention also relates to a method for the detection of a TTV polynucleic acid according to the invention present in a biological sample, comprising: (a) optionally extracting sample polynucleic acid, (b) hybridizing the polynucleic acid as described above with at least one probe as defined above, and (c) detecting the hybridized polynucleic acids.

The hybridization and washing conditions are to be understood as stringent and are generally known in the art (e. g. Maniatis et al., Molecular Cloning: A Laboratory Manual, New York, Cold Spring Harbor Laboratory, 1982). However, according to the hybridization solution (SSC, SSPE, etc.), these probes should be hybridized at their appropriate temperature in order to attain sufficient specificity.

According to the hybridization solution (SSC, SSPE, etc.), these probes should be stringently hybridized at their appropriate temperature in order to attain sufficient specificity. However, by slightly modifying the DNA probes, either by adding or deleting one or a few nucleotides at their extremities (either 3' or 5'), or substituting some non-essential nucleotides (i. e. nucleotides not essential to discriminate between types) by others (including modified nucleotides or inosine) these probes or variants thereof can be caused to hybridize specifically at the same hybridization conditions (i. e. the same temperature and the same hybridization solution). Also changing the amount (concentration) of probe used may be beneficial to obtain more specific hybridization results. It should be noted in this context, that probes of the same length, regardless of their GC content, will hybridize specifically at approximately the same temperature in TMACI solutions (29).

Suitable assay methods for purposes of the present invention to detect hybrids formed between the oligonucleotide probes and the polynucleic acid sequences in a sample may comprise any of the assay formats known in the art, such as the conventional dot-blot format, sandwich hybridization or reverse hybridization. For example, the detection can be accomplished using a dot blot format, the unlabelled amplified sample being bound to a membrane, the membrane being incorporated with at least one labelled probe under suitable hybridization and wash conditions, and the presence of bound probe being monitored.

An alternative and preferred method is a "reverse" dot-blot format, in which the amplified sequence contains a label. In this format, the unlabelled oligonucleotide probes are bound to a solid support and exposed to the labelled sample under appropriate stringent hybridization and subsequent washing conditions. It is to be understood that also any other assay method which relies on the formation of a hybrid between the polynucleic acids of the sample and the oligonucleotide probes according to the present invention may be used.

The present invention also relates to a method for detecting a polypeptide encoded by a TTV polynucleic acid of the present invention or an antibody against said polypeptide present in a biological sample, comprising: (a) contacting the biological sample for the presence of such polypeptide or antibody as defined above, and (b) detecting the immunological complex formed between said antibody and said polypeptide.

The immunoassay methods according to the present invention may utilize antigens from different domains of the new and unique polypeptide sequences of the present invention. It is within the scope of the invention to use for instance single or specific oligomeric antigens, dimeric antigens, as well as combinations of single or specific oligomeric antigens. The TTV antigens of the present invention may be employed in virtually any assay format that employs a known antigen to detect antibodies. Of course, a format that denatures the TTV conformational epitope should be avoided or adapted. A common feature of all of these assays is that the antigen is contacted with the body component suspected of containing TTV antibodies under conditions that permit the antigen to bind to any such antibody present in the component. Such conditions will typically be physiologic temperature, pH and ionic strength using an excess of antigen. The incubation of the antigen with the specimen is followed by detection of immune complexes comprised of the antigen.

Design of the immunoassays is subject to a great deal of variation, and many formats are known in the art. Protocols may, for example, use solid supports, or immunoprecipitation. Most assays involve the use of labeled antibody or polypeptide; the labels may be, for example, enzymatic, fluorescent, chemiluminescent, radioactive, or dye molecules. Assays which amplify the signals from the immune complex are also known; examples of which are assays which utilize biotin and avidin or streptavidin, and enzyme-labeled and mediated immunoassays, such as ELISA assays.

The immunoassay may be in a heterogeneous or in a homogeneous format, and of a standard or competitive type.

In a heterogeneous format, the polypeptide is typically bound to a solid matrix or support to facilitate separation of the sample from the polypeptide after incubation. Examples of solid supports that can be used are nitrocellulose (e. g., in membrane or microtiter well form), polyvinyl chloride (e. g., in sheets or microtiter wells), polystyrene latex (e. g., in beads or microtiter plates, polyvinylidine fluoride (known as Immunolon), diazotized paper, nylon membranes, activated beads, and Protein A beads. The solid support containing the antigenic polypeptides is typically washed after separating it from the test sample, and prior to detection of bound antibodies. Both standard and competitive formats are known in the art.

In a homogeneous format, the test sample is incubated with the combination of antigens in solution. For example, it may be under conditions that will precipitate any antigen-antibody complexes which are formed. Both standard and competitive formats for these assays are known in the art.

In a standard format, the amount of TTV antibodies in the antibody-antigen complexes is directly monitored. This may be accomplished by determining whether (labelled) anti-xenogeneic (e. g. anti-human) antibodies which recognize an epitope on anti-TTV antibodies will bind due to complex formation. In a competitive format, the amount of TTV antibodies in the sample is deduced by monitoring the competitive effect on the binding of a known amount of labeled antibody (or other competing ligand) in the complex.

Complexes formed comprising anti-TTV antibody (or in the case of competitive assays, the amount of competing antibody) are detected by any of a number of known techniques, depending on the format. For example, unlabeled TTV antibodies in the complex may be detected using a conjugate of anti-xenogeneic Ig complexed with a label (e. g. an enzyme label).

In an immunoprecipitation or agglutination assay format the reaction between the TTV antigens and the antibody forms a network that precipitates from the solution or suspension and forms a visible layer or film of precipitate. If no anti-TTV antibody is present in the test specimen, no visible precipitate is formed.

There currently exist three specific types of particle agglutination (PA) assays. These assays are used for the detection of antibodies to various antigens when coated to a support. One type of this assay is the hemagglutination assay using red blood cells (RBCs) that are sensitized by passively adsorbing antigen (or antibody) to the RBC. The addition of specific antigen/antibodies present in the body component, if any, causes the RBCs coated with the purified antigen to agglutinate.

To eliminate potential non-specific reactions in the hemagglutination assay, two artificial carriers may be used instead of RBC in the PA. The most common of these are latex particles.

The solid phase selected can include polymeric or glass beads, nitrocellulose, microparticles, microwells of a reaction tray, test tubes and magnetic beads. The signal generating compound can include an enzyme, a luminescent compound, a chromogen, a radioactive element and a chemiluminescent compound. Examples of enzymes include alkaline phosphatase, horseradish peroxidase and beta-galactosidase. Examples of enhancer compounds include biotin, anti-biotin and avidin. Examples of enhancer compounds binding members include biotin, anti-biotin and avidin.

The above methods are useful for evaluating the risk of developing diseases like cancer or an autoimmune disease due to the deleterious effects of the presence of a subgenomic TTV polynucleotide sequence by itself or linked to a particular host gene or gene fragment within the patient's cells and allow taking appropriate counter measures.

The present invention also relates to an antisense oligonucleotide or iRNA specific for the TT virus polynucleic acid of the invention.

The generation of suitable antisense oligonucleotides or iRNAs includes determination of a site or sites within the TT virus polynucleic acid for the antisense interaction to occur such that the desired effect, e.g., inhibition of expression of the polypeptide, will result. A preferred intragenic site is (a) the region encompassing the translation initiation or termination codon of the open reading frame (ORF) of the gene or (b) a region of the mRNA which is a "loop" or "bulge", i.e., not part of a secondary structure. Once one or more target sites have been identified, oligonucleotides are chosen which are sufficiently complementary to the target, i.e., hybridize sufficiently well and with sufficient specificity, to give the desired effect. In the context of this invention, "hybridization" means hydrogen bonding, which may be Watson-Crick, Hoogsteen or reversed Hoogsteen hydrogen bonding, between complementary nucleoside or nucleotide bases. "Complementary" as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound does not need to be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., in the case of therapeutic treatment.

"Oligonucleotide" (in particular in the context of antisense compounds) refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. While antisense oligonucleotides are a preferred form of the antisense compound, the present invention comprehends other oligomeric antisense compounds, including but not limited to oligonucleotide mimetics such as are described below. The antisense compounds in accordance with this invention comprise from about 8 to about 50 nucleobases (i.e. from about 8 to about 50 linked nucleosides). Particularly preferred antisense compounds are antisense oligonucleotides, even more preferably those comprising from about 15 to about 25 nucleobases. Antisense compounds include ribozymes, external guide sequences (EGS), oligonucleotides (oligozymes), and other short catalytic RNAs or catalytic oligonucleotides which hybridize to the target nucleic acid and inhibit its expression. The antisense compounds also include an iRNA comprising a sense sequence and an antisense sequence, wherein the sense and antisense sequences form an RNA duplex and wherein the antisense sequence comprises a nucleotide sequence sufficiently complementary to the nucleotide sequence of the TT virus polynucleic acid of the present invention.

Alternatively, the invention provides a vector allowing to transcribe an antisense oligonucleotide of the invention, e.g., in a mammalian host. Preferably, such a vector is a vector useful for gene therapy. Preferred vectors useful for gene therapy are viral vectors, e.g. adenovirus, herpes virus, vaccinia, or, more preferably, an RNA virus such as a retrovirus. Even more preferably, the retroviral vector is a derivative of a murine or avian retrovirus. Examples of such retroviral vectors which can be used in the present invention are: Moloney murine leukemia virus (MoMuLV), Harvey murine sarcoma virus (HaMuSV), murine mammary tumor virus (MuMTV) and Rous sarcoma virus (RSV). Most preferably, a non-human primate retroviral vector is employed, such as the gibbon ape leukemia virus (GaLV), providing a broader host range compared to murine vectors. Since recombinant retroviruses are defective, assistance is required in order to produce infectious particles. Such assistance can be provided, e.g., by using helper cell lines that contain plasmids encoding all of the structural genes of the retrovirus under the control of regulatory sequences within the LTR. Suitable helper cell lines are well known to those skilled in the art. Said vectors can additionally contain a gene encoding a selectable marker so that the transduced cells can be identified. Moreover, the retroviral vectors can be modified in such a way that they become target specific. This can be achieved, e.g., by inserting a polynucleotide encoding a sugar, a glycolipid, or a protein, preferably an antibody. Those skilled in the art know additional methods for generating target specific vectors. Further suitable vectors and methods for in vitro- or in vivo-gene therapy are described in the literature and are known to the persons skilled in the art; see, e.g., WO 94/29469 or WO 97/00957. The TTV polynucleotide sequences of the invention may also serve as a suitable vector itself, either composed solely of rearranged TT viral sequences or of chimeric TTV host cell DNA sequences. In addition, the nucleotide sequences of the invention may be used for the construction of artificial chromosomes.

In order to achieve expression only in the target organ, the DNA sequences for transcription of the antisense oligonucleotides can be linked to a tissue specific promoter and used for gene therapy. Such promoters are well known to those skilled in the art (30-33).

Within an oligonucleotide structure, the phosphate groups are commonly referred to as forming the internucleoside backbone of the oligonucleotide. The normal linkage or backbone of RNA and DNA is a 3' to 5' phosphodiester linkage. Specific examples of preferred antisense compounds useful in the present invention include oligonucleotides containing modified backbones or non-natural internucleoside linkages. Oligonucleotides having modified backbones include those that retain a phosphorus atom in the backbone and those that do not have a phosphorus atom in the backbone. Modified oligonucleotide backbones which can result in increased stability are known to the person skilled in the art, preferably such modification is a phosphorothioate linkage.

A preferred oligonucleotide mimetic is an oligonucleotide mimetic that has been shown to have excellent hybridization properties, and is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone (34).

Modified oligonucleotides may also contain one or more substituted or modified sugar moieties. Preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. A particularly preferred modified sugar moiety is a 2'-O-methoxyethyl sugar moiety.

Antisense-oligonucleotides of the invention may also include nucleobase modifications or substitutions. Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine etc., with 5-methylcytosine substitutions being preferred since these modifications have been shown to increase nucleic acid duplex stability.

Another modification of the oligonucleotides of the invention involves chemically linking to the oligonucleotide one or more moieties or conjugates which enhance the activity, cellular distribution or cellular uptake of the oligonucleotide. Such moieties include lipid moieties such as a cholesterol moiety, cholic acid, a thioether, a thiocholesterol, an aliphatic chain, e.g., dodecandiol or undecyl residues, a phospholipid, a polyamine or a polyethylene glycol chain, or adamantane acetic acid, a palmityl moiety, or an octadecylamine or hexylamino-carbonyl-oxycholesterol moiety.

The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers.

The present invention also relates to a pharmaceutical composition comprising an antibody or antisense oligonucleotide of the invention and a suitable excipient, diluent or carrier. Preferably, in a pharmaceutical composition, such compound as described above is combined with a pharmaceutically acceptable carrier. "Pharmaceutically acceptable" is meant to encompass any carrier, which does not interfere with the effectiveness of the biological activity of the active ingredient and that is not toxic to the host to which it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and the active compound can be administered to the subject at an effective dose.

An "effective dose" refers to an amount of the active ingredient that is sufficient to prevent the disease or to affect the course and the severity of the disease, leading to the reduction or remission of such pathology. An "effective dose" useful for treating and/or preventing these diseases or disorders may be determined using methods known to one skilled in the art (35).

Administration of the suitable compositions may be effected by different ways, e.g. by intravenous, intraperitoneal, subcutaneous, intramuscular, topical or intradermal administration. The route of administration, of course, depends on the kind of therapy and the kind of compound contained in the pharmaceutical composition. The dosage regimen will be determined by the attending physician and other clinical factors. As is well known in the medical arts, dosages for any one patient depends on many factors, including the patient's size, body surface area, age, sex, the particular compound to be administered, time and route of administration, the kind of therapy, general health and other drugs being administered concurrently.

In a preferred embodiment of the present invention, the disease that can be prevented/treated is cancer, preferably breast cancer, colorectal cancer, pancreatic cancer, Hodgkin's lymphoma, B-lymphoma, acute lymphocytic leukaemia, and Burkitt's lymphoma, or an autoimmune disease such as multiple sclerosis (MS), asthma, lupus erythematosus or Crohn's disease. The terms "cancer" and "autoimmune disease" also comprise early stages of said diseases.

The present invention also relates to a vaccine for immunizing a mammal against TTV infection, comprising at least one polypeptide or TT virus polynucleic acid as defined above, in a pharmaceutically acceptable carrier.

A "vaccine" is an immunogenic composition capable of eliciting protection against TTV, whether partial or complete. A vaccine may also be useful for treatment of an individual, in which case it is called a therapeutic vaccine.

The term "therapeutic" refers to a composition capable of treating TTV infection. The term "effective amount" refers to an amount of epitope-bearing polypeptide sufficient to induce an immunogenic response in the individual to which it is administered, or to otherwise detectably immunoreact in its intended system (e. g., immunoassay). Preferably, the effective amount is sufficient to effect treatment, as defined above. The exact amount necessary will vary according to the application. For vaccine applications or for the generation of polyclonal antiserum/antibodies, for example, the effective amount may vary depending on the species, age, and general condition of the individual, the severity of the condition being treated, the particular polypeptide selected and its mode of administration, etc. Effective amounts will be found within a relatively large, non-critical range. An appropriate effective amount can be readily determined using only routine experimentation. Preferred ranges of proteins for prophylaxis of TTV caused diseases are 0.01 to 100 µg/dose, preferably 0.1 to 50 µg/dose. Several doses may be needed per individual in order to achieve a sufficient immune response and subsequent protection against a TTV infection and a TTV caused disease, respectively.

Pharmaceutically acceptable carriers include any carrier that does not itself induce the production of antibodies harmful to the individual receiving the vaccine. Suitable carriers are typically large, slowly metabolized macromolecules such as proteins, polysaccharides, polylactic acids, polyglycolic acids, polymeric amino acids, and amino acid copolymers. Such carriers are well known to those of ordinary skill in the art.

Preferred adjuvants to enhance effectiveness of the composition include, but are not limited to: aluminim hydroxide (alum), N-acetyl-muramyl-L-threonyl-D-isoglutamine (thr-MDP) as found in U.S. Pat. No. 4,606,918, N-acetyl-normuramyl-L-alanyl-D-isoglutamine (nor-MDP), N-acetylmuramyl-L-alanyl-D-isoglutaminyl-L-alanine-2-(1'-2'-dipalmitoyl sn-glycero-3-hydroxy-phosphoryloxy)-ethylamine (MTP-PE) and RIBI, which contains three components extracted from bacteria, monophosphoryl lipid A, trehalose dimycolate, and cell wall Skeleton (MPL+TDM+CWS) in a 2% squalene/Tween 80 emulsion. Any of the 3 components MPL, TDM or CWS may also be used alone or combined 2 by 2. Additionally, adjuvants such as Stimulon (Cambridge Bioscience, Worcester, Mass.) or SAF-1 (Syntex) may be used. Further, Complete Freund's Adjuvant (CFA) and Incomplete Freund's Adjuvant (IFA) may be used for non-human applications and research purposes.

The immunogenic compositions typically will contain pharmaceutically acceptable vehicles, such as water, saline, glycerol, ethanol, etc. Additionally, auxiliary substances, such as wetting or emulsifying agents, pH buffering substances, preservatives, and the like, may be included in such vehicles.

Typically, the immunogenic compositions are prepared as injectables, either as liquid solutions or suspensions. Solid forms suitable for solution in, or suspension in, liquid vehicles prior to injection may also be prepared. The preparation also may be emulsified or encapsulated in liposomes for enhanced adjuvant effect. The proteins may also be incorporated into Immune Stimulating Complexes together with saponins, for example Quil A (ISCOMS).

Immunogenic compositions used as vaccines comprise a "sufficient amount" or "an immunologically effective amount" of the proteins of the present invention, as well as any other of the above mentioned components, as needed. "Immunologically effective amount" means that the administration of that amount to an individual, either in a single dose or as part of a series, is effective for treatment, as defined above. This amount varies depending upon the health and physical condition of the individual to be treated, the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials. Usually, the amount will vary from 0.01 to 1000 µg/dose, more particularly from 0.1-100 µg/dose.

Finally, the present invention also provides
(a) a method for the generation of a database for determining the risk to develop cancer or an autoimmune disease, comprising the following steps
(i) determining the nucleotide sequence of a host cell DNA linked to TT virus polynucleic acids according to the invention and being present in episomal form, if present, in a sample from a patient suffering from at least one of said diseases; and
(ii) compiling sequences determined in step (a) associated with said diseases in a database; as well as
(b) a method for evaluating the risk to develop cancer or an autoimmune disease of a patient suspected of being at risk of developing such disease, comprising the following steps
(i) determining the nucleotide sequence of a host cell DNA linked to TT virus polynucleic acids according to the invention and being present in episomal form, if present, in a sample from said patient; and
(ii) comparing sequences determined in step (a) with the sequences compiled in the database generated to the method described above, wherein the absence of a host cell DNA linked to a TT virus polynucleic acid or the presence only of host cell DNA linked to a TT virus polynucleic acid not represented in said database indicates that the risk of developing such disease is decreased or absent.

The following examples are intended to illustrate, but not to limit the invention. While such examples are typical of those that might be used, other methods known to those skilled in the art may alternatively be utilized.

Example 1

Demonstration of the Persistence of TTV DNA in Cells from Tissue Culture Lines Derived from Malignant Tumors Cell lines derived from malignant tumors possess one advantage over primary tumor biopsy material. They commonly represent pure preparations of cancer cells, whereas primary materials are commonly contaminated by normal mesenchymal cells, by cells of the hematopoietic system and normal epithelial cells. On the other hand, one disadvantage of tissue culture lines may arise from the selection of specific clones growing under tissue culture conditions and the acquisition of secondary genetic modifications in the course of long-term cultivation. In addition, fetal calf sera may pose a risk due to the introduction of cattle viruses which survive serum inactivation procedures (e.g. bovine polyomavirus); see Table 1 summarizing these advantages/disadvantages.

Table 1

Attempts to find TTV DNA in human primary tumor materials suffers from one disadvantage: the plurality of TTV genotypes in human material (8). This renders it virtually impossible to identify a specific genotype as an etiologic agent for a human cancer type. For these reasons studies on the persistence of TTV DNA sequences in cells derived from cancer tissue culture lines were initiated. Thus far the results have been extremely surprising: PCR primers used to discover regions of the TTV large open reading frame have been entirely unsuccessful. However, other primer combinations, discovering exclusively a short GC-rich regulatory region of the TTV genome of about 71 bases, detected this sequence in a larger number of cell lines (FIG. 1). This regulatory region is highly conserved among different TTV genotypes and is not present in the human genome data bank.

In a first series of experiments the same sequence was discovered in a number of additional cell lines. These included the following lines:
1=7 (breast cancer line);
HAK-1, KMH-2, L1236 (all Epstein-Barr virus negative Hodgkin's lymphoma lines);
Y69 (Epstein-Barr virus negative B-lymphoma)
HSB-2 (acute lymphocytic leukemia);
P3HR-1 (Epstein-Barr virus-positive Burkitt's lymphoma);
BJAB (Epstein-Barr virus negative Burkitt's lymphoma);
Ng (EBV-immortalized B lymphoblasts from a patient with multiple sclerosis)-

Figure 2:
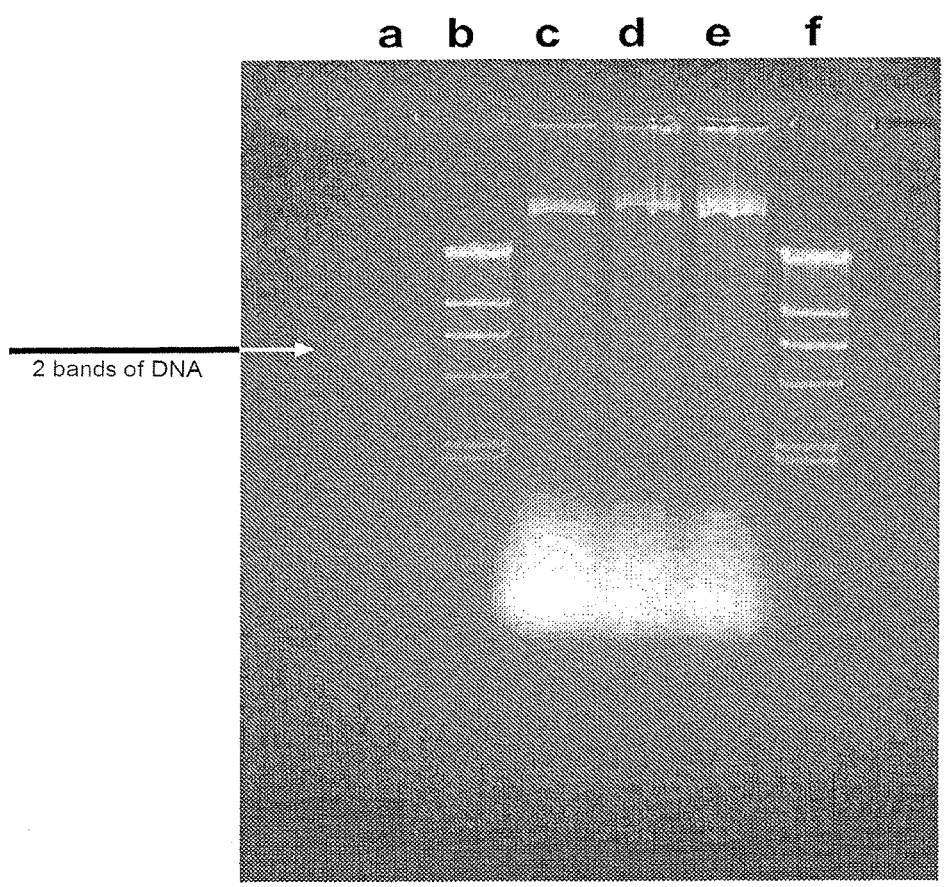

Besides these 9 positive lines, two melanoma cell lines (IGL and KR, FIG. 1) and human placenta DNA were negative in initial experiments. Interestingly, after removal of spooled DNA from L1236 cells and RNase treatment of the remaining solution, besides mitochondrial DNA two faint bands of similar size became visible banding between positions 4.3-6.6 kb (double-stranded DNA size marker) in the agarose gels (FIG. 2). Analysis of these sequences revealed again the presence of the TTV regulatory region. Mung-bean nuclease, digesting selectively single-stranded DNA, completely abolished the cellular DNA-containing bands from four multiple sclerosis biopsies in contrast to double-stranded control DNA, underlining the single-stranded nature of the former. Similar studies are presently conducted for isolates from tumor DNA.

Example 2

Analyses of Chimeric TTV/Truncated Host Cell DNA Sequences

Initially, all attempts failed to use primers in outwards orientation starting within the regulatory region in order to find flanking TT viral DNA, surrounding this region. Invariably, however, human cellular DNA was demonstrated in the respective clones (FIG. 3).

The human genes in these clones and their arrangements within the single-stranded episomal DNA, obviously controlled by the TTV 71 base region, are presently being analyzed. The available data indicate a substantial variation in the uptake of commonly truncated host cell genes. Their possible conversion into growth-stimulating oncogenes or into functions interfering with tumorsuppressor genes requires functional tests which are presently under investigation. The same accounts for rearranged TTV virus sequences. Some of the available data are presented in FIGS. 7, 8, 9, and 11 to 13.

LIST OF REFERENCES

1. Nishizawa, T., Okamoto, H., Kato, N. et al. A novel DNA virus (TTV) associated with elevated transaminase levels in posttransfusion hepatitis of unknown etiology. Biochem. Biophys. Fes. Commun. 241: 92-97, 1997.
2. Okamoto, H. TT viruses in animals. Review. In: TT Viruses, the still Elusive Pathogens (de Villiers, E.-M., zur Hausen, H. eds.), Curr. Topics Microbiol. Immunol. E.-M. de Villiers, H. zur Hausen (Eds), Vol. 331: 35-52, 2009.
3. Biagini, P., Todd, D., Bendinelli, M. et al., Anellovirus. In: Virus Taxonomy, VIIIth Report of the International Committee for the Taxonomy of Viruses. London: Elsevier/ Academic Press pp. 335-341, 2005.
4. Gerner, P., Oettinger, R., Gerner, W., et al. Mother-to-infant transmission of TT virus: prevalence, extent and mechanism of vertical transmission. Pediatr. Infect. Dis. J. 19: 1074-1077, 2000.
5. Goto, K., Sugiyama, K., Ando, T., e al., Detection rates of TT virus DNA in serum of umbilical cord blood, breast milk and saliva. Tohoku J., Exp. Med. 191: 203-207, 2000.
6. Borkosky, S., Whitley, C., and de Villiers, E.-M., unpublished results.
7. Leppik, L., Gunst, K., Lehtinen, M., et al., In vivo and in vitro intragenomic rearrangement of TT viruses. J. Virol. 81: 9346-9356, 2007.
8. Jelcic, I., Hotz-Wagenblatt, A., Hunzicker, A., et al. Isolation of multiple TT virus genotypes from spleen biopsy tissue from a Hodgkin's disease patient: genome reorganization and diversity of the hypervariable region. J. Virol. 78: 7498-7507, 2004.
9. de Villiers, E.-M., Schmidt, R., Delius, H., et al. Heterogenetity of TT virus related sequences isolated from human tumour biopsy specimens. J. Mol. Med. 80: 44-50, 2002.
10. de Villiers, E.-M., Bulajic, M., Nitsch, C., et al. TTV infection in colorectal cancer tissues and normal mucosa. Int. J. Cancer 121: 2109-2112, 2007.
11. de Villiers, E. M., Kimmel, R., Leppik, L., and Gunst, K. Intragenomic rearrangements in TT viruses; a possible role in the pathogenesis of disease. In: TT Viruses, the still Elusive Pathogens (de Villiers, E.-M., zur Hausen, H. eds.), Curr. Topics Microbiol. Immunol. 331: 91-107, 2009.
12. Matsukara, M., Shinozuka, K., Zon, G., Mitsuya, H., Reitz, M., Cohen, J., Broder, S. Proc. Natl. Acad. Sci. USA 84(21): 7706-10 (1987).
13. Miller, P., Yano, J., Yano, E., Carroll, C., Jayaram, K., Ts'o, P. (1979) Nonionic nucleic acid analogues. Synthesis and characterization of dideoxyribonucleoside methylphosphonates. Biochemistry 18(23): 5134-43.
14. Nielsen, P., Egholm, M., Berg, R., Buchardt, O. (1991) Sequence-selective recognition of DNA by strand displacement with a thymine-substituted polyamide. Science 254(5037): 1497-500.
15. Nielsen, P., Egholm, M., Berg, R., Buchardt, O. (1993) Sequence specific inhibition of DNA restriction enzyme cleavage by PNA. Nucleic-Acids-Res. 21(2): 197-200.
16. Asseline, U., Delarue, M., Lancelot, G., Toulme, F., Thuong, N. (1984) Nucleic acid-binding molecules with high affinity and base sequence specificity: intercalating agents covalently linked to oligodeoxynucleotides. Proc. Natl. Acad. Sci. USA 81(11): 3297-301.
17. Kwok, S., Kellogg, D E., McKinney, N., Spasic, D., Goda, L., Levenson, C., Sninsky, J J. (1990) Effects of primer-template mismatches on the polymerase chain reaction: human immunodeficiency virus type 1 model studies. Nucleic Acids Res 18: 999-1005.
18. Landgren, U., Kaiser, R., Sanders, J., Hood, L. (1988) A ligase-mediated gene detection technique. Science 241: 1077-1080.
19. Wu, D., Wallace, B. (1989) The ligation amplification reaction (LAR)-amplification of specific DNA sequences using sequential rounds of template-dependent ligation. Genomics 4: 560-569.
20. Walker, G T., Fraiser, M S., Schram, J L., Little, M C., Nadeau, J G., Malinowski, D P. (1992) Strand displacement amplification—an isothermal, in vitro DNA amplification technique. Nucleic Acids Res 20: 1691-6.
21. Guatelli, J., Whitfield, K., Kwoh, D., Barringer, K., Richman, D., Gengeras, T. (1990) Isothermal, in vitro amplification of nucleic acids by a multienzyme reaction modeled after retroviral replication. Proc Natl Acad Sci USA 87: 1874-1878.
22. Compton, J. (1991) Nucleic acid sequence-based amplification. Nature 350: 91-92.
23. Kwoh, D Y., Davis, G R., Whitfield, K M., Chappelle, H L., DiMichele, L J., Gingeras, T R. (1986) Transcription-based amplification system and detection of amplified human immunodeficiency virus type 1 with a bead-based sandwich hybridization format. Proc Natl Acad Sci USA, 86: 1173-7.
24. Duck, P. (1990) Probe amplifier system based on chimeric cycling oligonucleotides. Biotechniques 9: 142-147.
25. Lizardi, P M., Kramer, F R. (1991) Exponential amplification of nucleic acids: new diagnostics using DNA polymerases and RNA replicases. Trends Biotechnol 19: 53-8.
26. Lomeli, H., Tyagi, S., Pritchard, C G., Lizardi, P M., Kramer, F R. (1989) Quantitative assays based on the use of replicatable hybridization probes. Clin Chem 35: 1826-31.
27. Köhler et al., Nature 256 (1975), 495.
28. Wahl et al., J. Nucl. Med. 24: 316-325 (1983).
29. Jacobs, K A. et al. (1988) The thermal stability of oligonucleotide duplexes is sequence independent in tetraalkylammonium salt solutions: application to indeifying recobinant DNA clones. Nucleic Acids Res 16:4637-50.
30. Zimmermann et al., (1994) Neuron 12, 11-24.
31. Vidal et al.; (1990) EMBO J. 9, 833-840.
32. Mayford et al., (1995), Cell 81, 891-904.
33. Pinkert et al., (1987) Genes & Dev. 1, 268-76).
34. Nielsen et al., Science 254 (1991), 1497-1500.
35. Fingl et al., The Pharmacological Basis of Therapeutics, Goodman and Gilman, eds. Macmillan Publishing Co., New York, pp. 1-46 (1975).

What is claimed is:

1. A recombinant expression vector comprising a torque teno (TT) virus polynucleic acid operably linked to prokaryotic or eukaryotic transcription or translation control elements, wherein the control elements are ligated such that a desired open reading frame is expressed and the TT virus polynucleic acid comprises one of the four nucleotide sequences of SEQ ID NOS:1-4.

2. The recombinant expression vector of claim 1 which is a single-stranded DNA.

3. The recombinant expression vector of claim 1, wherein the vector is selected from the group consisting of a plasmid, a cosmid, an artificial chromosome, a phage and a virus.

4. The recombinant expression vector of claim 3, wherein the virus is selected from the group consisting of a TT virus recombinant molecule, adenoviral vector, a vaccine virus, Ankara Modified Virus (AMV) and avipox recombinant virus.

5. The recombinant expression vector of claim 1, wherein the sequence of the desired open reading frame for expression is attached to a signal sequence.

6. The recombinant expression vector of claim 1, wherein the control elements comprise elements selected from the group consisting of promoters, splicing sites, terminators and enhancers.

7. The recombinant expression vector of claim 1, wherein the TT virus polynucleic acid is linked to a host cell DNA.

8. The recombinant expression vector of claim 1 comprising a nucleotide sequence selected from the group consisting of SEQ ID NOS: 5-7, 13, 18-19, 26-27, 28-29 and 30-31.

9. An artificial chromosome comprising the expression vector of claim 1.

10. The recombinant expression vector of claim 1 further comprising a desired open reading frame.

11. The recombinant expression vector of claim 1, wherein the
TT virus polynucleotide sequence consists of one of the four nucleotide sequences of SEQ ID NOS:1-4.

12. The recombinant expression vector of claim 11 which is a single-stranded DNA.

13. The recombinant expression vector of claim 11, wherein the vector is selected from the group consisting of a plasmid, a cosmid, an artificial chromosome, a phage and a virus.

14. The recombinant expression vector of claim 13, wherein the virus is selected from the group consisting of a TT virus recombinant molecule, adenoviral vector, a vaccine virus, Ankara Modified Virus (AMV) and avipox recombinant virus.

15. The recombinant expression vector of claim 11, wherein the vector comprises control elements which are ligated such that a desired open reading frame is expressed and the desired open reading frame for expression is attached to a signal sequence.

16. The recombinant expression vector of claim 11, wherein the vector comprises control elements selected from the group consisting of promoters, splicing sites, terminators and enhancers.

17. The recombinant expression vector of claim 11, wherein the TT virus polynucleic acid is linked to a host cell DNA.

18. The recombinant expression vector of claim 11 comprising a nucleotide sequence selected from the group consisting of SEQ ID NOS: 5-7, 13, 18-19, 26-27, 28-29 and 30-31.

19. An artificial chromosome comprising the expression vector of claim 11.

20. The recombinant expression vector of claim 11 further comprising a desired open reading frame.

\* \* \* \* \*